United States Patent
Hoffman et al.

(10) Patent No.: US 9,173,884 B2
(45) Date of Patent: Nov. 3, 2015

(54) INHIBITORS OF PHOSPHODIESTERASE 11 (PDE11)

(71) Applicant: TRUSTEES OF BOSTON COLLEGE, Chestnut Hill, MA (US)

(72) Inventors: Charles Stuart Hoffman, Waltham, MA (US); Ozge Ceyhan, Brighton, MA (US)

(73) Assignee: Trustees of Boston College, Chestnut Hill, MA (US)

( * ) Notice: Subject to any disclaimer, the term of this patent is extended or adjusted under 35 U.S.C. 154(b) by 0 days.

(21) Appl. No.: 14/361,979

(22) PCT Filed: Nov. 29, 2012

(86) PCT No.: PCT/US2012/067048
§ 371 (c)(1),
(2) Date: May 30, 2014

(87) PCT Pub. No.: WO2013/082275
PCT Pub. Date: Jun. 6, 2013

(65) Prior Publication Data
US 2014/0323503 A1    Oct. 30, 2014

Related U.S. Application Data

(60) Provisional application No. 61/565,238, filed on Nov. 30, 2011.

(51) Int. Cl.
| | | |
|---|---|---|
| C07D 495/04 | (2006.01) |
| A61K 31/519 | (2006.01) |
| C07D 513/04 | (2006.01) |
| A61K 45/06 | (2006.01) |
| A61K 31/416 | (2006.01) |
| A61K 31/437 | (2006.01) |
| A61K 31/53 | (2006.01) |
| A61K 31/573 | (2006.01) |

(52) U.S. Cl.
CPC ............ *A61K 31/519* (2013.01); *A61K 31/416* (2013.01); *A61K 31/437* (2013.01); *A61K 31/53* (2013.01); *A61K 31/573* (2013.01); *A61K 45/06* (2013.01); *C07D 513/04* (2013.01)

(58) Field of Classification Search
USPC ...................................................... 544/278
See application file for complete search history.

(56) References Cited

U.S. PATENT DOCUMENTS

| 8,445,491 B2 * | 5/2013 | Lum et al. ...................... 514/248 |
| 8,642,660 B2 * | 2/2014 | Goldfarb ....................... 514/641 |
| 2008/0090845 A1 * | 4/2008 | Blum et al. ................. 514/260.1 |
| 2009/0163545 A1 * | 6/2009 | Goldfarb ....................... 514/312 |

FOREIGN PATENT DOCUMENTS

WO        2009/140127 A2    11/2009
WO    WO 2009155001 A2 *  12/2009

OTHER PUBLICATIONS

Chen et al Nature Chemical Biology vol. 5(2) (2009) pp. 100-107.*
Chakraborti et al. "3D-QSAR Studies on thieno[3,2-d]pyrimidines as Phosphodiesterase IV Inhibitors." Bioorganic & Medicinal Chemistry Letters, Pergamon, Elsevier Science, GB, vol. 13, No. 8, Jan. 1, 2003, pp. 1403-1408.
Les et al. "A theoretical study of tautomerism: 2- and 4-oxopyrimidine and some of their derivatives." International J. of Quantum Chemistry, vol. 27, No. 5, May 1, 1985, pp. 567-583.
Ceyhan et al. "Identification of Biologically Active PDE11-Selective Inhibitors Using a Yeast-Based High-Throughput Screen." Chemistry and Biology, vol. 19, No. 1, Jan. 1, 2012, pp. 155-163.

* cited by examiner

*Primary Examiner* — Nyeemah A Grazier
(74) *Attorney, Agent, or Firm* — Nixon Peabody LLP

(57) ABSTRACT

The present intervention generally relates to compositions comprising a PDE11 inhibitor for increasing cortisol levels in a subject, or for increasing the production of cortisol from adenocortical cells in a subject. Aspects of the invention relate to the use of a PDE11 inhibitor in a method of treatment of low cortisol levels and/or adrenal insufficiency in a subject, or a method of treating a disease or disorders associated with adrenal insufficiency. Aspects of the invention relate to PDE11 inhibitors belonging to compounds of formula (I)-(VI), and their use alone or in combination with long-term corticosteroid treatment to elevate cortisol levels in a subject, and/or to treat adrenal insufficiency. Another aspect relates to kits comprising PDE11 inhibitors for administration to a subject, pharmaceutical compositions comprising compounds of formula (I)-(VI) for use in methods to increase cortisol levels and/or treat adrenal insufficiency, and their use as an adjuvant for treatment of cancer or other disorders such as psychiatric diseases where elevating cortisol levels would be beneficial to the subject.

3 Claims, 19 Drawing Sheets

| | BC11-15 | BC11-19 | BC11-28 | BC11-38 |
|---|---|---|---|---|
| MW | 404.5 | 295.3 | 394.4 | 304.4 |
| PDE11 | 0.18 | 0.33 | 0.11 | 0.28 |
| PDE1 | >100 | 10 | >100 | >100 |
| PDE2 | >100 | >100 | >100 | >100 |
| PDE3 | >100 | 51 | >100 | >100 |
| PDE4 | 70 | >100 | >100 | >100 |
| PDE5 | 43 | >100 | >100 | >100 |
| PDE6 | 25 | >100 | >100 | >100 |
| PDE7 | 43 | >100 | >100 | >100 |
| PDE8 | >100 | >100 | >100 | >100 |
| PDE9 | >100 | >100 | >100 | >100 |
| PDE10 | 35 | >100 | >100 | >100 |

| | BC11-38-1 | BC11-38-2 | BC11-38-3 | BC11-38-4 |
|---|---|---|---|---|
| MW | 318.5 | 318.5 | 318.5 | 334.5 |
| PDE11 | 0.4 | 2.5 | 7.5 | 9.9 |
| PDE1 | 90 | >100 | >100 | >100 |
| PDE2 | 40 | 8.4 | >100 | >100 |
| PDE3 | >100 | >100 | >100 | >100 |
| PDE4 | >100 | 23.3 | >100 | 60 |
| PDE5 | >100 | >100 | >100 | >100 |
| PDE6 | >100 | 51.2 | >100 | >100 |
| PDE7 | >100 | >100 | 21.3 | >100 |
| PDE8 | >100 | >100 | >100 | >100 |
| PDE9 | >100 | >100 | >100 | >100 |
| PDE10 | >100 | 5 | >100 | 5.8 |

Row label: IC$_{50}$ (μM)

*FIG. 5A*

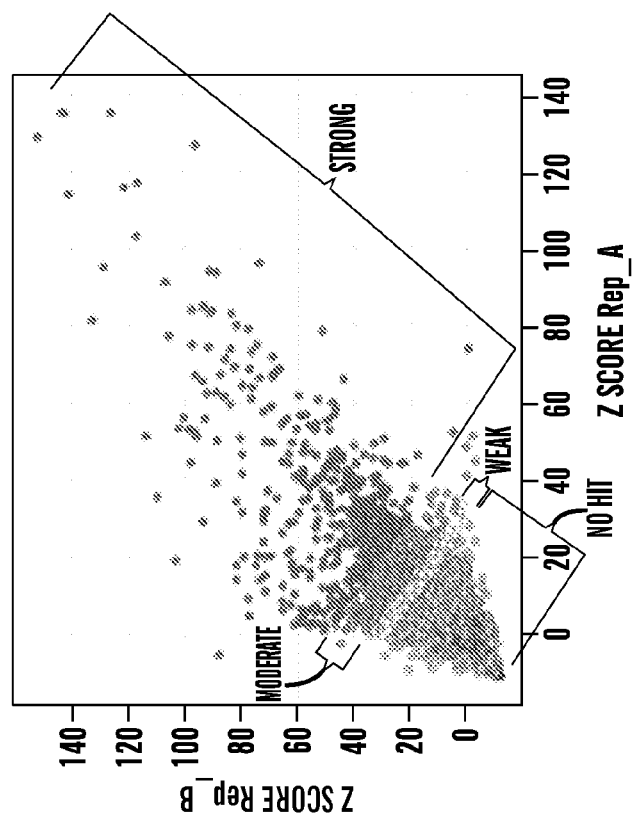
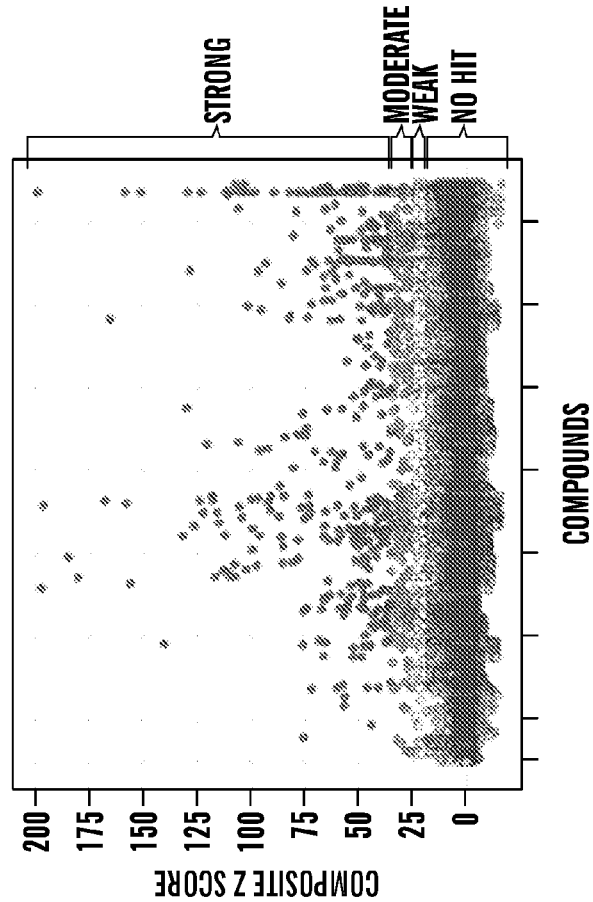
FIG. 7B
FIG. 7A

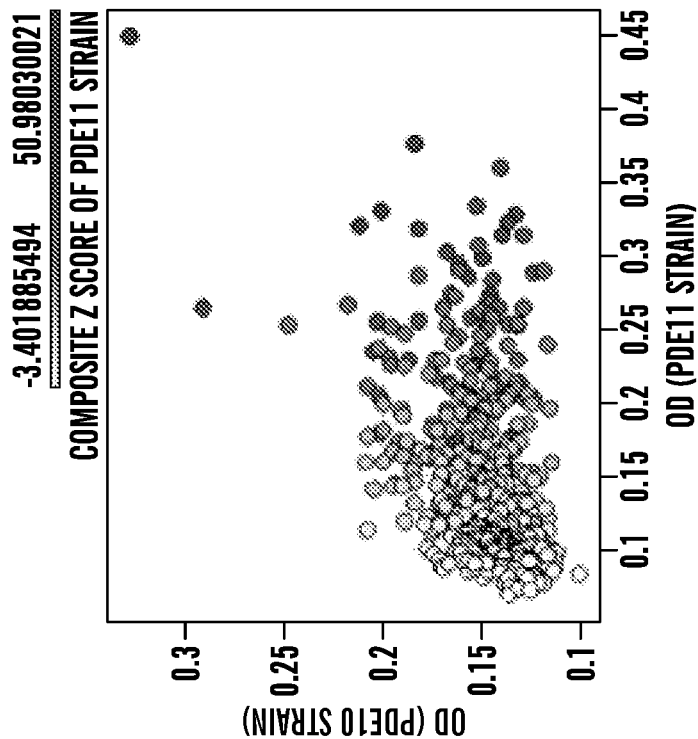
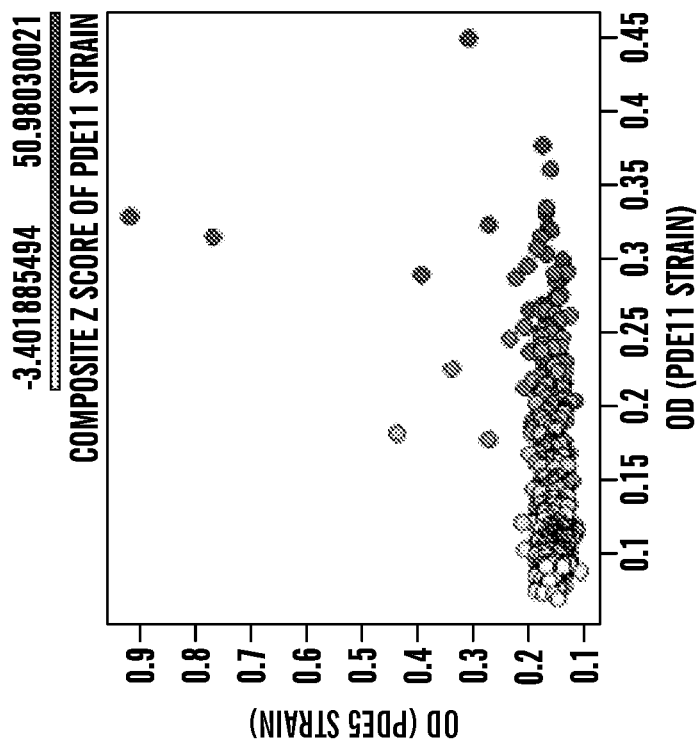
FIG. 8B
FIG. 8C

BC11-19
Maybridge BTB 12009
IC50=0.33μM AGAINST PDE11A

BC11-19-1
ChemBridge 7140503
THIS COMPOUND SHOWS NO
PDE11 INHIBITION AT 2μM

BC11-19-2
ChemBridge 7353803, MW=339
IC50 OF ~2μM AGAINST PDE11A.

BC11-19-3
ChemBridge 7354721
IC50 OF >2mM AGAINST PDE11A
(ENZYME DISPLAYS 89.9% ACTIVITY IN THE
PRESENCE OF 2μM COMPOUND).

BC11-19-4
ChemBridge 7353529
IC50 OF >2μM AGAINST PDE11A
(ENZYME DISPLAYS 81.1% ACTIVITY IN THE
PRESENCE OF 2μM COMPOUND).

BC11-19-5
ChemBridge 7353611
IC50 OF ~2μM AGAINST PDE11A.

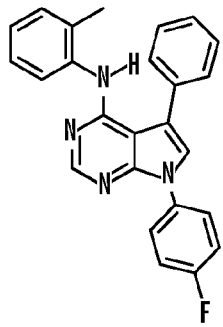

BC11-28
BC11-28 SAR
ChemDiv K405-0344
IC50 OF 0.11 μM AGAINST PDE11A.

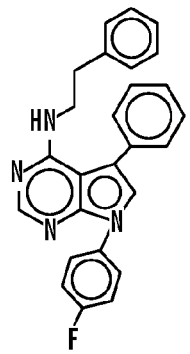

BC11-28-1
ChemDiv K405-0340
IC50 OF <1.0 μM AGAINST PDE11A.

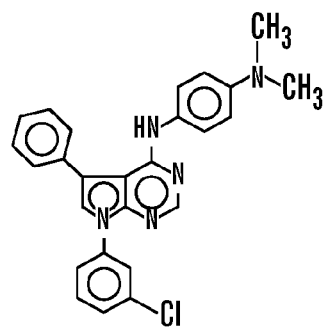

BC11-28-2
ChemDiv K405-0296
IC50 OF >2mM AGAINST PDE11A
(ENZYME DISPLAYS 72.3% ACTIVITY IN THE
PRESENCE OF 2μM COMPOUND).

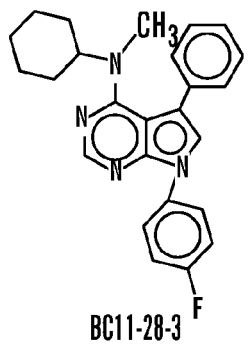

BC11-28-3
ChemDiv K405-1140
IC50 OF >2mM AGAINST PDE11A
(ENZYME DISPLAYS 76.6% ACTIVITY IN THE
PRESENCE OF 2μM COMPOUND).

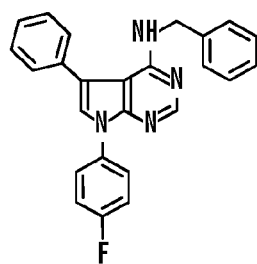

BC11-28-4
ChemDiv K405-0332
IC50 BETWEEN 1 AND 2μM
AGAINST PDE11A

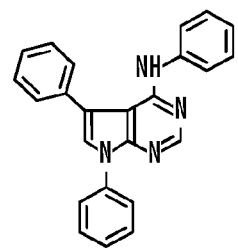

BC11-28-5
ChemDiv K405-1231
IC50 OF <0.2μM AGAINST PDE11A

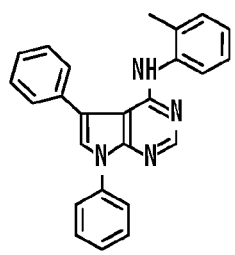

BC11-28-6
ChemDiv K405-0043 (MW 376.453)
IC50 OF <0.2μM AGAINST PDE11A

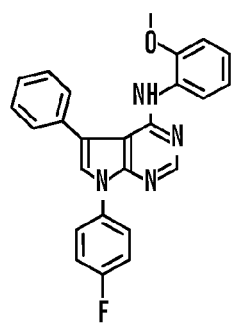

BC11-28-7
ChemDiv K405-0349
IC50 OF <0.2μM AGAINST PDE11A

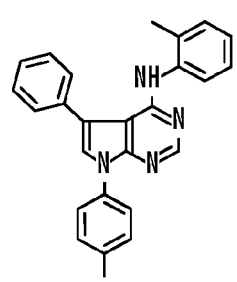

BC11-28-8
ChemDiv K405-0438
IC50 OF ~0.5μM AGAINST PDE11A

*FIG. 11*

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tggagtggat tgatagcatc tg                                                  22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttggtgtag ctcttcccac                                                     20
```

INHIBITORS OF PHOSPHODIESTERASE 11 (PDE11)

CROSS REFERENCE TO RELATED APPLICATIONS

This application is a 35 U.S.C. §371 National Phase Entry Application of International Application No. PCT/US2012/067048 filed Nov. 29, 2012, which designates the U.S., and which claims benefit under 35 U.S.C. §119(e) of the U.S. provisional application No. 61/565,238 filed Nov. 30, 2011, the contents of which is incorporated herein by reference in it's entirety.

SEQUENCE LISTING

The instant application contains a Sequence Listing which has been filed electronically in ASCII format and is hereby incorporated by reference in its entirety. Said ASCII copy, created on Sep. 16, 2015, is named 051566-071552-US_S-L.txt and is 798 bytes in size.

FIELD OF THE INVENTION

The present invention is directed to phosphodiesterase 11 (PDE11) inhibitor compounds for use in methods for the treatment of subjects with low cortisol levels, and methods to increase cortisol production, and methods for treatment of adrenal insufficiencies and methods for cancer chemotherapy, as well as kits and pharmaceutical compositions.

BACKGROUND OF THE INVENTION

High cortisol levels can lead to a variety of different health issues and cortisol levels can increase in the aging population or related to stress. In many instances, the key to controlling intracellular levels of these molecules is their hydrolysis by cyclic nucleotide phosphodiesterases (PDEs). Cyclic nucleotide phosphodiesterases (PDEs) catalyze the hydrolysis of cyclic nucleotides, such as the second messengers cAMP (cyclic adenosine 3'5'-monophosphate) and cGMP (cyclic guanine 3'5'-monophosphate). Thus, different PDEs play pivotal regulatory roles in a wide variety of signal transduction pathways (Beavo, Physiol. Rev. 75: 725-48, 1995). For example, certain PDEs mediate processes involved in vision (McLaughlin et al., Nat. Genet. 4: 130-34, 1993), olfaction (Yan et al., Proc. Natl. Acad. Sci. USA 92: 9677-81, 1995), platelet aggregation (Dickinson et al. Biochem. J. 323: 371-77, 1997), aldosterone synthesis (MacFarland et al., J. Biol. Chem. 266: 136-42, 1991), insulin secretion (Zhao et al., J. Clin. Invest. 102: 869-73, 1998), T cell activation (Li et al., Science 283: 848-51, 1999), and smooth muscle relaxation (Boolell et al., Int. J. Impot. Res. 8: 47-52, 1996; Ballard et al., J. Urol. 159: 2164-71, 1998).

Mammals express eleven families of PDEs (3 cAMP-specific, 3 cGMP-specific, and 5 dual-specificity), encoded by 21 genes that produce over 100 distinct PDE isoenzymes due to alternative splicing of the transcript (Beavo, Physiol. Rev. 75: 725-48, 1995; Beavo et al., Mol. Pharmacol. 46: 399-05, 1994; Soderling et al., Proc. Natl. Acad. Sci. USA 95: 8991-96, 1998; Fisher et al., Biochem. Biophys. Res. Commun. 246: 570-77, 1998; Hayashi et al., Biochem. Biophys. Res. Commun. 250: 751-56, 1998; Soderling et al., J. Biol. Chem. 273: 15553-58, 1998; Fisher et al., J. Biol. Chem. 273: 15559-64, 1998; Soderling et al., Proc. Natl. Acad. Sci. USA 96: 7071-76, 1999; and Fawcett et al., Proc. Natl. Acad. Sci. USA 97: 3702-07, 2000). These enzymes perform distinct functions in the body due to tissue-specific expression, as well as subcellular localization of PDE isoforms and the effector proteins regulated by cAMP or cGMP levels. Given the complexity of this superfamily for which there are only two substrates; cAMP and cGMP, compounds that specifically and selectively inhibit individual PDEs can be powerful tools to advance our understanding of the function of a given PDE and can allow one to investigate the potential of that PDE as a therapeutic target.

However, given the difficulty of predicting transcriptional start sites and splice variants from primary genomic sequence data, it is still not known with exact certainty for any species how many different PDE mRNAs are transcribed. Furthermore, it also is not yet clear whether all transcript variants are present in all species.

Each PDE family is distinguished functionally by unique enzymatic characteristics and pharmacological profiles. In addition, each family exhibits distinct tissue, cell, and subcellular expression patterns (Beavo et al., Mol. Pharmacol. 46: 399-405, 1994; Soderling et al., Proc. Natl. Acad. Sci. USA 95: 8991-96, 1998; Fisher et al., Biochem. Biophys. Res. Commun. 246: 570-77, 1998; Hayashi et al., Biochem. Biophys. Res. Commun. 250: 751-56, 1998; Soderling et al., J. Biol. Chem. 273: 15553-58, 1998; Fisher et al., J. Biol. Chem. 273: 15559-64, 1998; Soderling et al., Proc. Natl. Acad. Sci. USA 96: 7071-76, 1999; Fawcett et al., Proc. Natl. Acad. Sci. USA 97: 3702-07, 2000; Boolell et al., Int. J. Impot. Res. 8: 47-52, 1996; Ballard et al., J. Urol. 159: 2164-71, 1998; Houslay, Semin. Cell Dev. Biol. 9: 161-67, 1998; and Torphy et al., Pulm. Pharmacol. Ther. 12: 131-35, 1999). Therefore, by administering a compound that selectively regulates the activity of one family or subfamily of PDE enzymes, it is possible to regulate cAMP and/or cGMP signal transduction pathways in a cell- or tissue-specific manner.

PDE11 is one of the most recently described families of PDEs; PDE11A has been identified (Fawcett et al., Proc. Natl. Acad. Sci. USA 97: 3702-07, 2000, hereinafter "Fawcett, 2000," Yuasa et al., J. Biol. Chem. 275: 31469-79, 2000, hereinafter "Yuasa, 2000"). While PDE11A is known to be expressed in, e.g., testis, skeletal muscle, kidney, liver, various glandular tissue (e.g., pituitary, salivary, adrenal, mammary, and thyroid), pancreas, spinal cord, and trachea (Fawcett, 2000), little is known about PDE11A function. The present invention provides biological tools to study PDE11A function and methods to identify agents that regulate PDE11A activity for use in treating diseases and conditions that are linked to these PDE11A functions.

Presently, little is known about the PDE11 enzymes beyond their biochemical characteristics and basic genetics. Four variants of PDE11A have been identified (PDE11A1-4). The longest variant, PDE11A4, has two N-terminal GAF domains, whereas the other variants are truncations of this variant of varying lengths. The drug tadalafil (an approved PDE5 inhibitor) is also a potent inhibitor of PDE11, thus there is significant evidence that pharmacological inhibition of PDE11 is not harmful to humans.

It is clear that the PDE11A variants demonstrate differential tissue expression. In humans, PDE11A1 mRNA is most prominent in skeletal muscle and prostate. PDE11A3 mRNA is found specifically in testis and PDE11A4 mRNA is highly expressed in prostate. PDE11A protein localization studies have been somewhat contradictory in their findings, probably because of differences in the specificity of the antibodies used. PDE11A1 protein was originally detected in prostate and skeletal muscle, although a later study did not detect PDE11A1 protein in any tissues. In fact, only PDE11A4 protein has been verified and is found in prostate, pituitary, heart, and liver. Another study suggested that PDE11A is widely expressed, and immunohistochemistry using an antibody reported to recognize all PDE11A variants localized it to the epithelial, endothelial, and smooth muscle cells of many tissues, but at highest levels in the prostate, testis, kidney, adrenal gland, colon, and skin. However, a separate study did not find any PDE11 protein expression in human testis. As with many PDEs, it is still not clear if the same tissue, cellular, and subcellular localization is found among species. PDE11 is highly expressed in the testis, prostate, and developing spermatozoa.

Relatively little is known about the function of PDE11A, in part due to the lack of selective PDE11 inhibitors. However, recent reports with a PDE11 knockout mouse model have been interpreted to suggest that PDE11 may be important for sperm development and function, as well as psychiatric diseases such as schizophrenia (PNAS, 2010; 107(8); 8457-62), while gene association studies link mutations in PDE11A with adrenocortical tumors and Cushing's Syndrome in which cortisol levels in the blood are elevated. As such, a small molecule inhibitor of PDE11 could, and does, increase cortisol synthesis providing a therapeutic route to for treating adrenal insufficiency and adrenal insufficiency associated diseases. The present invention is directed toward overcoming one or more of the problems discussed above.

SUMMARY OF THE INVENTION

The present invention generally relates to compositions comprising PDE11 inhibitor compounds, and their use in kits and methods for the treatment of low cortisol levels or adrenal insufficiency in a subject, and the treatment of diseases and disorders associated with adrenal insufficiency in a subject. In some embodiments, the composition is a pharmaceutical composition and comprises a pharmaceutically acceptable carrier.

The inventors have identified six structurally-diverse groups of compounds that are PDE11-inhibitors with IC50 values of <330 nM as judged by in vitro enzyme assays. Four groups are PDE11-selective as assessed using yeast-based growth assays, using human PDE11A as the gene from which target enzyme is produced, and in vitro enzyme assays. Two additional groups inhibit both PDE10 and PDE11 enzymes as judged by these assays. One of the PDE11-selective compounds of formula (I), BC11-38 along with two derivatives of it, effectively elevates cAMP levels and cortisol in a PDE11-specific manner in H295R adrenocortical cells. The ability to elevate cortisol could be therapeutically useful for the treatment of Addison's disease or other adrenal insufficiencies or in other situations where hydrocortisone is currently used. Accordingly, the PDE11 inhibitors of formulas (I) to (VI) as disclosed herein are therapeutically-preferable to the current practice of giving a subject exogenous cortisol (or hydrocortisone), which leads to a further loss of adrenal gland function.

In addition, PDE11 inhibitors have been reported to have the potential to restore chemosensitivity of chemo-resistant cancer cells as disclosed in PCT/US2005007791, now U.S. Pat. No. 7,888,047 (which is incorporated herein in its entirety by reference). Accordingly, the PDE11 inhibitors as disclosed herein are useful as an add-on to chemotherapeutic regimes, and the inventors have demonstrated effective induction of apoptosis of primary human leukemia cells in vitro.

In particular, the inventors herein have developed a fission yeast growth assay using a strain expressing the human PDE11A4 enzyme in which compounds that enhance the growth stimulation by exogenous cGMP are detected (inhibition of PDE11A allows an accumulation of cGMP in the cells to promote growth). In a screen of ~200,000 compounds, followed by a second screen of 595 hit compounds, the inventors identified 39 candidate small molecules that inhibit PDE11. The inventors reduced these to six candidate compounds by eliminating those compounds that show substantial activity against other PDE enzymes. The inventors then performed an analysis of cortisol production using H295R adrenocortical cells. A compound of formula (I) (e.g., BC11-38) produced a significant increase in both cAMP levels and cortisol production. A series of four derivatives of a compound of formula (I) were tested for the ability to inhibit PDE11 in an in vitro enzyme assay and for biological effects on H295R cells (cAMP elevation, cortisol elevation, and PKA-mediated ATF1 phosphorylation). These activities all demonstrated that the action of these compounds is through PDE11 inhibition.

Accordingly, one aspect of the present invention relates to compositions, methods and kits to elevate cAMP levels and cortisol production by adrenocortical cells in a subject. The compounds as disclosed herein belong to four structurally-distinct chemical classes and act by inhibiting the key cyclic nucleotide phosphodiesterase (PDE) in adrenocortical cells, PDE11. In doing so, the compounds as disclosed herein elevate cyclic AMP (cAMP) levels, that is the second messenger molecule in adrenocortical cells which leads to increased cortisol production.

When referring to selective PDE11 inhibitors as disclosed herein, the PDE11 inhibitors display IC50 values≤330 nM and >100-fold selectivity for PDE11 over other PDEs. There are other PDE11 inhibitors that are potent inhibitors but are not so selective or effective (see FIGS. 3B and 2C). The inventors demonstrated the effect of these compounds on human adrenocortical cells, where PDE11 is shown to regulate cortisol levels. One compound (e.g., BC11-38), along with its structural analogs, elevates cAMP levels and cortisol production through PDE11 inhibition, thus phenocopying the behavior of adrenocortical tumors associated with Cushing syndrome. In some embodiments, the compounds as disclosed herein can be used as research tools to study the biological function of PDE11, and can also serve as leads to develop therapeutic compounds for the treatment of adrenal insufficiencies.

As disclosed herein, compounds of formula (I), (II), (III), (IV), (V) and (IV) have been demonstrated to inhibit PDE11 via in vitro enzyme assays and yeast-growth-based assays. In some instances, the PDE11 inhibitor BC11-38 has been demonstrated to potently affect cAMP and cortisol levels in H295R cells, and the PDE11 inhibitor BC11-19 consistently elevates cAMP and cortisol, but to a lesser extent.

The inventors demonstrate that PDE11 inhibitor compound BC11-38 (a compound of formula (I)) stimulates cortisol production by adrenocortical cells and elevates cAMP levels in these cells. PDE11 inhibitor compounds BC11-15, BC11-19, and BC11-28 (compounds of formula (IV), (III), and (II) respectively) which are structurally distinct from BC11-38 were also demonstrated to be effective inhibitors of PDE11A to varying degrees. The inventors also demonstrate that BC11-38 and its derivatives and analogues produce a PDE11A-specific increase in phosphorylation of ATF1 and that the elevation in cortisol correlates with both the cAMP increase and the potency against PDE11 from the in vitro enzyme assays.

The inventors also demonstrate that HeLa cells, which do not express significant levels of PDE11A do not show the cAMP elevation in response to these compounds that is seen in H295 cells that have a high level of PDE11A activity. HeLa cells also do not show an increase in PKA-mediated CREB phosphorylation in response to BC11-38 treatment.

Accordingly, the present invention also relates to compounds of BC11-15, BC11-19, BC11-28 and BC11-38, and derivatives and analogues thereof as selective inhibitors of PDE11, and in particular, selective inhibitors of PDE11A, and their use in methods to increase cortisol production from adrenocortical cells, and/or elevating cortisol levels in a subject, for example a subject with adrenal insufficiency or an adrenal insufficiency associated disease or disorder as disclosed herein.

In some embodiments, the present invention also relates to the use of compounds of BC11-15, BC11-19, BC11-28 and BC11-38, and derivatives and analogues thereof in methods to elevate cortisol levels in a subject who has adrenal suppression, for example, where a subject is being treated with a corticosteroid, or on long-term corticosteroid treatment. In some embodiment, a subject who is on long-term corticosteroid treatment is administered a composition comprising at least one of any of compounds of BC11-15, BC11-19, BC11-28 and BC11-38. In some embodiments, a subject is administered a compound of formula (I) as disclosed herein, e.g., selected from any of the group of BC11-38, or analogues thereof such as, for example, BC-11-38-1, BC11-38-2, where the subject is also being administered a corticosteroid. The administration of a PDE11 inhibitor in the methods as disclosed herein can be concurrently with, prior to or after administration of a corticosteroid to the subject. In some embodiments, the corticosteroid is cortisone, prednisone or methylprednisolone or analogues or variants thereof. In some embodiments, the PDE11 inhibitor as disclosed herein is being administered in combination with a corticosteroid, e.g., in the same composition.

Accordingly, in some embodiments, the compounds as disclosed of BC11-15, BC11-19, BC11-28 and BC11-38, and derivatives and analogues thereof can be used in methods to maintain adrenal function for subjects undergoing long-term corticosteroid treatment. Long-term corticosteroid treatment can be administration of a corticosteroid to a subject for any time period longer than 1 week, or longer than 2 weeks, or longer than 3 weeks or more than three weeks.

In some embodiments, the compounds of BC11-15, BC11-19, BC11-28 and BC11-38, and derivatives and analogues thereof can be used in methods of treatment of inflammation, and function as an anti-inflammatory compound, as well as in methods for the treatment of psychiatric disorders such as schizophrenia, or treatment of cancer, e.g., as adjuvant therapy for treatment of cancer, e.g., to restore chemosensitivity to otherwise chemoresistant cancer cells.

To increase the likelihood of the successful development of safe and effective PDE11 inhibitors to treat low cortisol production and/or adrenal insufficiency, it is desirable to have structurally-distinct compounds that can be optimized so as to reduce the chance of a deleterious off-target effect by any one candidate therapeutic.

Cortisol elevation can be used to treat Addison's Disease and other adrenal insufficiencies. The present invention using PDE11 inhibitor compounds of formula (I)-(VI) has advantages over administration of exogenous (e.g., topical) cortisol (such as hydrocortisone) in that the PDE11 inhibitor compounds stimulate cortisol production by the subject rather than introducing cortisol by a foreign route, as the latter practice (introducing exogenous cortisol) has negative consequences as it triggers a feedback mechanism to block cortisol production by the subject.

Additionally, there is also evidence that long-term cortisol treatment impairs memory. Accordingly, the present invention directed to use of PDE11 inhibitors of formula (I)-(VI) as disclosed herein would be unlikely to have the type of side-effects associated with exogenous cortisol treatment, as their use in a method or therapy simply restores normal cortisol production rather than one that involves significantly elevated exposure to exogenous cortisol.

Accordingly, due to the negative feedback mechanisms, subjects on long-term cortisol treatment, e.g., long-term corticosteroid treatment can have adrenal suppression in which the adrenal gland produces insufficient amount of cortisol and other adrenal steroids upon cessation of the corticosteroid treatment. Complications of adrenal suppression include, but are not limited to, acute lymphoblastic leukemia, cataracts, Cushing's syndrome, glaucoma, diabetes and osteoporosis, swelling of the face, mental confusion, high blood sugar which can trigger and/or worsen diabetes, increased risk of infections, loss of calcium from bones which can lead to osteoporosis and fractures, menstrual irregularities, suppressed adrenal gland hormone production, and thin skin leading to easy bruising and/or slower wound healing. Accordingly, in some embodiments, the present invention encompasses method of administering at least one PDE11 inhibitor compound of formula (I)-(VI), such as compound of formula (I) to a subject who is being undergoing long-term corticosteroid treatment.

In some embodiments, the methods as disclosed herein encompass use of and/or administration of a PDE11 inhibitor compounds of formula (I)-(VI) as disclosed herein for the treatment of an inflammatory condition where hydrocortisone is normally used. Without wishing to be bound by theory, hydrocortisone is commonly used to achieve prompt suppression of inflammation in many inflammatory and allergic conditions). Examples of inflammatory conditions include rheumatoid arthritis, systemic lupus, acute gouty arthritis, psoriatic arthritis, ulcerative colitis, and Crohn's disease. Severe allergic conditions that fail conventional treatment may also respond to hydrocortisone. Examples include bronchial asthma, allergic rhinitis, drug-induced dermatitis, and contact and atopic dermatitis. Chronic skin conditions treated with hydrocortisone include dermatitis herpetiformis, pemphigus, severe psoriasis and severe seborrheic dermatitis. Chronic allergic and inflammatory conditions of the uvea, iris, conjunctiva and optic nerves of the eyes are also treated with hydrocortisone.

Hydrocortisone is also used in the treatment of blood cell cancers (leukemias), and lymph gland cancers (lymphomas). Blood diseases involving destruction of platelets by the body's own immune cells (idiopathic thrombocytopenia purpura), and destruction of red blood cells by immune cells (autoimmune hemolytic anemia) can also be treated with hydrocortisone. Other miscellaneous conditions treated with this medication include thyroiditis and sarcoidosis. Finally, hydrocortisone is used as a hormone replacement in patients whose adrenal glands are unable to produce sufficient amounts of corticosteroids.).

Thus, the present invention has advantages of reducing side effects associated with administration of exogenous cortisol, which include but are not limited to less severe side effects include dryness, itching, burning and mild skin irritation at the side of treatment (for topic applications), or more serious side effects such as severe allergic reactions, swelling, loss of hearing, weight gain, muscle weakness, symptoms of high blood sugar, confusion, unusual drowsiness, rectal pain and bleeding, mental or mood changes, chest pain, easy bruising or bleeding; and vision changes. More severe side effects of hydrocortisone treatment also include, for example, but not limited to hypothalamus-pituitary-adrenal activity suppression, impotence, menstrual irregularities, peptic ulcer disease, cataracts, myopathy, osteoporosis, vertebral compression fractures, hypertension, congestive heart failure, decreased glucose tolerance and hyperglycemia resulting in diabetes-like symptoms, nausea and vomiting, peptic ulcer disease, pancreatitis, increased susceptibility to infections, thrombocytopenia, and seizures.

Disclosed herein are highly-effective PDE11 inhibitors including small molecule inhibitors such as selective PDE11 inhibitors with at least one of the following characteristics: 1) desired activity and selectivity profile to inhibition of PDE11 enzyme relative to other PDEs; 2) desired potency to increase cortisol production in ex vivo assays and adrenocortical cells; 3) favorable cytotoxicity profile; 4) favorable physicochemical properties such as solubility and permeability; and 5) favorable oral pharmacokinetic (PK) properties (plasma exposure, half-life, biodistribution, oral bioavailability and CNS penetration).

Another aspect of the present invention relates to a method of treatment of low cortisol levels and/or adrenal insufficiency in a subject by administering a composition comprising one or more PDE11 and/or dual PDE11/10 inhibitors such as the PDE11/PDE10 compounds as disclosed herein. In some embodiments, the subject is a human.

Typically, a subject with adrenal insufficiency or low cortisol levels is amenable to treatment according to the methods as disclosed herein. Additional aspects of the present invention also relate to methods to increase cortisol production in a subject, for example, a subject with low cortisol levels. Other aspects of the present invention relate to a method for the treatment of a subject with adrenal insufficiency or a disease or disorder associated with adrenal insufficiency, for example, but not limited to, Addison's disease, congenital adrenal hyperplasia, or a subject who has undergone removal of part, or a whole adrenal gland for example, after adrenocortical tumor or cancer, or where the subject has previously, or is undergoing radiation therapy for an adrenocortical tumor, or a subject has one or more symptoms of a low-cortisol associated disease such as, but not limited to; inflammation, inflammatory skin conditions, autoimmune diseases, allergic diseases and hypoadrenia. Other aspects of the present invention relate to a method for the treatment of a subject with a disease or disorder associated with low cortisol production, which includes without limitation, Addison's disease or hypocortisolism, and it occurs in all ages, affects both sexes and can be life-threatening, Primary adrenal insufficiency, or Addison's disease, or acquired immune deficiency syndrome (AIDS), or secondary adrenal insufficiency.

Another aspect of the present invention relates to kits comprising the compositions as disclosed herein, for example, for use in methods for the treatment of low cortisol in a subject, or for the treatment of adrenal insufficiency or associated diseases and disorders. In some embodiments, the kit further comprises instructions for use.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A shows screening strains possess the fbp1-ura4 reporter, whose expression is repressed by PKA due to cGMP added to the growth medium. PDE11 hydrolysis of cGMP allows ura4 expression, producing a $5FOA^S$ phenotype (top panel). PDE11 inhibition elevates intracellular cGMP levels to confer $5FOA^R$ growth (bottom panel). FIG. 1B shows 5FOA growth assays with strains lacking PDE activity (cgs2-2 is a frameshift allele of the only S. pombe PDE gene; (35)) (squares) or expressing human PDE11A4 (circles) were performed in 0-2 mMcGMP. FIG. 1C shows 5FOA growth assays with a strain expressing human PDE11A4 in medium containing either 0.2% DMSO (circles) or 25 µM BC76 (squares), with varying concentrations of cGMP (0-0.2 mM). The vertical line indicates the cGMP concentration that produces the maximum difference in average OD between the DMSO-treated and BC76-treated cultures. Values are the mean of three experiments (with three wells per condition in each experiment) ±S.E.M.

FIG. 2A shows scatter plot represents Z scores for duplicate wells pinned with 0.2% DMSO (negative controls; gray circles), 25 µM BC76 (positive controls; white circles), or screening compounds (black circles). FIG. 2B shows composite Z score distribution of the screened compounds. The height of each bar represents the number of screened compounds displaying the corresponding Composite Z score in the x-axis. The x-axis is binned into 537 bins with intervals of 0.4. Compounds with Composite Z scores >20 are defined as hits.

FIGS. 3A-3C show four potent and selective PDE11 inhibitors identified by the HTS. FIG. 3A shows an overview of the steps following the initial screen. Compounds detected as hits in previous PDE8, PDE4, and PDE7 screens were eliminated from the 1143 hits in the primary screen, as indicated in the pie chart. Br-cAMP, in the biologically active compound library, was also a hit as expected and excluded. The strongest 595 remaining PDE11 hits (cherry-picks) were rescreened using PDE11, PDE5, and PDE10-expressing strains. 99 compounds were confirmed to be PDE11-selective candidates and 39 of them were tested in secondary assays that led to the identification of four PDE11-specific inhibitors. FIG. 3B shows the profiling of PDE11-specific inhibitors in yeast growth assays. Four PDE11-selective inhibitors were profiled using strains expressing 10 of the 11 PDE families. Dose-response growth curves from one representative (with duplicate wells for each data point) of triplicate experiments are presented. FIG. 3C shows the structures and $IC_{50}$ values of PDE11-specific inhibitors in in vitro enzyme assays. All PDEs in the study, except for PDE6, can be inhibited by other compounds in our collection with $IC_{50}$ values<2 µM.

FIG. 4A shows cAMP levels of H295R cells following a 2 h treatment with PDE11-specific inhibitors (20 µM) in the absence or presence of 10 µM forskolin. The nonselective PDE inhibitor IBMX was used at 500 µM as a positive control. FIG. 4B shows cortisol release by H295R cells following a 24 h treatment with PDE11-specific inhibitors (20 µM) or IBMX (500 µM) in the presence of 10 µM forskolin. Data are presented as % of forskolin+DMSO treated cells. Values represent the averages of at least two independent experiments for each assay performed in duplicate ±S.E.M. (*p<0.05, **p<0.01).

FIGS. 5A-5E show the biological activities of BC11-38 and derivatives correlate with their potency for PDE11 inhibition. FIG. 5A shows the structures and $IC_{50}$ values of BC11-38 derivatives in in vitro enzyme assays. FIG. 5B shows cAMP levels (left) and ATF-1 phosphorylation (right) in H295R adrenocortical cells following a 2 h treatment with BC11-38 and derivatives (20 μM) in the presence of 10 μM forskolin. Cells were lysed and proteins were subjected to immunoblotting with a p-CREB/ATF-1 antibody. FIG. 5C shows cortisol release by H295R cells following a 24 h treatment with BC11-38 and derivatives (20 μM) or IBMX (500 μM) in the presence of 10 μM forskolin. Data are presented as % of forskolin+DMSO treated cells. FIG. 5D shows quantitative RT-PCR for PDE11 mRNA in various cell lines. PDE11 expression was normalized to the expression level of the RPLP0 reference gene. FIG. 5E shows BC11-38 and related compounds do not increase cAMP levels or CREB phosphorylation in HeLa cells. Compound treatment, cAMP assays, and immunoblots were performed as described for H295R cells. Values represent the averages of three separate experiments for each assay performed in duplicate ±S.E.M. (*p<0.05, **p<0.01).

FIGS. 7A-7B show the classification of hits based on Composite Z score in the HTS. FIG. 7A shows the composite Z scores (y-axis) of screened compounds grouped by compound plates along the x-axis (each point represents one compound, each vertical column represents one compound plate). FIG. 7B shows a scatter plot for Z scores of screened compounds. Values for each of the two replicates are plotted on the x- and y-axis. Strong hits (blue), moderate hits (red), and weak hits (yellow). Compounds with Composite Z score >35 were defined as strong, 26-35 were defined as moderate, and 20-26 were defined as weak hits. By these criteria, 0.2%, 0.15% and 0.2% of the compounds screened were identified as strong, moderate, and weak hits, respectively.

FIG. 8A-8B shows results from Cherry-picking experiments for validation and counter-selection of primary screen hits in strains expressing PDE11, PDE5, and PDE10. FIG. 8A are heatmaps representing the cherry-picking experiment plates. 595 compounds were each pinned into 3 plates for PDE11 (top), PDE10 (middle), and PDE5 (bottom)-expressing strains (in rows C-N, columns 3-22 in plates 1&2 and columns 3-12 in plate 3). The last column of each plate was pinned with positive control (rows A-H) (25 μM BC76, which inhibits all of the PDEs in the experiment), and negative control (rows I-P) (0.2% DMSO). The colors represent the optical density, with dark red reflecting higher growth. FIG. 8B shows the optical densities of PDE5-expressing strain plotted against those of the PDE11-expressing strain. FIG. 8C shows the optical densities of PDE10-expressing strain plotted against those of the PDE11-expressing strain. Compounds that produced an optical density >0.167 for the PDE11 strain were validated as PDE11 hits. Compounds that produced optical density >0.2 for the PDE5 strain in FIG. 8B were defined as PDE5 hits, and >0.195 for the PDE10 strain in FIG. 8C were defined as PDE10 hits. Compounds that stimulated growth of the PDE5- and/or PDE10-expressing strain were eliminated for being nonselective.

DETAILED DESCRIPTION OF THE INVENTION

Figure 1A:
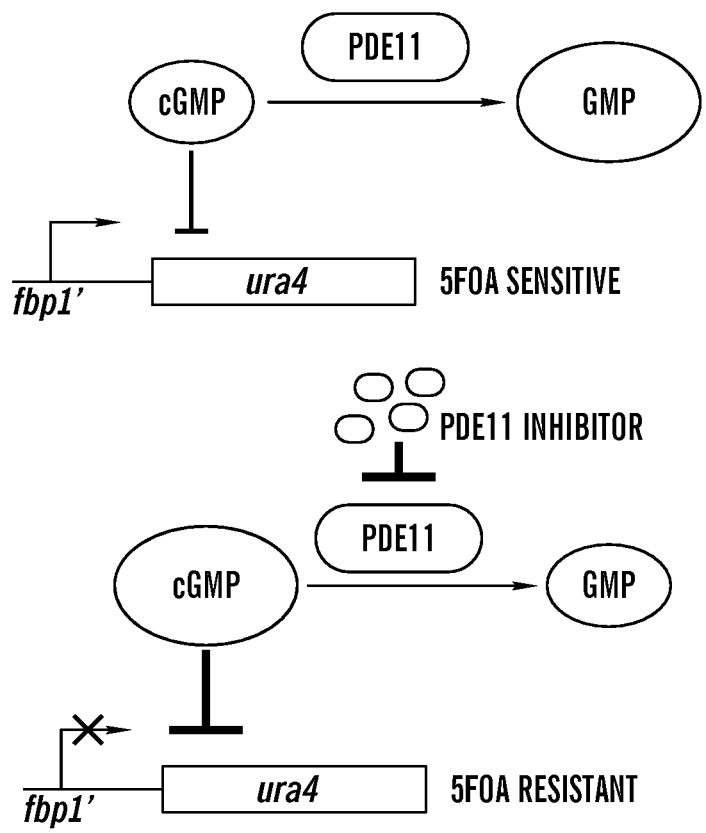
FIGS. 1A-1C show optimization of growth assay to identify PDE11 inhibitors.

Other aspects of the present invention relate the use of PDE11 inhibitors, including selective PDE11 inhibitors or dual PDE11/PDE10 inhibitors such as the PDE11 or PDE11/PDE10 inhibitors as disclosed herein, in a method for treating a wide variety of low cortisol disorders and/or adrenal insufficiencies, for example, a disorder or disease in which the subject has low cortisol levels, or has reduced level of cortisol production. In some embodiments, the PDE11 inhibitors as disclosed herein can be used in a method to elevate cortisol production by adrenocortical cells. In some embodiments, a method to increase cortisol levels, or to treat an adrenal insufficiency disease or disorder or to increase adrenal cortisol production uses a combination of a PDE11 inhibitor or a dual PDE11/PDE10 inhibitor or a combination of a PDE11 inhibitor with a dual PDE11/PDE10 inhibitor.

The present invention also relates to a group of compounds that are selective PDE11 inhibitors that are selective for inhibition of the PDE11 enzyme. In some embodiments, a PDE11 inhibitor as disclosed herein is also selective for inhibition of another PDE enzyme, e.g., a PDE11 inhibitor is a dual PDE11 inhibitor (herein referred to as a "PDE11/PDE" inhibitor), for example, where the PDE11 inhibitor molecule is selective for inhibition of PDE11 and a second PDE inhibitor, for example but not limited to, a PDE10, or PDE5, PDE8 or the like. In some embodiments, a dual PDE11/PDE inhibitor also inhibits PDE10, and is a PDE11/PDE10 inhibitor as disclosed herein.

Also described herein are compounds and compositions comprising at least one of (i) PDE11 inhibitor (e.g., a PDE11A inhibitor); or at least one dual PDE11/PDE inhibitor, or a combination of one or more such inhibitors. In some embodiments, a composition may comprise a pharmaceutically acceptable carrier.

In some embodiments, the present invention relates to methods for using compounds of formula (I)-(VI), e.g., compounds BC11-15, BC11-19, BC11-28 and BC11-38, and derivatives and analogues thereof, in methods to maintain adrenal function for subjects undergoing long-term corticosteroid treatment.

Other aspects of the present invention relate to methods for increasing cortisol levels in a subject and methods for treating disorders and diseases associated with low cortisol levels in a subject, by administering a PDE11 inhibitor of formula (I)-(VI) as disclosed herein, as well as related kits for the above-described therapeutic uses.

Other aspects of the present invention relate to methods for increasing adrenal cortisol levels in a subject and methods for treating adrenal insufficiency and disorders and diseases associated with adrenal insufficiency, for example disease or disorders resulting from a complete or partial loss of function of the adrenal gland in a subject, by administering a PDE11 inhibitor, as well as related kits for the above-described therapeutic uses.

One aspect of the present invention provides a method to treat a subject to increase cortisol levels in a subject, comprising administering a therapeutically effective amount of a phosphodiesterase 11 (PDE11) antagonist, e.g., a compound of Formula (I)-(VI) as disclosed herein. In another embodiment, the method further comprises administering an additional therapeutic agent, such as, a PDE4 inhibitor (e.g., ROLIPRAM™) that produce the cAMP response in adrenal cells.

Another aspect of the present invention relates to kits comprising a PDE11 inhibitor as disclosed herein, and instructions for administering the PDE11 inhibitor to a subject for the treatment of low cortisol levels and/or adrenal insufficiency in the subject, or to treat a disease or disorder associated with adrenal insufficiency for the treatment of low cortisol levels, or for the treatment to increase the cortisol levels, such as to increase cortisol levels in a subject with Addison's disease, congenital adrenal hyperplasia, or any disorder where the subject is normally administered hydrocortisone, e.g., in the treatment of blood cell cancers (leukemias), and lymph gland cancers (lymphomas), blood diseases involving destruction of platelets by the body's own immune cells (idiopathic thrombocytopenia purpura), and destruction of red blood cells by immune cells (autoimmune hemolytic anemia) can also be treated with hydrocortisone. Other miscellaneous conditions treated with hydrocortisone include thyroiditis and sarcoidosis. Finally, hydrocortisone is used as a hormone replacement in patients whose adrenal glands are unable to produce sufficient amounts of corticosteroids.).

Other aspects of the present invention relate to kits comprising a PDE11 inhibitor as disclosed herein, and instructions for administering a PDE11 inhibitor to a subject for the treatment to subjects with low cortisol levels and/or adrenal insufficiency in a subject, or to treat a disease or disorder associated with adrenal insufficiency, or for the treatment to increase cortisol production from adrenocortical cells in a subject.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

The term "PDE11" as used herein, refers to the amino acid sequences of substantially purified PDE11 obtained from any species, particularly mammalian, including bovine, ovine, porcine, murine, equine, and preferably human, from any source whether natural, synthetic, semi-synthetic, or recombinant. PDE11 also encompasses all members of the PDE11 family, including without limitation, PDE11A, PDE11A1, PDE11A2, PDE11A3, and PDE11A4 family of cyclic nucleotide phosphodiesterases.

The term "PDE10" as used herein, refers to the amino acid sequences of substantially purified PDE10 obtained from any species, particularly mammalian, including bovine, ovine, porcine, murine, equine, and preferably human, from any source whether natural, synthetic, semi-synthetic, or recombinant. PDE10 also encompasses all members of the PDE10 family of cyclic nucleotide phosphodiesterases.

The term "antagonist" or "inhibitor", as used herein in reference to a PDE11 antagonist or inhibitor, refers to a molecule which, when bound to PDE11, decreases the amount or the duration of the effect of the biological or immunological activity of PDE11. Antagonists may include proteins, nucleic acids, carbohydrates, antibodies or any other molecules that decrease the effect of PDE11.

The term "PDE11 inhibitor" or "PDE11 antagonist" as used herein refers to an agent that reduces or attenuates the biological activity of the PDE11 polypeptide in a cell, either by decreasing the activity of the PDE11 polypeptide or by effectively reducing the amount of PDE11 polypeptide in a cell or by decreasing the enzymatic activity of the PDE11 polypeptide. Compounds that are PDE11 inhibitors include all solvates, hydrates, pharmaceutically acceptable salts, tautomers, stereoisomers, and prodrugs of the compounds.

The term a "selective" PDE11 inhibitor as used herein refers to an agent that inhibits PDE11 activity with a Ki at least 10-fold less, at least 20-fold less, at least 25-fold less, at least 35-fold less, at least 50-fold less, at least 60-fold less, at least 75-fold less, at least 85-fold less, at least 90-fold less, at least 95-fold less, or preferably, at least 100-fold less, than the Ki for inhibition of one or more PDE's.

The term "decreased PDE11 activity" means a substantial decrease by a statistically significant amount in the total PDE11 polypeptide activity of the PDE11 enzyme as a result of inhibition with a PDE11 inhibitor or dual PDE11/PDE inhibitor compound, such as PDE11/PDE10 as disclosed herein as compared to in the absence of such inhibitor. These dual inhibitors are at least about least 10-fold, at least 20-fold, at least 25-fold, at least 35-fold, at least 50-fold, at least 60-fold, at least 75-fold, more selective to the PDEs than the other PDE enzymes.

The term "biologically active", as used herein, refers to a protein having structural, regulatory, or biochemical functions of a naturally occurring molecule, and displays the activity of the molecule in a cellular and/or in vivo assay.

The term "isomer" as used herein refers to a compound with the same molecular formula but different structural formulas. Isomers do not necessarily share similar properties, unless they also have the same functional groups. There are many different classes of isomers, like stereoisomers, enantiomers, geometrical isomers, etc. There are two main forms of isomerism: structural isomerism and stereoisomerism (spatial isomerism).

The designations "R" and "S" are used to denote the absolute configuration of a molecule about its chiral center. The designations may appear as a prefix or as a suffix; they may or may not be separated from the isomer by a hyphen; they may or may not be hyphenated; and they may or may not be surrounded by parentheses.

The term "S isomer" as used herein refers to an enantiomer with the chiral center S according to a system by which its substituents are each assigned a priority, according to the Cahn-Ingold-Prelog priority rules (CIP), based on atomic number, where the priority of atomic number decreases in counterclockwise direction, it is S enantiomer (from the Latin Sinestra, meaning "left"). Without wishing to be limited to theory, if the center is oriented so that the lowest-priority of the four is pointed away from a viewer, the viewer will then see two possibilities: If the priority of the remaining three substituents decreases in clockwise direction, it is labeled R (from the Latin Rectus, meaning "right"), if it decreases in counterclockwise direction, it is S (from the Latin Sinestra, meaning "left").

The term "cortisol" as used herein is also referred to in the art as hydrocortisone, and refers to a steroid hormone or glucocorticoid, produced by the adrenal gland, and is released in response to stress and a low level of blood glucocorticoids.

The term "treating", as used herein, refers to altering the disease course of the subject being treated. Therapeutic effects of treatment include, without limitation, preventing occurrence or recurrence of disease, alleviation of symptom(s), diminishment of direct or indirect pathological consequences of the disease, decreasing the rate of disease progression, amelioration or palliation of the disease state, and remission or improved prognosis. In some embodiments, treating includes an increase in the level of cortisol in a subject, and/or an increase in the production of cortisol from adrenocortical cells in the subject. In some embodiments, treatment can be prophylactic treatment, for example, treatment of low cortisol levels, or for prevention of adrenal insufficiency or related diseases as disclosed herein.

The term "pharmaceutically acceptable excipient", as used herein, refers to carriers and vehicles that are compatible with the active ingredient (for example, a compound of the invention) of a pharmaceutical composition of the invention (and preferably capable of stabilizing it) and not deleterious to the subject to be treated. For example, solubilizing agents that form specific, more soluble complexes with the compounds of the invention can be utilized as pharmaceutical excipients for delivery of the compounds. Suitable carriers and vehicles are known to those of extraordinary skill in the art. The term "excipient" as used herein will encompass all such carriers, adjuvants, diluents, solvents, or other inactive additives. Suitable pharmaceutically acceptable excipients include, but are not limited to, water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical compositions of the invention can also be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like, which do not deleteriously react with the active compounds of the invention.

The terms "salts" and "pharmaceutically acceptable salts" refer to organic and inorganic salts of a compound, a stereoisomer of a compound, or a prodrug of a compound as disclosed herein. Thus, as used herein, the term "pharmaceutically acceptable salt," is a salt formed from an acid and a basic group of a compound of the invention. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate salts.

The term "pharmaceutically acceptable salt" also refers to a salt prepared from a compound as disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. Other pharmaceutically acceptable salts are described in the Handbook of Pharmaceutical Salts. Properties, Selection, and Use (P. Heinrich Stahl and C. Wermuth, Eds., Verlag Helvetica Chica Acta, Zurich, Switzerland (2002)).

The term "subject" as used herein refers to a vertebrate, preferably a mammal, more preferably a primate, still more preferably a human. Mammals include, without limitation, humans, primates, wild animals, feral animals, farm animals, sports animals, and pets. In some embodiment, a subject includes domestic and commercial farm animal, for example, but not limited to, cattle, pigs, horses and other commercial animals. In some embodiments, a subject is a male subject, however, subjects also include female subjects as well as subjects who are transgendered female to male subjects. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. A patient or subject includes any subset of the foregoing, e.g., all of the above. In certain embodiments of the aspects described herein, the subject is a mammal, e.g., a primate, e.g., a human. The terms, "patient" and "subject" are used interchangeably herein. In addition, the methods and compositions described herein can be used to treat domesticated animals and/or pets.

The term "neonate" refers to a subject of ages 0-6 months, inclusive.

The term "infant" refers to a subject who is 6 months to two years of age and is inclusive of babies and toddlers. In some embodiments, an infant can include any subject under 2 years of age.

The term "child" refers to a subject who is under 18 years of age. In some embodiments, a child includes neonates and infants. In some embodiments, a child is a subject between the ages two years of age and 18 years of age.

In some embodiments, a subject can be one who has been diagnosed with, or identified as has having a low cortisol levels as determined by one of ordinary skill in the art and as disclosed herein, or a subject who is currently being treated for low cortisol levels, and/or adrenal insufficiency and/or is being treated with hydrocortisone. In some embodiments of the aspects described herein, the method further comprising diagnosing a subject with low cortisol levels and/or adrenal insufficiency by the methods as disclosed herein before beginning treatment with a method described herein. Methods of diagnosing low cortisol levels and/or adrenal insufficiency in a subject are well known in the art, and are described herein. In some embodiments, the method of treatment further comprises selecting a subject who has been identified or diagnosed with a low cortisol level and/or adrenal insufficiency before beginning treatment with a PDE11 inhibitor as disclosed herein according to the kits and methods as described herein.

The term "prodrug" refers to a compound that formulated as a precursor compound that, following administration, activates or releases the active component of the compound in vivo via a chemical or physiological process (e.g., upon being brought to physiological pH or through enzyme activity). A discussion of the synthesis and use of prodrugs is provided by Higuchi and Stella, Prodrugs as Novel Delivery Systems, vol. 14 of the ACS Symposium Series, and Bioreversible Carriers in Drug Design, ed. Edward B. Roche, American Pharmaceutical Association and Pergamon Press, 1987. Accordingly, the term "prodrug" refers to compounds that can be converted via some chemical or physiological process (e.g., enzymatic processes and metabolic hydrolysis) to an inactive form that can be activated in vivo by some co-compound or a specific environmental condition, e.g., pH etc. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject.

The term "therapeutically effective amount" as used herein refers to an amount sufficient to effect a beneficial or desired clinical result upon treatment. Specifically, the term "therapeutically effective amount" means an amount of a compound of this invention sufficient to measurably (i) increase the production of cortisol from adrenocortical cells from the subject, and/or (ii) increase the level of cortisol in a subject by a statistically significant level as compared to in the absence of a compound (iii) or using a cell-based assay as disclosed herein that increases the growth of fission yeast in 5FOA media expressing PDE11 after 48 hrs of incubation, and/or (iv) cause a measurable improvement in an animal model of a low cortisol levels, or adrenal insufficiency, for example, increase cortisol levels in adrenocortical dysplasia (acd) mouse, which is a model for human congenital adrenal hypoplasia, and adrenal insufficiency. Therapeutically effective amounts will vary, as recognized by those skilled in the art, depending on the specific disease treated, the route of administration, the excipient selected, and the possibility of combination therapy.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. Furthermore, therapeutically effective amounts will vary, as recognized by those skilled in the art, depending on the specific disease treated, the route of administration, the excipient selected, and the possibility of combination therapy.

A physiological effects of a compound as disclosed herein on the subject can be measured to determine the therapeutically effective amount include, without limitation, levels of cortisol in the plasma and/or urine in a subject and the like. Relevant assays to measure levels of cortisol in the plasma and blood include, with limitation, Western (immuno)blot, RT-PCR, expression profile by microarray or other technology, high-content immunofluorescence, cytoblot, mass spectrometry.

As used herein, the terms "alkyl," "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopentyl, cyclohexyl, cyclopropylmethyl, adamantly, norbornane, and norbornene. This is also true of groups that include the prefix "alkyl-," such as alkylcarboxylic acid, alkyl alcohol, alkylcarboxylate, alkylaryl, and the like. Examples of suitable alkylcarboxylic acid groups are methylcarboxylic acid, ethylcarboxylic acid, and the like. Examples of suitable alkylacohols are methylalcohol, ethylalcohol, isopropylalcohol, 2-methylpropan-1-ol, and the like. Examples of suitable alkylcarboxylates are methylcarboxylate, ethylcarboxylate, and the like. Examples of suitable alkyl aryl groups are benzyl, phenylpropyl, and the like.

These may be straight chain or branched, saturated or unsaturated aliphatic hydrocarbon, which may be optionally inserted with N, O, or S. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like.

As used herein, the term "alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

As used herein, the term "alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, thiazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The aryl, and heteroaryl groups can be unsubstituted or substituted by one or more substituents independently selected from the group consisting of alkyl, alkoxy, methylenedioxy, ethylenedioxy, alkylthio, haloalkyl, haoalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonythio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, arylcarbonylaminoalkyl, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If other groups are described as being "substituted" or "optionally substituted," then those groups can also be substituted by one or more of the above enumerated substituents.

The term "arylalkyl," as used herein, refers to a group comprising an aryl group attached to the parent molecular moiety through an alkyl group.

The term "carbonyl," as used herein, refers to "C(=O)".

As used herein, the term "cyclyl" refers to a nonaromatic 5-8 membered monocyclic, 8-12 membered bicyclic, or 11-14 membered tricyclic ring system, which can be saturated or partially unsaturated. Representative saturated cyclyl groups include, but are not limited to, cyclopropyl, cyclobutyl, cyclopentyl, cyclopentenyl, cyclohexyl, cyclohexenyl, cycloheptyl, cyclooctyl, and the like; while unsaturated cyclyl groups include cyclopentenyl and cyclohexenyl, and the like.

As used herein, the term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, As used herein, the term "aryl" refers to an aromatic 5-8 membered monocyclic, 8-12 membered bicyclic, or 11-14 membered tricyclic ring system. Examples of aryl groups include phenyl, naphthyl and the like.

As used herein, the term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, thiazolyl, benzimidazolyl, pyrimidinyl, thiophenyl or thienyl, quinolinyl, indolyl, oxazolyl, and the like.

As used herein, the term "halogen" refers to iodine, bromine, chlorine, and fluorine.

As used herein, the terms "optionally substituted alkyl," "optionally substituted cyclyl," "optionally substituted heterocyclyl," "optionally substituted aryl," and "optionally substituted heteroaryl" means that, when substituted, at least one hydrogen atom in said alkyl, cyclyl, heterocylcyl, aryl, or heteroaryl is replaced with a substituent. In the case of an oxo substituent (=O) two hydrogen atoms are replaced. In this regard, substituents include oxo, halogen, alkyl, cyclyl, heterocyclyl, aryl, heteroaryl, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, SO$_n$R$^x$ and —SO$_n$NR$^x$R$^y$, wherein n is 0, 1 or 2, R$^x$ and R$^y$ are the same or different and independently hydrogen, alkyl, cyclyl, heterocyclyl, aryl or heterocycle, and each of said alkyl, cyclyl, heterocyclyl, aryl and heterocycle substituents may be further substituted with one or more of oxo, halogen, —OH, —CN, alkyl, —OR$^x$, heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

The terms "acyl," "carboxyl group," or "carbonyl group" are recognized in the art and can include such moieties as can be represented by the general formula:

wherein W is OR$^w$, N(R$^w$)$_2$, SR$^w$, or R$^w$, R$^w$ being hydrogen, alkyl, heteroalkyl, alkenyl, heteroalkenyl, alkynyl, heteroalkynyl, aryl, heteroaryl, heterocycle, substituted derivatives thereof, or a salt thereof. For example, when W is O-alkyl, the formula represents an "ester," and when W is OH, the formula represents a "carboxylic acid." When W is alkyl, the formula represents a "ketone" group, and when W is hydrogen, the formula represents an "aldehyde" group. Those of ordinary skill in the art will understand the use of such terms.

The terms "heterocycle" and "heterocyclic group" are recognized in the art and refer to 3- to about 10-membered ring structures, such as 3- to about 7-membered rings, whose ring structures include one to four heteroatoms. The heterocycle may include portions which are saturated or unsaturated. In some embodiments, the heterocycle may include two or more rings (e.g., cycloalkyls, cycloalkenyls, cycloalkynyls, aryls and/or heterocyclyls) in which two or more carbons are common to two adjoining rings, e.g., the rings are "fused rings." In some embodiments, the heterocycle may be a "bridged" ring, where rings are joined through non-adjacent atoms, e.g., three or more atoms are common to both rings. Each of the rings of the heterocycle may be optionally substituted. Examples of heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with substituents including, for example, halogen, aryl, heteroaryl, alkyl, heteroalkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, CF$_3$, CN, or the like.

As used herein, the term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and cannot be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic, fused, and bridged substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

According to some aspects of the invention, the PDE11 and/or dual PDE11/PDE inhibitors described herein include compounds having similar bioactivity as those represented by any one of the formulas of (I), (II) or (III), but with different chemotypes. Such compounds can be identified by scaffold hopping. The aim of scaffold hopping is to identify isofunctional molecular structures that have the same bioactivity but significantly different molecular backbones. Several methods of scaffold hopping are available and known to one of skill in the art. These include FEPOPS, DAYLIGHT, MACS and Pipeline Pilot fingerprints.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level (e.g., in the absence of a compound of the invention).

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level (e.g., in the absence of a compound of the invention).

The term "statistically significant" or "significantly" refers to statistical significance and generally means at least two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

The term "substantially" as used herein means a proportion of at least about 60%, or preferably at least about 70% or at least about 80%, or at least about 90%, at least about 95%, at least about 97% or at least about 99% or more, or any integer between 70% and 100%.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and the include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

In General:
Phosphodiesterase 11 (PDE1)

Without wishing to be bound by theory, the family of PDE11 nucleotide phosphodiesterases include isoforms, which include without limitation, PDE11A, PDE11A1, PDE11A2, PDE11A3, and PDE11A4 family of cyclic nucleotide phosphodiesterases.

The human PDE11A protein is 489 amino acids in length and has amino acid sequence shown in GenBank Accession No. NM_001077196, and encodes a 56-kDa protein. There are 4 isoforms of PDE11A exist (PDE11A1-PDE11A4), where the PDE11A variant PDE11A1 has a distinct 5'UTR and lacks an in-frame portion of the 5'coding region as compared to PDE11A4. Accordingly, PDE11A1 has a shorter N-terminus as compared to PDE11A4. The human PDE11A4 protein is 933 amino acids in length and has amino acid sequence shown in GenBank Accession No. NP_058649.3 and encodes a 104.8 kDa protein.

Exemplary PDE11 Inhibitors

As disclosed herein are exemplary PDE11 inhibitors of formula (I), (II), (III) and (IV) are disclosed.

In some embodiment, a PDE11 inhibitor compound as disclosed herein is a compound of formula (I):

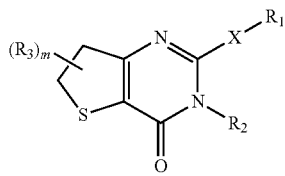

I wherein
X is O, $NR_4$, S or absent;
$R_1$ and $R_2$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2 R^B$; -; —CN; —SCN; —S$R^B$; —SO$R^B$; —SO$_2 R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

each $R_3$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2 R^B$; -; —CN; —SCN; —S$R^B$;—SO$R^B$;—SO$_2 R^B$;—NO$_2$;—N($R^B$)$_2$;—NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R_4$ is hydrogen or $C_{1-4}$ alkyl;
m is an integer 0 to 2, inclusive.

In some embodiments, X is S. In some embodiment, X is O. In some embodiments, X is $NR_4$, wherein $R_4$ is H or methyl. In some embodiments, X is absent.

In some embodiments, $R_1$ is a straight chain aliphatic. In some embodiments, $R_1$ is a branched chain aliphatic. In some embodiments, R1 is a straight chain heteroaliphatic. In some embodiments, $R_1$ is a branched chain heteroaliphatic.

In some embodiments, $R_1$ is $C_{1-4}$ alkyl, $C_{2-4}$ alkenyl, $C_{2-4}$ alkynyl. In some embodiments, $R_1$ is aryl or heteroaryl. In some embodiments $R_1$ is acyl.

In some embodiments, $R_1$ is $C_{1-4}$ alkyl. In some embodiments, $R_1$ is methyl, ethyl, n-propyl, i-propyl, n-butyl, i-butyl, or t-butyl.

In some embodiments, $R_2$ is optionally substituted aryl. In some embodiments, $R_2$ is optionally substituted heteroaryl. In some embodiments, $R_2$ is $C_{1-4}$ alkyl, $C_{2-4}$ alkenyl, $C_{2-4}$ alkynyl.

In some embodiments, $R_2$ is unsubstituted aryl. In some embodiments, $R_2$ is substituted aryl. In some embodiments, $R_2$ is unsubstituted phenyl. In some embodiments, $R_2$ is substituted phenyl. In some embodiments, $R_2$ is substituted the ortho position. In some embodiments, $R_2$ is substituted at the meta position. In some embodiments, $R_2$ is substituted at the para position. In some embodiments, $R_2$ is substituted at more than one position. In some embodiments, $R_2$ is substituted with a $C_{1-4}$ alkyl. In some embodiments, $R_2$ is substituted with $C_{1-4}$ alkoxy. In some embodiments, $R_2$ is substituted with $NO_2$. In some embodiments, $R_2$ is substituted with a halogen. In some embodiments, $R_2$ p-Me phenyl. In some embodiments, $R_2$ is o-methoxy phenyl. In some embodiments, $R_2$ is phenyl.

In some embodiments, m is 0. In some embodiments, m is 1. In some embodiments, m is 2.

In some embodiments, both $R_3$ are the same. In some embodiments, each $R_3$ is different.

In some embodiments, $R_3$ is H. In some embodiments, $R_3$ is $C_{1-4}$ alkyl. In some embodiments, $R_3$ is $NO_2$. In some embodiments, $R_3$ is halogen. In some embodiments, $R_3$ is $C_{1-4}$ alkoxy.

In some embodiments, two $R_3$ are taken together to form a five or six membered ring.

In some embodiments, a compound of Formula (I) is a compound BC11-38, wherein BC11-38 is as follows:

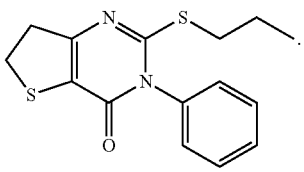 [SMILES: CCCSc1nc2c(c(=O)n1-c1ccccc1)SCC2]

In some embodiments, a compound of Formula (I) is a compound selected from the group consisting of BC11-38-1, BC11-38-2, BC11-38-3 or BC11-38-4, which correspond to structures:

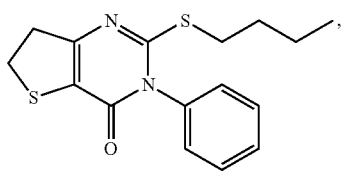

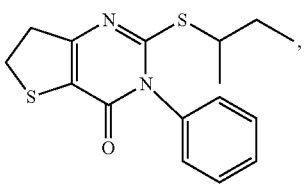

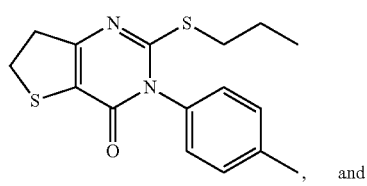

, and

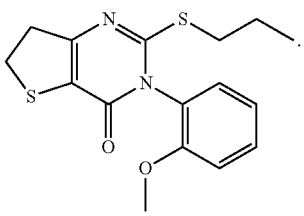

In some embodiments, a compound for inhibiting PDE11 is of formula (II):

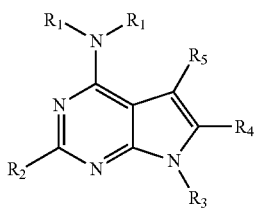

wherein
each $R_1$, and $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; or substituted or unsubstituted, branched or unbranched alkylaryl;

$R_2$, $R_4$ and $R_5$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo.

In some embodiments, both $R_1$ are the same. In some embodiments, each $R_1$ is different.

In some embodiments, each $R_1$ is independently hydrogen, $C_{1-4}$ alkyl, $C_{1-4}$ alkylaryl, or optionally substituted aryl.

In some embodiments, at least one $R_1$ is hydrogen.

In some embodiments, at least one $R_1$ is $C_{1-4}$ alkyl. In some embodiments, at least one R1 is methyl, ethyl, n-propyl, i-propyl, n-butyl, i-butyl, t-butyl. In some embodiments, one $R_1$ is hydrogen, and one $R_1$ is $C_{1-4}$ alkylaryl.

In some embodiments, at least one $R_1$ is $C_{1-4}$ alkylaryl. In some embodiments, $C_{1-4}$ alkylaryl is (CH$_2$)$_2$-phenyl.

In some embodiments, $R_1$ is unsubstituted aryl. In some embodiments, $R_1$ is substituted aryl. In some embodiments, $R_1$ is unsubstituted phenyl. In some embodiments, $R_1$ is substituted phenyl. In some embodiments, $R_1$ is substituted the ortho position. In some embodiments, $R_1$ is substituted at the meta position. In some embodiments, $R_1$ is substituted at the para position. In some embodiments, $R_1$ is substituted at more than one position. In some embodiments, $R_1$ is substituted with a $C_{1-4}$ alkyl. In some embodiments, $R_1$ is substituted with $C_{1-4}$ alkoxy. In some embodiments, $R_1$ is substituted with NO$_2$. In some embodiments, $R_1$ is substituted with a halogen. In some embodiments, $R_1$ is o-methoxy phenyl. In some embodiments, $R_1$ is phenyl.

In some embodiments, one $R_1$ is hydrogen, and one $R_1$ is substituted aryl.

In some embodiments, $R_2$ is hydrogen. In some embodiments, $R_2$ is NO$_2$. In some embodiments, $R_2$ is a five or six membered ring system. In some embodiments, $R_2$ is a halogen. In some embodiments, $R_2$ is a $C_{1-4}$ alkyl.

In some embodiments, $R_3$ is $C_{1-4}$ alkyl, $C_{1-4}$ alkylaryl, optionally substituted aryl, or optionally substituted heteroaryl.

In some embodiments, $R_3$ is $C_{1-4}$ alkylaryl. In some embodiments, $R_3$ is unsubstituted aryl. In some embodiments, $R_3$ is substituted aryl. In some embodiments, $R_3$ is unsubstituted phenyl. In some embodiments, $R_3$ is substituted phenyl. In some embodiments, $R_3$ is substituted the ortho position. In some embodiments, $R_3$ is substituted at the meta position. In some embodiments, $R_3$ is substituted at the para position. In some embodiments, $R_3$ is substituted at more than one position. In some embodiments, $R_3$ is substituted with a $C_{1-4}$ alkyl. In some embodiments, $R_3$ is substituted with $C_{1-4}$ alkoxy. In some embodiments, $R_3$ is substituted with $NO_2$. In some embodiments, $R_3$ is substituted with a halogen. In some embodiments, $R_3$ is p-fluoro phenyl. In some embodiments, $R_3$ is phenyl.

In some embodiments, $R_4$ is hydrogen. In some embodiments, $R_4$ is $NO_2$. In some embodiments, $R_4$ is a five or six membered ring system. In some embodiments, $R_4$ is a halogen. In some embodiments, $R_4$ is a $C_{1-4}$ alkyl.

In some embodiments, $R_5$ is substituted or unsubstituted, branched or unbranched aryl; substituted or unsubstituted, branched or unbranched heteroaryl; or substituted or unsubstituted, branched or unbranched alkylaryl.

In some embodiments, $R_5$ is hydrogen.

In some embodiments, $R_5$ is $C_{1-4}$ alkyl, C1-4 alkylaryl, optionally substituted aryl, or optionally substituted heteroaryl.

In some embodiments, $R_5$ is $C_{1-4}$ alkylaryl. In some embodiments, $R_5$ is unsubstituted aryl. In some embodiments, $R_5$ is substituted aryl. In some embodiments, $R_5$ is unsubstituted phenyl. In some embodiments, $R_5$ is substituted phenyl. In some embodiments, $R_5$ is substituted the ortho position. In some embodiments, $R_5$ is substituted at the meta position. In some embodiments, $R_5$ is substituted at the para position. In some embodiments, $R_5$ is substituted at more than one position. In some embodiments, $R_5$ is substituted with a $C_{1-4}$ alkyl. In some embodiments, $R_5$ is substituted with $C_{1-4}$ alkoxy. In some embodiments, $R_5$ is substituted with $NO_2$. In some embodiments, $R_5$ is substituted with a halogen. In some embodiments, $R_5$ is phenyl.

In some embodiments, a compound PDE11 inhibitor of formula (II) is BC11-28, wherein BC11-28 has the following structure.

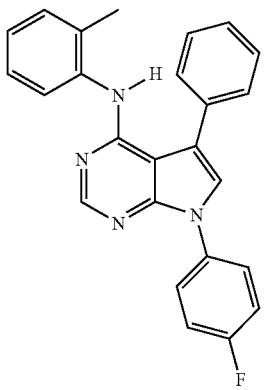 [SMILES: Cc1ccccc1Nc1ncnc2c1c(-c1ccccc1)cn2-c1ccc(F)cc1]

In some embodiments, compound PDE11 inhibitor of formula (II) is selected from the group consisting of:

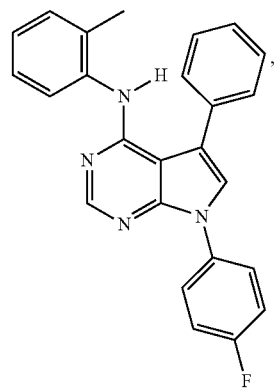

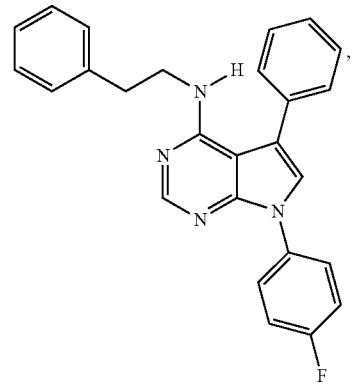

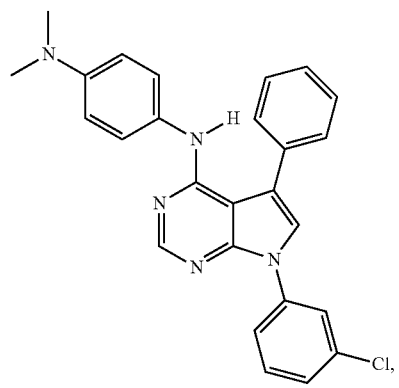

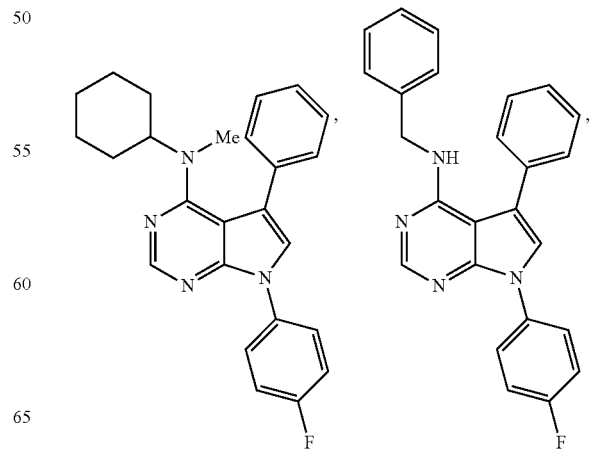

-continued

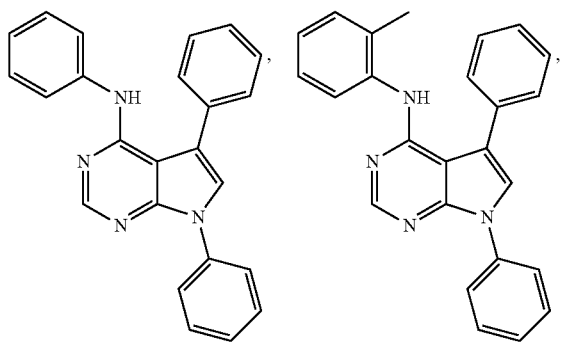

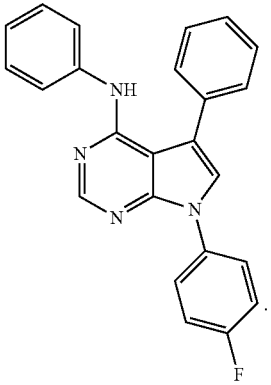

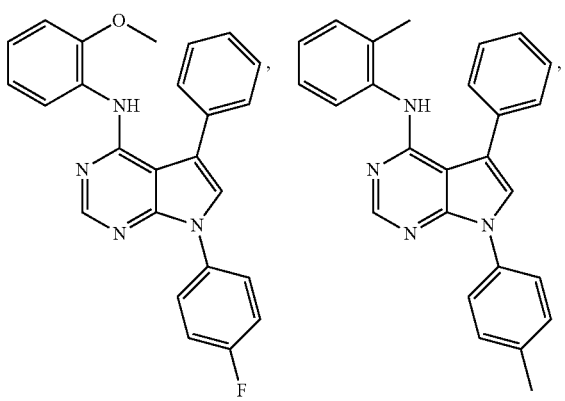

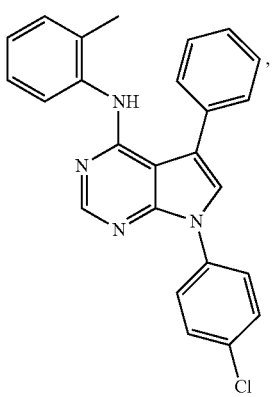 [SMILES: Fc1ccc(-n2cc(-c3ccccc3)c3c(Nc4ccccc4)ncnc32)cc1]

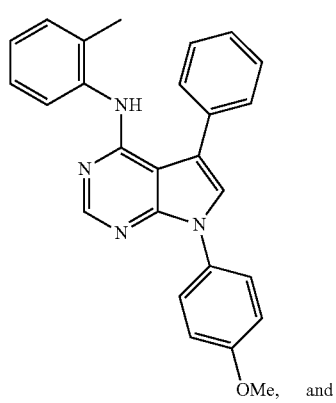

In some embodiments, a compound for inhibiting PDE11 is of formula (III):

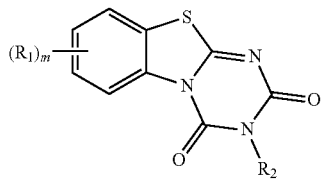

III wherein
each $R_1$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; or substituted or unsubstituted, branched or unbranched alkylaryl;

m is an integer 0 to 4, inclusive.

In some embodiments, each $R_1$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or C($R^B$)$_3$; wherein each occurrence of $R^B$ is independently hydrogen; halogen; aliphatic; heteroaliphatic; acyl; hydroxyl; aloxy; amino; alkylamino; dialkylamino; or alkylhalo.

In some embodiments, each $R_1$ is independently $C_{1-4}$ alkyl, $C_{1-4}$ alkoxy, $NO_2$, or a halogen.

In some embodiments, at least one $R_1$ is methyl, ethyl, n-propyl, i-propyl, n-butyl, i-butyl, or t-butyl. In some embodiments, at least one $R_1$ is methoxy, ethoxy, n-propoxy, i-propoxy, n-butoxy, i-butoxy, or t-butoxy.

In some embodiments, each $R_1$ are different. In some embodiments, each R1 are the same. In some embodiments, at least two $R_1$ are the same.

In some embodiments, m is 0. In some embodiments, m is 1.

In some embodiments, $R_2$ is substituted or unsubstituted, branched or unbranched aryl; substituted or unsubstituted, branched or unbranched heteroaryl; or substituted or unsubstituted, branched or unbranched alkylaryl.

In some embodiments, $R_2$ is C1-4 alkylaryl. In some embodiments, $R_2$ is unsubstituted aryl. In some embodiments, $R_2$ is substituted aryl. In some embodiments, $R_2$ is unsubstituted phenyl. In some embodiments, $R_2$ is substituted phenyl. In some embodiments, $R_2$ is substituted the ortho position. In some embodiments, $R_2$ is substituted at the meta position. In some embodiments, $R_2$ is substituted at the para position. In some embodiments, $R_2$ is substituted at more than one position. In some embodiments, $R_2$ is substituted with a $C_{1-4}$ alkyl. In some embodiments, $R_2$ is substituted with $C_{1-4}$ alkoxy. In some embodiments, $R_2$ is substituted with $NO_2$. In some embodiments, $R_2$ is substituted with a halogen. In some embodiments, $R_2$ is ortho, meta, or para chlorophenyl. In some embodiments, $R_2$ is phenyl.

In some embodiments, a compound of formula (III) is BC11-19 having the structure of:

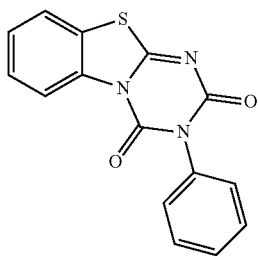 [SMILES: O=c1nc2sc3ccccc3n2c(=O)n1-c1ccccc1]

In some embodiments, a compound of formula (III) is selected from the group consisting of:

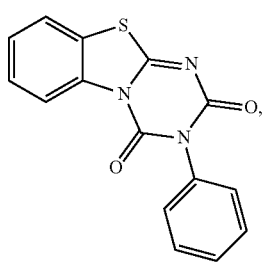

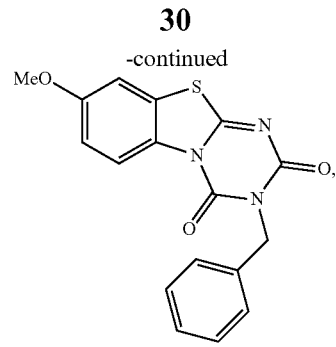

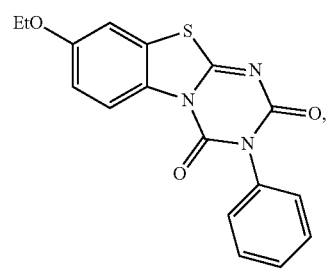

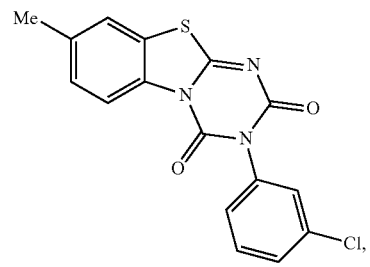

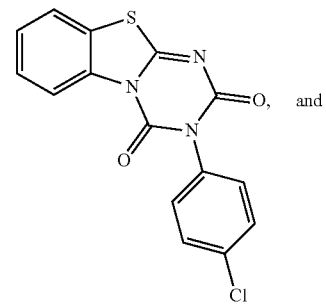 and

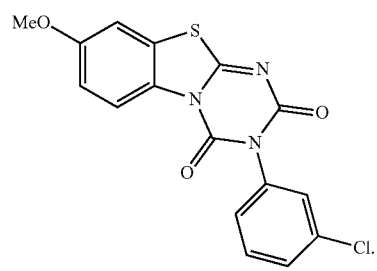

In some embodiments, a compound for inhibiting PDE11, wherein the compound is of formula (IV):

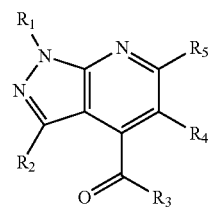

wherein
R$_1$ and R$_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; or substituted or unsubstituted, branched or unbranched alkylaryl;

R$_2$, R$_4$, and R$_5$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^B$; —CO$_2$R$^B$; -; —CN; —SCN; —SR$^B$; —SOR$^B$; —SO$_2$R$^B$; —NO$_2$; —N(R$^B$)$_2$; —NHC(O)R$^B$; or C(R$^B$)$_3$; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo.

In some embodiments, R$_1$ is hydrogen; substituted or unsubstituted, branched or unbranched aryl; substituted or unsubstituted, branched or unbranched heteroaryl; or substituted or unsubstituted, branched or unbranched alkylaryl.

In some embodiments, R$_1$ is C$_{1-4}$ alkyl, or C$_{1-4}$ alkylnitrile.

In some embodiments, R$_1$ is C$_{1-4}$ alkylaryl. In some embodiments, R$_1$ is unsubstituted aryl. In some embodiments, R$_1$ is substituted aryl. In some embodiments, R$_1$ is unsubstituted phenyl. In some embodiments, R$_1$ is substituted phenyl. In some embodiments, R$_1$ is substituted the ortho position. In some embodiments, R$_1$ is substituted at the meta position. In some embodiments, R$_1$ is substituted at the para position. In some embodiments, R$_1$ is substituted at more than one position. In some embodiments, R$_1$ is substituted with a C$_{1-4}$ alkyl. In some embodiments, R$_1$ is substituted with C$_{1-4}$ alkoxy. In some embodiments, R$_1$ is substituted with NO$_2$. In some embodiments, R$_1$ is substituted with a halogen. In some embodiments, R$_1$ is phenyl.

In some embodiments, R$_2$ is hydrogen. In some embodiments, R$_2$ is cyclic or acyclic, substituted or unsubstituted, branched or unbranched aliphatic; cyclic or acyclic, substituted or unsubstituted, branched or unbranched heteroaliphatic.

In some embodiments, R$_2$ is C$_{1-4}$ alkyl, C$_{1-4}$ alkoxy, NO$_2$, or a halogen. In some embodiments, R$_2$ is methyl, ethyl, n-propyl, i-propyl, n-butyl, i-butyl, or t-butyl.

In some embodiments, R$_3$ is cyclic or acyclic, substituted or unsubstituted, branched or unbranched aliphatic; cyclic or acyclic, substituted or unsubstituted, branched or unbranched heteroaliphatic.

In some embodiments, R$_3$ O—C$_{1-4}$ alkyl. In some embodiments, R$_3$ is alkylamino or dialkylamino. In some embodiments, R$_3$ is C$_{1-4}$ alkylamino. In some embodiments, C$_{1-4}$ dialkyamino.

In some embodiments, R$_4$ is hydrogen. In some embodiments, R$_2$ is C$_{1-4}$ alkyl.

In some embodiments, R$_5$ substituted or unsubstituted, branched or unbranched aryl; substituted or unsubstituted, branched or unbranched heteroaryl; or substituted or unsubstituted, branched or unbranched alkylaryl.

In some embodiments, R$_5$ is C$_{1-4}$ alkylaryl. In some embodiments, R$_5$ is unsubstituted aryl. In some embodiments, R$_5$ is substituted aryl. In some embodiments, R$_5$ is unsubstituted phenyl. In some embodiments, R$_5$ is substituted phenyl. In some embodiments, R$_5$ is substituted the ortho position. In some embodiments, R$_5$ is substituted at the meta position. In some embodiments, R$_5$ is substituted at the para position. In some embodiments, R$_5$ is substituted at more than one position. In some embodiments, R$_5$ is substituted with a C$_{1-4}$ alkyl. In some embodiments, R$_5$ is substituted with C$_{1-4}$ alkoxy. In some embodiments, R$_5$ is substituted with NO$_2$. In some embodiments, R$_5$ is substituted with a halogen. In some embodiments, R$_5$ is phenyl.

In some embodiments, R$_5$ is unsubstituted heteroaryl. In some embodiments, R$_5$ is substituted heteroaryl. In some embodiments, R$_5$ is substituted at only one position. In some embodiments, R$_5$ is substituted at more than one position. In some embodiments, R$_5$ is substituted with a C$_{1-4}$ alkyl. In some embodiments, R$_5$ is substituted with C$_{1-4}$ alkoxy. In some embodiments, R$_5$ is substituted with NO$_2$. In some embodiments, R$_5$ is substituted with a halogen.

In some embodiments, a compound of formula (IV) is BC11-15 with the structure as follows:

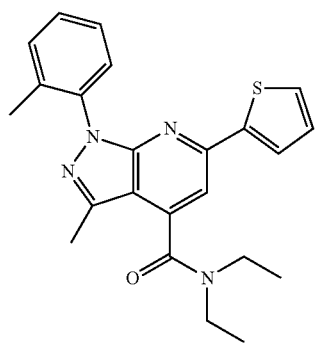 [SMILES: CCN(CC)C(=O)c1cc(-c2cccs2)nc2c1c(C)nn2-c1ccccc1C]

In some embodiments, a compound of formula (IV) is selected from the group consisting of:

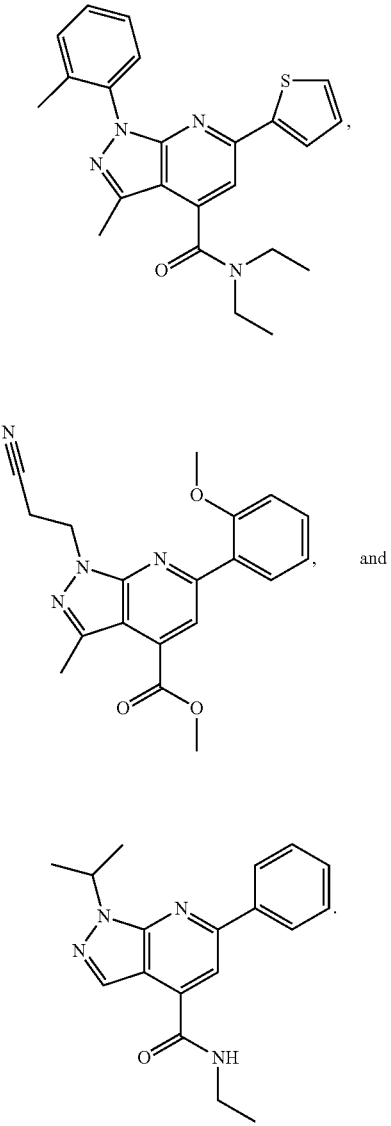

Exemplary Dual Selective PDE11/PDE Inhibitors

As disclosed herein are exemplary dual PDE11/PDE10 inhibitor compound is a compound of formula (V) or (VI) as disclosed herein.

In some embodiments, a compound for inhibiting PDE11, wherein the compound is of formula (V):

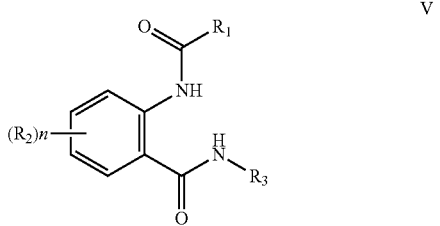

V wherein $R_1$, and $R_3$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

each $R_2$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

n is an integer 0 to 4, inclusive.

In some embodiments, $R_1$ is unsubstituted aryl. In some embodiments, $R_1$ is substituted aryl. In some embodiments, $R_1$ is unsubstituted phenyl. In some embodiments, $R_1$ is substituted phenyl. In some embodiments, $R_1$ is substituted the ortho position. In some embodiments, $R_1$ is substituted at the meta position. In some embodiments, $R_1$ is substituted at the para position. In some embodiments, $R_1$ is substituted at more than one position. In some embodiments, $R_1$ is substituted with a $C_{1-4}$ alkyl. In some embodiments, $R_1$ is substituted with $C_{1-4}$ alkoxy. In some embodiments, $R_1$ is substituted with NO$_2$. In some embodiments, $R_1$ is substituted with a halogen. In some embodiments, $R_1$ is phenyl.

In some embodiments, $R_2$ is $C_{1-4}$ alkyl. In some embodiments, $R_2$ $C_{1-4}$ alkoxy. In some embodiments, $R_2$ is NO$_2$. In some embodiments, $R_2$ is halogen.

In some embodiments, all $R_2$ are the same. In some embodiments, all $R_2$ are different. In some embodiments, at least two $R_2$ are the same.

In some embodiments, n is 0.

In some embodiments, $R_3$ is optionally substituted aryl, or optionally substituted heteroaryl. In some embodiments, $R_3$ is optionally substituted bicyclic. In some embodiments, $R_3$ is bicyclic substituted at at least one position.

In some embodiments, $R_3$ is

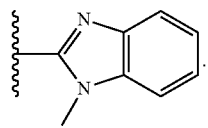 [SMILES: *c1nc2ccccc2n1C]

In some embodiments, a compound of formula (V) is BC11-4, which has the following structure:

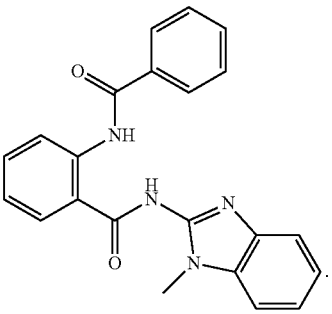 [SMILES: Cn1c(NC(=O)c2ccccc2NC(=O)c2ccccc2)nc2ccccc21]

In some embodiments, a compound of formula (V) is BC11-4-1, or BC11-4-2, or BC11-4-3 which have the following structures:

BC11-4-1

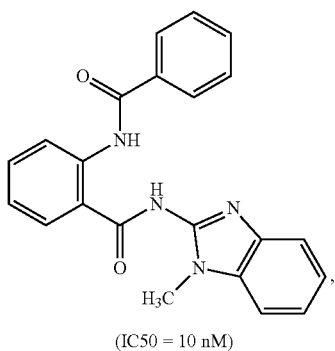

(IC50 = 10 nM)

BC11-4-2

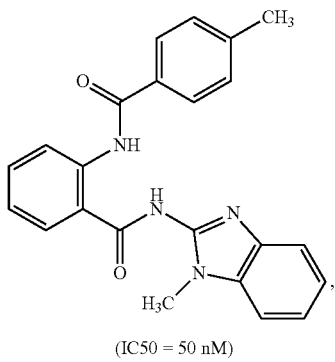

(IC50 = 50 nM)

BC11-4-3

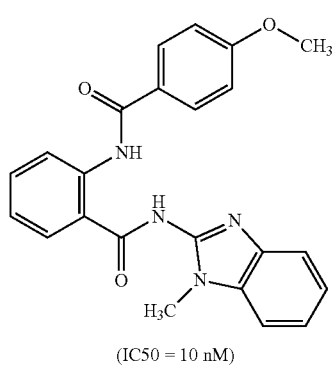

(IC50 = 10 nM)

In some embodiments, a compound of formula (V), including but not limited to BC11-4, BC11-4-1, BC11-4-2, BC11-4-3 can inhibit both PDE11 and PDE10, and is referred to herein as a "PDE11/PDE10 dual inhibitor".

In another embodiment, a compound for inhibiting PDE11 is of formula (VI):

VI

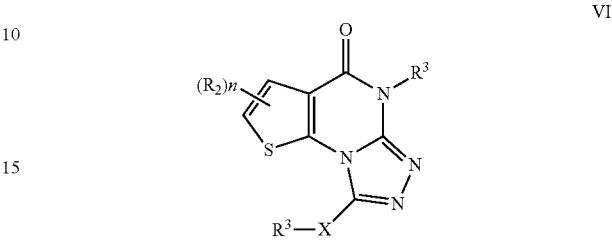

wherein

X is O, $NR_4$, S or absent;

$R_1$, $R_3$ and $R_4$ are independently, hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

each $R_2$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

n is an integer 0-2, inclusive.

In some embodiments, X is S.

In some embodiments, $R_1$ is hydrogen.

In some embodiments, $R_1$ is $C_{1-4}$ alkyl, $C_{1-4}$ alkylaryl, optionally substituted aryl, or optionally substituted heteroaryl.

In some embodiments, $R_1$ is $C_{1-4}$ alkylaryl. In some embodiments, $R_1$ is unsubstituted aryl. In some embodiments, $R_1$ is substituted aryl. In some embodiments, $R_1$ is unsubstituted phenyl. In some embodiments, $R_1$ is substituted phenyl. In some embodiments, $R_1$ is substituted the ortho position. In some embodiments, $R_1$ is substituted at the meta position. In some embodiments, $R_1$ is substituted at the para position. In some embodiments, $R_1$ is substituted at more than one position. In some embodiments, $R_1$ is substituted with a $C_{1-4}$ alkyl. In some embodiments, $R_1$ is substituted with $C_{1-4}$ alkoxy. In some embodiments, $R_1$ is substituted with $NO_2$. In some embodiments, $R_1$ is substituted with a halogen. In some embodiments, $R_1$ is phenyl.

In some embodiments, $R_2$ is $C_1$-$C_4$ alkyl.

In some embodiments, n is 0. In some embodiments, n is 1. In some embodiments, n is 2.

In some embodiments, $R_3$ is substituted or unsubstituted, branched or unbranched alkyl. In some embodiments, $R_3$ is $C_1$-$C_4$ alkyl.

In some embodiments, $R_3$ is substituted or unsubstituted, branched or unbranched alkenyl. In some embodiments, $R_3$ is $C_2$-$C_4$ alkenyl.

In some embodiments, a compound of formula (VI) is BC11-8 having the structure as follows:

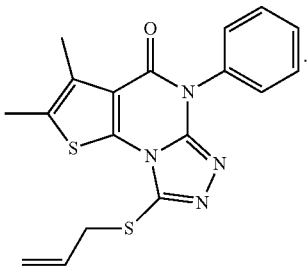 [SMILES: C=CCSc1nnc2n(-c3ccccc3)c(=O)c3c(C)c(C)sc3n12]

In some embodiments, a compound of formula (VI) is BC11-8-1, or BC11-8-2 which have the following structures:

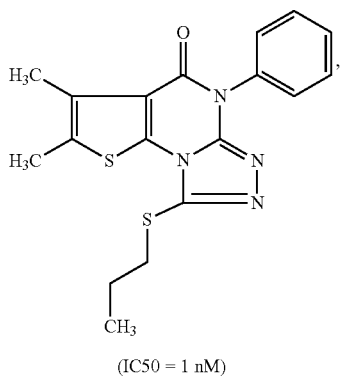

BC11-8-1

(IC50 = 1 nM)

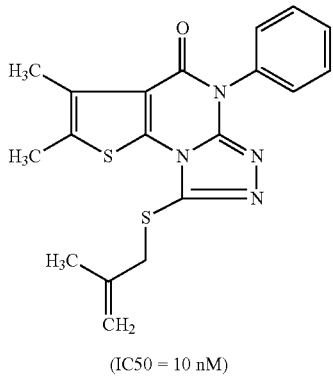

BC11-8-2

(IC50 = 10 nM)

In some embodiments, a compound of formula (VI), including but not limited to, BC11-8, BC11-8-1, BC11-8-2, inhibits both PDE11 and PDE10, and thus is a dual PDE11/PDE10 inhibitor as disclosed herein.

As used herein, the term "linker" means an organic moiety that connects two parts of a compound. Linkers typically comprise a direct bond or an atom such as oxygen or sulfur, a unit such as NH, C(O), C(O)NH, SO, $SO_2$, $SO_2NH$ or a chain of atoms, such as optionally substituted alkyl, optionally substituted alkenyl, optionally substituted alkynyl, optionally substituted cyclyl, optionally substituted heterocycly, optionally substituted aryl, optionally substituted heteroaryl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^L)_2$, C(O), cleavable linking group, optionally substituted aryl, optionally substituted heteroaryl, optionally substituted cyclyl, optionally substituted heterocyclyl; where $R^L$ is hydrogen, acyl, aliphatic or substituted aliphatic.

Candidate compounds of formula (I), (II), (III), (IV), (V) and (VI) can be tested for inhibitory activity of PDE11 proteins (e.g., PDE11A) and/or binding to PDE11 proteins, according to the assays disclosed herein in the Examples, including the fission yeast assay measuring growth of yeast expressing PDE11A enzyme and/or PDE11A catalytic subunit in the presence of 5FOA media. A skilled artisan can readily recognize that there is no limit as to the structural nature of the agents of formula (I), (II), (III), (IV), (V) and (VI) tested for binding and inhibition of activity of PDE11 proteins.

Candidate compounds of formula (V) or (VI) can be tested for inhibitory activity of PDE11 proteins and/or PDE10 proteins, as well as binding to PDE11 and/or PDE10 proteins, according to the assays disclosed herein in the Examples, including the fission yeast growth assay measuring growth of yeast expressing the PDE11A enzyme and/or PDE11A catalytic subunit, and/or the PDE10 enzyme and/or PDE10 catalytic subunit in the presence of 5FOA media. A skilled artisan can readily recognize that there is no limit as to the structural nature of the agents of formula (V) or (VI) tested for binding and inhibition of activity of PDE11 and PDE10 proteins.

Figure 9:
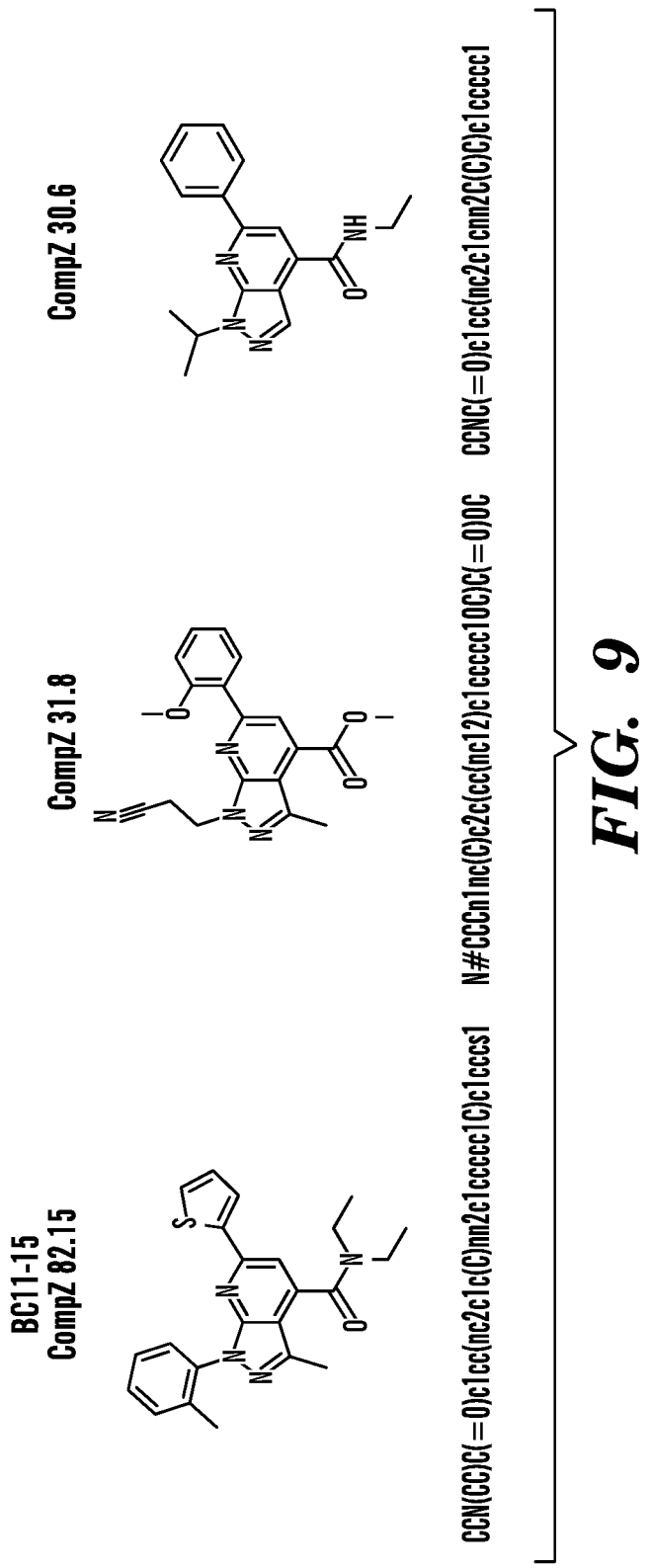
FIG. 9 shows exemplary compounds of formula (IV), showing the structure of BC11-15 and two related compounds that were all detected as hits in the initial screen at the ICCB Screening Facility. Also shown are the Composite Z scores that represent the degree to which a compound stimulated growth of the screening strain relative to DMSO (the solvent used for the screening compounds). BC11-15 was categorized as a strong hit ($73^{rd}$ highest Composite Z score), while the two related compounds were categorized as moderate hits (in the top 0.27% of compounds screened).
Figure 10:
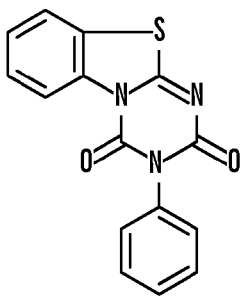
FIG. 10 shows exemplary compounds of formula (III) showing the structures of BC11-19 and five derivatives of BC11-19 (BC11-19-1, BC11-19-2, BC11-19-3, BC11-19-4, and BC11-19-5) and provides IC50 data from in vitro enzyme assays using PDE11A.
Figure 10:
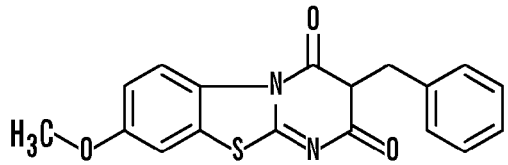
Figure 10:
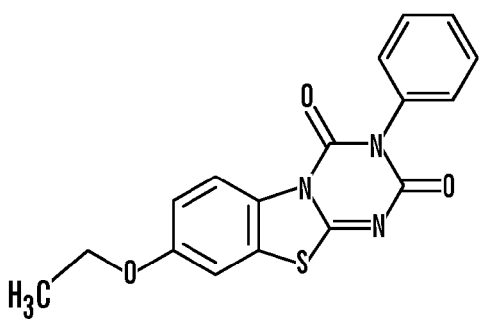
Figure 10:
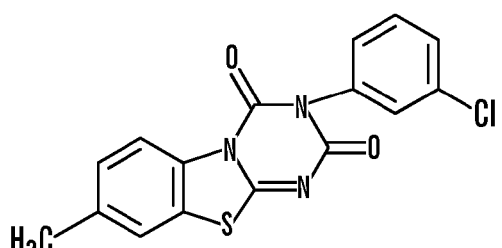
Figure 10:
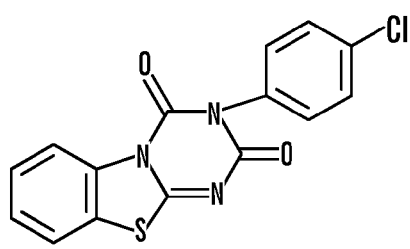
Figure 10:
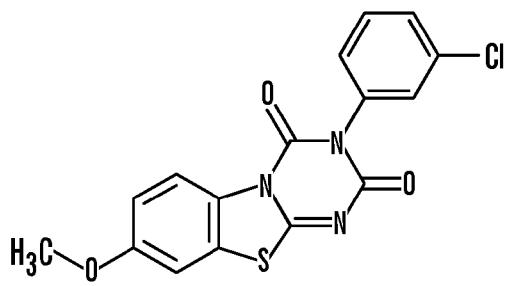
Figure 11:
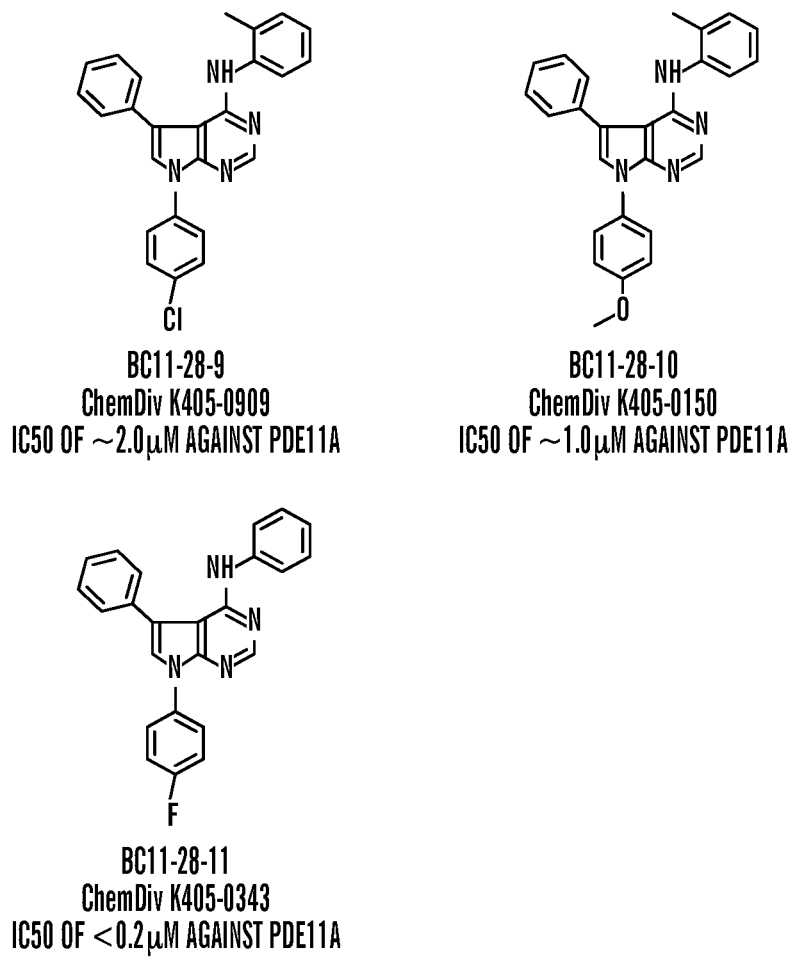
FIG. 11 shows exemplary compounds of formula (II) showing the structures of BC11-28 and eleven derivatives of BC11-28 (BC11-28-1 to BC11-28-11) and provides IC50 data from in vitro enzyme assays using PDE11A.

Compositions Comprising PDE11 Inhibitors and/or Dual PDE11/PDE Inhibitors and Derivatives Thereof In some embodiments, a composition as disclosed herein for use in the methods as disclosed herein comprise a substantially pure composition of any one or more of compounds of formula (I)-(VI) as disclosed above. In some embodiments, a composition comprises a compound of formula (I) and in some embodiments, the compound of formula (I) is, for example, selected from BC11-38, BC11-38-1, BC11-38-2. In some embodiments, a composition comprises a compound of formula (II) and in some embodiments a compound of formula (II) is BC11-28, or any derivative, e.g., BC11-28-1 to BC11-28-11, as shown in FIG. 11. In some embodiments, a composition comprises a compound of formula (III) and in some embodiments a compound of formula (III) is BC11-19, or a derivative, e.g., BC11-19-1, BC11-19-2, BC11-19-3, BC11-19-4, or BC11-19-5, as shown in FIG. 10. In some embodiments, a composition comprises a compound of formula (IV) and in some embodiments a compound of formula (IV) is BC11-15, or a derivative as shown in FIG. 9. In some embodiments, a compound of formula (V) is BC11-4 or a derivative thereof, e.g., BC11-4-1, BC11-4-2, or BC11-4-3. In some embodiments, a compound of formula (VI) is BC11-8 or a derivative thereof. In some embodiments, a compound of formula (VI) is BC11-8 or a derivative thereof, e.g., BC11-8-1, BC11-8-2.

In some embodiments, a composition comprising one or more compounds of formula (I)-(VI) comprises at least about 80%, or at least about 85%, or at least about 90%, or at least about 92%, or at least about 95%, or at least about 97%, or at least about 98%, or at least about 99%, or at least about 99.5%, or at least about 99.8% or more than 99.8% of a compound of formula (I), (II), (III), (IV), (V) or (VI).

As used herein, the term "composition" is intended to encompass a product comprising the specified ingredients in the specified amounts, as well as any product which results, directly or indirectly, from combinations of the specified ingredients in the specified amounts.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

All stereoisomers of the present compounds, including enantiomeric and diastereomeric forms, are contemplated within the scope of this invention. Individual stereoisomers of the compounds of the invention may, for example, be substantially free of other isomers, or may be admixed with all other, or other selected, stereoisomers. The chiral centers of the present invention can have the S or R configuration as defined by the IUPAC 1974 Recommendations.

One skilled in the art will recognize that wherein a reaction step of the present invention may be carried out in a variety of solvents or solvent systems, said reaction step may also be carried out in a mixture of the suitable solvents or solvent systems.

It will also be appreciated by those skilled in the art that the compounds of the present invention may also be utilized in the form of their pharmaceutically acceptable salts or solvates thereof. The pharmaceutically acceptable salts of the compounds of the present invention are in particular salts which are non-toxic, or which can be used physiologically.

Thus, when the compounds of the present invention represented by the formula (I), (II), (III), (IV), (V) or (VI), contain one or more basic groups, i.e. groups which can be protonated, they can form an addition salt with a non-toxic inorganic or organic acid. Examples of suitable inorganic acids include: boric acid, perchloric acid, hydrochloric acid, hydrobromic acid, hydrofluoric acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, fumaric acid, phenylacetic acid, glutamic acid, benzoic acid, salicylic acid, sulfanilic acid, 2-acetoxybenzoic acid, toluenesulfonic acid, methanesulfonic acid, benzenesulfonic acid, ethane disulfonic acid, oxalic acid, isethionic acid, ketoglutaric acid, glycerophosphoric acid, aspartic acid, picric acid, lauric acid, palmitic acid, cholic acid, pantothenic acid, alginic acid, naphthoic acid, mandelic acid, tannic acid, camphoric acid and other organic acids known to the person skilled in the art. Preferred salts of the compounds of formula (I), (II), (III), (IV), (V) or (VI), include methane sulphonic acid, hydrochloric acid and p-toluenesulphonic acid salts.

Thus, when the compounds of the present invention represented by the formula (I), (II), (III), (IV), (V) or (VI), contain an acidic group they can form an addition salt with a suitable base. For example, such salts of the compounds of the present invention may include their alkali metal salts, such as Li, Na and K salts, or alkaline earth metal salts, like Ca and Mg salts, or aluminium salts, or salts with ammonia or salts of organic bases, such as lysine, arginine, guanidine, diethanolamine, choline and tromethamine.

As disclosed herein, a PDE11 inhibitor and dual PDE11/PDE10 inhibitor compound can be formulated as a salt, prodrug and solvate. The term "salt(s)", as employed herein, denotes acidic and/or basic salts formed with inorganic and/or organic acids and bases and Zwitterions (internal or inner salts) are also included. Also included herein are quaternary ammonium salts such as alkylammonium salts. Pharmaceutically acceptable (i.e., non-toxic, physiologically acceptable) salts are preferred.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like.

The pharmaceutically acceptable salts of the present invention can be synthesized from the subject compound of formula (I)-(VI), which contains a basic or an acidic moiety, by conventional chemical methods. Generally, the salts are prepared by contacting the free base or acid with stoichiometric amounts or with an excess of the desired salt-forming inorganic or organic acid or base in a suitable solvent or dispersant or from another salt by cation or anion exchange. Suitable solvents are, for example, ethyl acetate, ether, alcohols, acetone, THF, dioxane, or mixtures of these solvents.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphatediphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (+−)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

In some embodiments, compounds of formula (I)-(VI) as disclosed herein are basic in nature are capable of forming a wide variety of salts with various inorganic and organic acids. The acids that may be used to prepare pharmaceutically acceptable acid addition salts of the compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other compounds of the invention not specifically described in the foregoing experimental section can be accomplished using combinations of the reactions described above that will be apparent to those skilled in the art.

Prodrugs and solvates of a PDE11 inhibitor, as disclosed herein, such as a compound of formula (I)-(IV), or dual PDE11/PDE inhibitor, such as a compound of formulas (V) or (VI) are also contemplated herein. The term "prodrug", as employed herein, denotes a compound that, upon administration to a subject, undergoes chemical conversion by metabolic or chemical processes to yield a compound described herein or a salt and/or solvate thereof.

Thus, the present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Accordingly, in some embodiments, a PDE11 inhibitor, such as a compound of any of formula (I)-(VI) as disclosed herein can be formulated as a prodrug, and can become activated in vivo upon predefined chemical modifications. Prodrugs of an active compound of a PDE11 inhibitor, such as any compound of formula (I)-(VI), can be prepared by modifying functional groups present in the active compound in such a way that the modifications are cleaved, either in routine manipulation or in vivo, to the parent active compound. Prodrugs of a PDE11 inhibitor, such as any compound of formula (I)-(VI) can include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design*, Theory and Application, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Phannacokinet.*, 15(2): 143-53 (1990); Balimane and Sinko, "Involvement of multiple transporters in the oral absorption of nucleoside analogues", *Adv. DrugDelivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Arfv. Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); *Farquhar D*, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl)Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [Symp.] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The present invention furthermore includes all solvates of a PDE11 inhibitor, such as any compound of formula (I)-(VI), for example hydrates, and the solvates formed with other solvents of crystallization, such as alcohols, ethers, ethyl acetate, dioxane, DMF, or a lower alkyl ketone, such as acetone, or mixtures thereof.

The present invention also includes prodrug forms of a PDE11 inhibitor, such as any compound of formula (I)-(VI), for example the alkyl esters of acids or any of the prodrugs for guanidines known to one skilled in the art. Thus, the present invention includes those compounds produced in vivo after administration of a different compound (or prodrug of the compound). The in vivo effects of compounds described herein, may not be exerted by those compounds as such, but by one or more degradation products.

Various polymorphs of compounds forming part of the present invention may be prepared by crystallization of a small molecule PDE11 inhibitor, such as any compound of formula (I)-(VI) under different conditions. Examples of different conditions are: using different commonly used solvents or their mixtures for crystallization; crystallization at different temperatures; and various modes of cooling, ranging from very fast to very slow cooling during crystallizations. Polymorphs may also be obtained by heating or melting the compound followed by gradual or fast cooling. The presence of polymorphs may be determined by IR spectroscopy, solid probe NMR spectroscopy, differential scanning calorimetry, powder X-ray diffraction or such other techniques.

The compounds of the present invention can have asymmetric centers at any of the carbon atoms, including any one of the R substituents. Consequently, a PDE11 inhibitor, such as any compound of formula (I)-(VI) can exist in enantiomeric or diastereomeric forms either in pure or substantially pure form or in mixtures thereof in all ratios. When diastereomeric or enantiomeric products are prepared, they can be separated by conventional methods for example, chromatographic or fractional crystallization. If mobile hydrogen atoms are present, the present invention also encompasses all tautomeric forms of a PDE11 inhibitor, such as any compound of formula (I)-(VI).

The present invention is accordingly directed to a PDE11 inhibitor, such as any compound of formula (I)-(VI), or a prodrug thereof, or a pharmaceutically acceptable salt of the compound, for the manufacture of a medicament for the treatment of a mammal (e.g., human) having a disease or condition with low cortisol levels and/or adrenal insufficiency.

Another aspect of the present invention is directed to a method for preventing and/or minimizing the effect of low cortisol resulting from damage to the adrenal gland by administering to an affected mammal, (e.g., a female or male human), a therapeutically effective amount of a PDE11 inhibitor, such as any compound of formula (I)-(VI), or a prodrug thereof, or a pharmaceutically, acceptable salt thereof.

Characterizing PDE11 Inhibitors

A PDE11 inhibitor can be an agent that inhibits or decreases PDE11 enzyme activity. Such inhibitors include antibodies, peptides including mimetics, for example, mimetics having a PDE11 binding site and small molecules, for example selective PDE11 inhibitors and PDE11/PDE10 inhibitors. In one embodiment, a PDE11 small molecule inhibitor falls into one of six structural classes of compounds of formulas (I), (II), (III), (IV), (V) and (VI) as disclosed herein. All PDE11 inhibitors can be assessed for inhibition of PDE11A enzyme using a fission yeast *Schizosaccharomyces pombe*-based platform, as disclosed herein in the Examples, which heterologously-expresses PDE11A. These strains carry an fbp1-ura4 reporter that places the expression of the Ura4 OMP decarboxylase under the control of the PKA-repressed fbp1 promoter. Strains expressing this construct are sensitive to the pyrimidine analog 5-fluoro-orotic acid (5FOA) when PKA is not activated. This system was originally developed to study the genes of the glucosecAMP pathway in *S. pombe* (Hoffman, BiochemSoc Trans 2005; 33:257-260; Hoffman and Winston, Genetics 1990; 124(4):807-816), and then successfully adapted for the study of heterologously-express enzymes of the cAMP-specific PDE4 and PDE7 families (Alaamery et al., J. Biomol. Screening 2010: 15:359-367; Ivey F D, et al., J Biomol Screen 2008; 13(1): 62-71). By removing the adenylyl cyclase gene from these strains, the inventors established a finely-tuned control of PKA activity by the use of exogenous cAMP or cGMP, which allowed the introduction of PDE genes from 10 out of the 11 PDE families (Demirbas et al., Cellular Signalling 2011; 23(2):594-601.) The benefit to this approach allows PDE inhibitor compounds to be identified by their ability to stimulate the growth of the screening strain in 5FOA medium. As such, the inventors developed an assay that is capable of identifying compounds that inhibit PDE11 and also possess drug-like characteristics (e.g., stability for at least 24 to 48 hours or more, bioavailability etc.)

Furthermore, the compounds identified using this screen are both cell-permeable and non-toxic to yeast, demonstrating that the identified compounds do not non-specifically or promiscuously bind to many yeast proteins as this would be deleterious. The inventors have identified compounds that are chemically-stable, as they remain active for at least about 24 hours, or all or most of the 48 hr incubation period, which is required for the cultures to reach significant growth levels. Almost all compounds identified as PDE4, PDE7, PDE8, and PDE11 inhibitors have shown biological activity when tested in mammalian cell culture assays, even though they are direct hits from high throughput screen (HTS) libraries, demonstrating that this screening approach identifies compounds that are already biologically effective even prior to improvement via medicinal chemistry.

In some embodiments, a PDE11 inhibitor as used herein is preferably selective for inhibition of PDE11 to a greater extent than all other PDEs. In some embodiments as shown in the Examples, a PDE11 inhibitor can also be a dual PDE11/PDE inhibitor that is selective for inhibition of PDE11 and another PDE enzyme, such as PDE10. In some embodiments, such a dual selective PDE11/PDE10 inhibitor is selective for inhibition of PDE11 and all other PDE10 enzymes, including those encoded by the PDE10A gene. In some embodiments, a PDE11 inhibitor or dual PDE10/PDE11 inhibitor described herein is not-selective for inhibition of other PDEs, preferably, it does not inhibit the biological activity of other PDEs such as, PDE1A, PDE1B, PDE1C, PDE2, PDE3A, PDE3B, PDE4 (PDE4A, PDE4B, PDE4C, PDE4D), PDE5, PDE6, PDE7A, PDE7B, PDE8A, PDE8B, and/or PDE9. In some embodiments, a PDE11 inhibitor of formula (I)-(VI) as disclosed herein does not inhibit PDE5.

In some embodiments, a PDE11 inhibitor, such as any compound of formula (I)-(VI) as disclosed herein can inhibit PDE11 activity or expression by at least 10%, or about 20%, or about 25%, or about 50%, or about 75% or about 100%, or about 3-fold, or about 5-fold, or about 10-fold or more compared to inhibition of other PDE enzymes, such as PDE1 (e.g. PDE1A, PDE1B, PDE1C), PDE2, PDE3A, PDE3B, PDE4 (e.g., PDE4A, PDE4B, PDE4C, PDE4D), PDE5, PDE6, PDE7A, PDE7B, PDE8, and/or PDE9.

In some embodiments, a dual PDE11/PDE inhibitor, such as a PDE11/PDE10 inhibitor compound of formula (V) or (VI) as disclosed herein inhibits the other PDE enzyme, such as for example, PDE10 activity or expression by at least 10%, or about 20%, or about 25%, or about 50%, or about 75% or about 100%, or about 3-fold, or about 5-fold, or about 10-fold or more compared to inhibition of other PDE enzymes, such as PDE1 (e.g. PDE1A, PDE1B, PDE1C), PDE2, PDE3A, PDE3B, PDE4 (e.g., PDE4A, PDE4B, PDE4C, PDE4D), PDE5, PDE6, PDE7A, PDE7B, PDE8, and/or PDE9. In some embodiments, a PDE11 inhibitor that is a dual PDE11/PDE inhibitor can inhibit another PDE enzyme, such as a PDE5 enzyme. In some embodiments, a PDE11/PDE5 dual inhibitor such as Tadafafil (CIALIS®; ADCIRCA®) is not used in the methods and compositions as disclosed herein.

Table 1 shows the $IC_{50}$ values for in vitro enzyme assay profiling of exemplary PDE11 inhibitors and dual PDE11/PDE10 (e.g., BC11-4 and BC11-8) inhibitors for inhibition of PDE11A and other PDE enzymes. Assays were performed using substrate concentrations of 100 nM cGMP for PDE11A, 30 nM cAMP for PDE10A, 500 nM cGMP for PDE5A, 1.7 µM cGMP for PDE6C, 10 nM cAMP for PDE8A, 15 nM cAMP for PDE7A, and 625 nM cAMP for PDE4A.

TABLE 1

$IC_{50}$ values (µM) for exemplary compounds of Formula (I)-(VI) for PDE11A and other PDE enzymes. (n/a indicates values not available).

|  | BC11-38 | BC11-28 | BC11-19 | BC11-15 | BC11-4 | BC11-8 |
| --- | --- | --- | --- | --- | --- | --- |
| PDE11A | 0.28 | 0.11 | 0.33 | 0.18 | 0.15 | 0.05 |
| PDE1 | >100 | >100 | 10 | >100 | n/a | n/a |
| PDE2 | >100 | >100 | >100 | >100 | n/a | n/a |
| PDE3 | >100 | >100 | 51 | >100 | n/a | n/a |
| PDE4 | >100 | >100 | >100 | 70 | n/a | n/a |
| PDE5 | >100 | >100 | >100 | 43 | n/a | n/a |
| PDE6 | >100 | >100 | >100 | 25 | n/a | n/a |
| PDE7 | >100 | >100 | >100 | 43 | n/a | n/a |
| PDE8 | >100 | >100 | >100 | >100 | n/a | n/a |
| PDE9 | >100 | >100 | >100 | >100 | n/a | n/a |
| PDE10 | >100 | >100 | >100 | 35 | 2.0 | 0.2 |

PDE11 and dual PDE11/PDE10 (e.g., BC11-4 or BC11-8) inhibitors as disclosed herein can be tested for their selectivity of inhibition of PDE11A, e.g., PDE11A1 or PDE11A2, PDE11A3, PDE11A4 and/or inhibition of PDE10 (e.g., PDE10A) using an exemplary yeast growth screening assay as disclosed herein in the Examples. As disclosed herein in the Examples, an increase in growth of PDE11 expressing yeast strains after 48 hour of incubation with a candidate PDE11 inhibitor agent identifies the candidate agent is a PDE11 inhibitor. For example, using such a positive growth screen, a compound which confers 5FOA-resistant growth of fission yeast expressing exogenous PDE11 and causes an increase in optical density of the fission yeast identifies an inhibitor of PDE11, as disclosed herein in the Examples. Furthermore, the selectivity of a PDE11 inhibitor to inhibit other PDE enzymes can be determined by one of ordinary skill in the art by measuring the 5FOA growth curve of different PDE-expressing fission yeast strains including as PDE1 (e.g. PDE1A, PDE1B, PDE1C), PDE2, PDE3A, PDE3B, PDE4 (e.g., PDE4A, PDE4B, PDE4C, PDE4D), PDE5, PDE6, PDE7A, PDE7B, PDE8A, PDE8B, and/or PDE9, as disclosed herein in the Examples.

In some embodiments, a fission yeast assay to determine the efficacy of a PDE11 inhibitor, the fission yeast expresses PDE11A.

In some embodiments, a PDE11 inhibitor, such as any compound of formula (I)-(VI) as disclosed herein are designed to bind to at least a portion the catalytic domain of the PDE11A1 isoform so as the interfere with the interaction between PDE11A1 and cAMP. In some embodiments, a PDE11 inhibitor compound of formula (I)-(VI) competes with cAMP for binding to the active site of PDE11A4. In some embodiments, a PDE11 inhibitor compound of any of formula (I)-(VI) as disclosed herein are designed to bind to the catalytic domain region of PDE11A4, which is located between amino acid residues 563 and 933, inclusive, of the amino acid sequence shown in GenBank Accession No. NP_058649.3, or the corresponding amino acid residues encoded by the PDE11A nucleic acid sequences in GenBank Accession Nos. NM_016953.3.

In some embodiments, a PDE11 inhibitor, such as any compound of formula (I)-(VI) as disclosed herein can be designed to bind to a portion of the PDE11A1 isoform that is separate and distinct from the catalytic domain, wherein that portion of PDE11A1 is a binding site for a secondary molecule, such as a chaperone protein.

In some embodiments, a PDE11 inhibitor, such as any compound of formula (I)-(VI) as disclosed herein inhibits PDE11, (e.g., PDE11A1, PDE11A2, PDE11A3, PDE11A4) with an $IC_{50}$ of less than about 30 µM, or less than about 25 µM, or about 20 µM, or about 15 µM, or about 10 µM, or about 5 µM, or about 2 µM, or about 1 µM, or about 800 nM, or about 600 nM, or about 400 nM, or about 200 nM or less than 200 nM. In some embodiments, a PDE11 inhibitor as disclosed herein selectively inhibits PDE11 (e.g., PDE11A1, PDE11A2, PDE11A3, PDE11A4) with an $IC_{50}$ of less than about 30 µM, or less than about 800 nM, or less than about 600 nM, or less than about 400 nM, or less than about 200 nM or less than 200 nM. In some embodiments, a PDE11 inhibitor as disclosed herein can selectively inhibit PDE11(e.g., PDE11A1, PDE11A2, PDE11A3, PDE11A4) with an $IC_{50}$ of between about 30 µM-200 nM, for example, about 30 µM-10 µM, or about 15 µM-5 µM, or about 10 µM-1 µM, or about 1 µM-500 nM, or about 600 nM-400 nM, or about 400 nM-200 nM or less than 200 nM, as determined in an yeast growth screening assay using PDE11A expressing yeast, as disclosed herein. In some embodiments, a PDE11 inhibitor useful in the compositions, methods and kits as disclosed herein, has an $IC_{50}$ of between about 10 µM-200 nM, or between about 5 µM and 200 nM, or less than 200 nM, as determined by the yeast growth assay disclosed herein.

In some embodiments, a PDE11 inhibitor which is a dual PDE11/PDE inhibitor, such as a PDE11/PDE10 inhibitor as disclosed herein, such as a compound of formula (V) or (IV) as disclosed herein inhibits the other PDE enzyme, e.g., PDE10 (e.g., PDE10A) with an $IC_{50}$ of less than about 30 µM, or less than about 25 µM, or less than about 20 µM, or less than about 15 µM, or less than about 10 µM, or less than about 5 µM, or less than about 2 µM, or about 1 µM, or about 800 nM, or about 600 nM, or about 400 nM, or about 200 nM or less than 200 nM. In some embodiments, a PDE11/PDE10 inhibitor as disclosed herein selectively inhibits PDE10 (e.g., PDE10A) with an $IC_{50}$ of about 30 µM, or about 800 nM, or about 600 nM, or about 400 nM, or about 200 nM or less than 200 nM. In some embodiments, a PDE11/PDE10 inhibitor as disclosed herein selectively inhibits PDE10 (e.g., PDE10A) with an $IC_{50}$ of between about 30 µM-200 nM, for example, about 30 µM-10 µM, or about 15 µM-5 µM, or about 10 µM-1 µM, or about 1 µM-500 nM, or about 600 nM-400 nM, or about 400 nM-200 nM or less than 200 nM, as determined in a yeast screening assay using PDE10- or PDE10A expressing yeast, as disclosed herein in the Examples. In some embodiments, a PDE11/PDE11 inhibitor useful in the compositions, methods and kits as disclosed herein has an $IC_{50}$ of between about 10 µM-200 nM, or between about 5 µM and 200 nM, or less than 200 nM, as determined by the yeast growth screening assay disclosed herein.

In some embodiments, a PDE11 inhibitor that is a dual PDE11/PDE inhibitor can inhibit another PDE enzyme, such as a PDE5 enzyme. In some embodiments, a PDE11/PDE5 dual inhibitor such as Tadafafil (CIALIS®, ADCIRCA®) is not used in the methods and compositions as disclosed herein.

In some embodiments, a PDE11 inhibitor that is a dual PDE11/PDE inhibitor, such as a PDE11/PDE10 inhibitor of formula (V) or (VI) can inhibit the other PDE enzyme, e.g., PDE11 enzyme (e.g., PDE11A1, PDE11A2, PDE11A3, and/or PDE11A4) with the same selectivity as it inhibits the PDE10 (e.g., PDE10A). For example, in some embodiments, if a PDE11/PDE10 inhibitor inhibits PDE11 with an $IC_{50}$ of about 250 nM, the PDE11/PDE10 inhibitor can also inhibit PDE10 (e.g., PDE10A) with an $IC_{50}$ of about 250 nM. In alternative embodiments, a PDE11/PDE10 inhibitor of formula (V) or (VI) can inhibit PDE11 (e.g., PDE11A) enzyme with a lower $IC_{50}$ than it inhibits PDE10 (e.g., PDE10A), for example, a PDE11/PDE10 dual inhibitor of formula (V) or (VI) can inhibit PDE11 (e.g., PDE11A) with an $IC_{50}$ at least about 0.5%, or about 1% or about 2% or about 3% or about 4% or about 5% or about 10% or about 20% that of the $IC_{50}$ for inhibition of PDE10 (e.g., PDE10A). In some embodiments, it desirable to have a dual PDE11/PDE10 with a weaker PDE10 inhibitory activity as compared to inhibition activity of PDE11.

In alternative embodiments, a dual PDE11/PDE inhibitor, such as a PDE11/PDE10 inhibitor of formula (V) or (VI) can inhibit the other PDE enzyme, e.g., PDE10 (e.g., PDE10A) enzyme with a higher $IC_{50}$ than it inhibits PDE11 (e.g., PDE11A). By way of an example only, but applies to all PDE11/PDE inhibitors, a PDE11/PDE10 dual inhibitor of formula (V) or (VI) can inhibit PDE10 (e.g., PDE10A) with an $IC_{50}$ at least about 0.5%, or about 1% or about 2% or about 3% or about 4% or about 5% or about 10% or about 20% higher than the $IC_{50}$ for inhibition of PDE11 (e.g., PDE11A). In some embodiments, it is possible that dual PDE11/PDE10 inhibitor compounds that possess too much activity for inhibition of PDE10 as compared to inhibition of PDE11 activity may produce an emetic response that would narrow the therapeutic window. Accordingly, in some embodiments, it is desirable to select PDE11/PDE10 inhibitor compounds for use in the compositions and methods as disclosed herein which have an efficacy of inhibition of PDE11 activity and inhibition of PDE10 activity about the same, or to select PDE11/PDE10 inhibitor compounds where the efficacy of inhibition of PDE11 activity higher than the efficacy of inhibition of PDE10 activity.

Regardless of the ratio of $IC_{50}$ for inhibition of PDE11:PDE of a dual PDE11/PDE inhibitor, such an inhibitor is selective for inhibition of PDE11 and the other dual-PDE enzyme (e.g., PDE10 in a PDE11/PDE10 dual inhibitor) and it does not significantly inhibit the biological activity of other PDEs such as, PDE1 (e.g. PDE1A, PDE1B, PDE1C), PDE2, PDE3A, PDE3B, PDE4 (e.g., PDE4A, PDE4B, PDE4C, PDE4D), PDE5, PDE6, PDE7A, PDE7B, PDE8A, PDE8B and/or PDE9.

In some embodiments, the compounds as disclosed herein are assessed in vivo in whole animal studies to demonstrate the utility of PDE11 inhibitors for elevating cortisol production in hypocortisolism. Such in vivo studies also enable determination of appropriate pharmacokinetic properties determine whether PDE11 inhibitors can reverse hypocortisolism as a way of treating conditions associated with adrenal insufficiency. In some embodiments, a PDE11 inhibitor, such as any compound of formula (I)-(VI) can be assessed in an adrenocortical dysplasia (acd) mouse, which is a model for human congenital adrenal hypoplasia and adrenal insufficiency. In some embodiments, a PDE11 inhibitor that increases cortisol levels in acd mouse can be selected for use in the methods, compositions and kits as disclosed herein. In some embodiments, a PDE11 inhibitor, such as any compound of formula (I)-(VI) which increases cortisol levels in acd mice by at least about 10% or more, or by about 15%, or at least about 20%, or at least about 30%, or at least about 40%, or at least about 50%, or at least about 60%, or at least about 70%, or at least about 80%, or at least about 90%, or at least about 100%, or at least about 1.5-fold, or at least about 2-fold, or at least about 3-fold or more than 3-fold can be selected for use in the methods, compositions and kits as disclosed herein.

A PDE11 inhibitor, such as any compound of formula (I)-(VI) can be tested for inhibition of activity of PDE11 and/or PDE10 activity, and/or binding with PDE11 and/or PDE10 proteins, and can be randomly selected or rationally selected. As used herein, a compound or agent is said to be randomly selected when the compound is chosen randomly without considering the specific structural conformation of the PDE11 inhibitor compound. Examples of randomly selected agents are members of a chemical library, or derivatives or analogues of a PDE11 inhibitor, such as any compound of formula (I)-(VI).

As used herein, an agent is said to be rationally selected when the agent is chosen on a nonrandom basis that is based on the structural conformation in connection with the compound's action. Compounds can be rationally selected by selecting compounds with specific conformational modifications or properties that make up the compound.

Differential screening assays known in the art can be used to select those compounds of the present invention with specificity for PDE11 inhibition, in particular human PDE11 inhibition. In some embodiments, where it is desirable to inhibit non-human PDE11, e.g., in cattle or other commercial non-human mammals, a PDE11 inhibitor, such as any compound of formula (I)-(VI) can be assessed for specificity and selectivity of bovine PDE11 inhibition. Thus, compounds that act specifically on human, or alternatively non-human (e.g., bovine) PDE11 inhibition can be selected to be used as a PDE11 inhibitor in the methods and compositions as disclosed herein.

In some embodiments, where a PDE11 inhibitor, such as any compound of formula (I)-(VI) is used in the treatment of living beings other than humans, e.g., for agricultural or commercial animals, a PDE11 inhibitor can be formulated to inhibit non-human PDE11 with an $IC_{50}$ at least an order of magnitude less than an $IC_{50}$ for inhibition of a human PDE11, though more preferably at least two or three orders of magnitude less. In such an embodiment is useful for administering to non-human animals, but avoiding such compounds being also effective to the general population who are consumers of the meat, or getting into the water system from the agricultural plant.

The primary aspect of the present invention is a method for treating a mammal (e.g., human) having a disease or condition with low cortisol levels by administering a therapeutically effective amount of a PDE11 inhibitor, such as any compound of formula (I)-(VI), a prodrug thereof, or a pharmaceutically acceptable salt of the compound or of the prodrug, to the mammal.

Screening Methods

As is disclosed above, another aspect of the present invention relates to a screening method for identifying a PDE11 inhibitor compound or agent that can be used in the therapeutic methods described herein. Such screening methods include a determination of whether a candidate compound is a PDE11 inhibitor and inhibits PDE11 alone or inhibits PDE11 in combination with another PDE enzyme, e.g., PDE10. In some embodiments, such a screening methods can be optionally followed by assessment of a candidate PDE11 inhibitor, such as any compound of formula (I)-(VI) being effective at increasing cortisol levels in a subject, or increasing cortisol production in a subject, or in treating a symptom of a low cortisol levels and/or adrenal insufficiency or an associated disease or disorder as disclosed herein. Alternatively, a screening method as disclosed herein can simply assess other agents and compounds that are known to be PDE11 inhibitors for their efficacy in such therapeutic methods.

In some embodiments, a PDE11 inhibitor, such as any compound of formula (I)-(VI) as disclosed herein can be assessed for its efficacy at inhibiting PDE11 activity using methods that are well known in the art, e.g., using the fission yeast *Schizosaccharomyces pombe*-based platform as disclosed herein in the Examples which expresses PDE11 (see also the yeast growth assay as disclosed in U.S. Patent Application 20100179158, which is incorporated herein in its entirety by reference.)

Accordingly as disclosed herein, one of ordinary skill can determine the efficacy for inhibition of PDE11 activity of a PDE11 inhibitor, such as any compound of formula (I)-(VI) using the fission yeast *Schizosaccharomyces pombe*-based platform as disclosed herein in the Examples, which comprises a fbp1-ura4 reporter construct that places the expression of the Ura4 OMP decarboxylase under the control of the PKA-repressed fbp1 promoter, and expresses PDE11 enzyme and is deficient for the active adenylyl cyclase gene (e.g., it is removed or results in non-functional gene expression of adenylyl cyclase protein). Accordingly, one can determine the efficacy for inhibition of PDE11 activity by incubating one or more candidate PDE11 inhibitor compounds with a culture of fission yeast for at least 48 hours, and measuring the growth of the fission yeast in 5FOA medium after 48 hours, and identifying a compound which stimulates growth of the yeast to an optical density (O.D) of at least about 0.5 at about 20 µM after 48 hours of incubation identifies a compound with PDE11 inhibitory activity and is useful in the methods, kits and compositions as disclosed herein.

In some embodiments, a fission yeast assay to determine the efficacy of a PDE11 inhibitor, the fission yeast expresses PDE11A, or a biologically active version of PDE11 enzyme.

In some embodiments, PDE11 inhibitors as disclosed herein are designed to bind to at least a portion the catalytic domain of the PDE11A isoform so as the interfere with the interaction between PDE11A and cAMP. In some embodiments, a PDE11 inhibitor as disclosed herein can compete with cAMP for binding to the active site of PDE11A. In some embodiments, a PDE11 inhibitor, such as any compound of formula (I)-(VI) as disclosed herein are designed to bind to the catalytic domain region of PDE11A4, which is located between amino acid residues 563 and 933, inclusive, of the amino acid sequence shown in GenBank Accession No. NP_058649.3, or the corresponding amino acid residues encoded by the PDE11A nucleic acid sequences in GenBank Accession Nos. NM_016953.3.

In some embodiments, a suitable PDE11 inhibitor as disclosed herein is designed to bind to a portion of the PDE11A1 isoform that is separate and distinct from the catalytic domain, wherein that portion of PDE11A1 is a binding site for a secondary molecule, such as a chaperone protein. For example, a PDE11 inhibitor can be designed to bind to at least a portion of the PDE11A protein so as to interfere with the interaction between PDE11A and a PDE11 co-factor or PDE11 chaperone protein. Preferably, such a PDE11 inhibitor can competes with the PDE11 chaperone and/or PDE11 co-factor for binding to PDE11A.

Similarly, one of ordinary skill can determine the efficacy for inhibition of a dual PDE11/PDE inhibitor, such as a PDE11/PDE10 compound of any of formulas (V) or (VI) for the inhibition of the other PDE enzyme (e.g., PDE10 in the case of a PDE11/PDE10 inhibitor) using the same screening method, with a minor modification in that the fission yeast express the other PDE enzyme (e.g., PDE10 enzyme, such as PDE10A) in place of the PDE11 enzyme. Measuring the growth of the fission yeast in 5FOA medium after 48 hours and identifying a compound which stimulates growth of the yeast to an optical density (O.D) of at least about 0.5 at about 20 µM after 48 hours of incubation identifies a compound with PDE10 inhibitory activity (and optionally PDE11 inhibitory activity based on a parallel study using a strain that expresses PDE11) and is useful in the methods, kits and compositions as disclosed herein.

Accordingly, therapeutic efficacy of a PDE11 inhibitor, such as any compound of formula (I)-(VI) as disclosed herein can be determined by standard therapeutic procedures in cell cultures or in animal models, e.g., for determining the $ED_{50}$ (the concentration of compound that produces 50% of the maximal effect). Once an agent has been determined to be a PDE11 inhibitor, or a dual PDE11/PDE inhibitor compound, the compound can optionally be further tested to confirm that it is effective in the therapeutic methods described herein. Such testing can be carried out in appropriate animal model systems for the conditions described herein, for example, rats with low cortisol levels, e.g., acd (adrenocortical dysplasia) mouse, where the mice can be administered a candidate PDE11 inhibitor, such as any compound of formula (I)-(VI) and the effects of the agent on various parameters associated with the conditions described herein can be compared with those in animals that have been kept under similar conditions, with the exception of not being treated with the candidate PDE11 inhibitor agent. Parameters that can be tested for this purpose include, for example, at least one of the following parameters include, measurement of cortisol release, measurement of free cortisol levels, measurement of total cortisol levels etc. A PDE11 inhibitor, such as any compound of formula (I)-(VI) which is identified to have a positive impact on at least one of these parameters, (e.g. increase one or more of cortisol release, free cortisol levels, and/or total cortisol levels) is suitable for use in the compositions, methods and kits as disclosed herein and can optionally be selected for testing in other pre-clinical or clinical studies, as can be determined by those of skill in this art.

The data obtained from cell culture assays and animal models can be used in formulating a range of dosage for use in humans. The dosage may vary depending upon the dosage form employed and the route of administration. For any compound used in the method of the invention, the therapeutically effective dose can be estimated initially from cell culture assays. A dose may be formulated in animal models to achieve a circulating plasma concentration range that includes the $IC_{50}$. Such information can be used to more accurately determine useful doses in humans. For example, levels of a PDE11 inhibitor, or levels of cortisol in plasma or urine may be measured, for example, by high performance liquid chromatography, or by other known methods in the art.

In some embodiments, the binding of a PDE11 inhibitor to a PDE11 protein can be assayed using a shift in the molecular weight or change in the biological activity of an unbound PDE11 protein. In some embodiments, a PDE11 inhibitor, such as any compound of formula (I)-(VI) as disclosed herein can be tested for binding with a PDE11 protein and/or modulating (e.g., inhibiting) the activity of a PDE11 protein.

Pharmaceutical Compositions, Formulations, Oral Compositions and Effective Doses.

Administration of a composition comprising a PDE11 inhibitor, such as any compound of formula (I)-(VI) as disclosed herein may be by oral, parenteral, sublingual, rectal, or enteral administration, or pulmonary absorption or topical application. Direct administration of a composition comprising a PDE11 inhibitor as disclosed herein to a subject can be by oral, parenteral, sublingual, rectal such as suppository or enteral administration, or by pulmonary absorption or topical application. Parenteral administration may be by intravenous (i.v.) injection, subcutaneous (s.c.) injection, intramuscular (i.m) injection, intra-arterial injection, intrathecal (i.t.) injection, intra-peritoneal (i.p) injection, or direct injection or other administration to the subject.

In addition to a composition comprising a PDE11 inhibitor, such as any compound of formula (I)-(VI) as disclosed herein, such compositions can optionally contain pharmaceutically-acceptable carriers and other ingredients known to facilitate administration and/or enhance uptake (e.g., saline, dimethyl sulfoxide, lipid, polymer, affinity-based cell specific-targeting systems). In some embodiments, a composition a composition comprising a PDE11 inhibitor as disclosed herein and/or salts thereof can be incorporated in a gel, sponge, or other permeable matrix (e.g., formed as pellets or a disk) and placed in proximity to the endothelium for sustained, local release. In some embodiments, a composition comprising a composition comprising a PDE11 inhibitor as disclosed herein and/or salts thereof can be administered in a single dose or in multiple doses which are administered at different times.

In some embodiments, compositions can be directly or indirectly administered to a subject or patient. In some embodiments, indirect administration is performed, for example, by administering a composition comprising a PDE11 inhibitor, such as any compound of formula (I)-(VI) as disclosed herein to cells ex vivo and subsequently introducing the treated cells to the subject, e.g., human patient. Alternatively, the cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

Alternatively, pharmaceutical compositions comprising a composition comprising a PDE11 inhibitor, such as any compound of formula (I)-(VI) as disclosed herein and/or salts thereof can be added to the culture medium of cells ex vivo.

Pharmaceutical compositions comprising a PDE11 inhibitor, such as any compound of formula (I)-(VI) as disclosed herein and/or salts thereof can be administered by any known route. By way of example, Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholicaqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. and/or salts thereof can be administered by a mucosal, pulmonary, topical, or other localized or systemic route (e.g., enteral and parenteral).

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the agents as disclosed herein such that it enters the animal's system and, thus, is subject to metabolism and other like processes, for example, subcutaneous administration.

Preparations for parenteral administration of a PDE11 inhibitor, such as any compound of formula (I)-(VI) as disclosed herein include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholicaqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert.

Preparations of a composition comprising a PDE11 inhibitor can be administered in effective amounts. Typically an effective amount of a PDE11 inhibitor can be determined by an ordinary physician, or in clinical trials, establishing an effective dose for a test population versus a control population in a blind study. An effective amount is that amount of a pharmaceutical preparation that alone, or together with further doses, stimulates the desired response. In the case of treating a disorder or condition that is associated with abnormal PDE11 activity and/or abnormal levels of cAMP, desired response is increasing cortisol levels, and/or increasing cortisol production or reducing a symptom of adrenal insufficiency. This may involve only slowing the progression of decrease in a symptom of adrenal insufficiency, or slowing the progression temporarily, although more preferably, it involves halting the progression of low cortisol levels permanently. An effective amount for treating a low cortisol level disease, or adrenal insufficiency or an associated disease or disorder is an amount that alters (e.g., increases) the amount of cortisol levels in the subject, and/or inhibits the activity of PDE11 enzyme, when the cell or subject is a cell or subject with a low cortisol levels, and/or adrenal insufficiency and/or a disease or disorder associated with adrenal insufficiency, with respect to that amount that would occur in the absence of the active compound.

In some embodiments, an effective amount is an amount of a PDE11 inhibitor, such as any compound of formula (I)-(VI) that increases cortisol in a subject, or diminishes or eliminates adrenal insufficiency and/or a disorder associated with adrenal insufficiency, or increases cortisol production from the adrenal gland or adrenocortical cells in the subject. Thus, an effective amount is an amount of a PDE11 inhibitor as disclosed herein, that when administered to a subject increases cortisol production in the subject, or increases the absolute cortisol levels in the serum of the subject as compared to without the administration of a PDE11-modulating compound e.g., a PDE11 inhibitor, such as any compound of formula (I)-(VI) as disclosed herein.

Oral Formulations

In some embodiments, administration of a composition comprising a PDE11 inhibitor, such as any compound of formula (I)-(VI) as disclosed herein can be formulated as an oral formulation. Alternatively, in some embodiments, a composition comprising at least one PDE11 inhibitor as disclosed herein and/or salts thereof can also be administered to the nasal passages as a spray. Sprays also provide immediate access to the pulmonary system and are the preferable methods for administering compositions immediately to the subject. Access to the gastrointestinal tract is gained using oral, enema, or injectable forms of administration. For example, administration of a composition comprising at least one PDE11 inhibitor, such as any compound of formula (I)-(VI) as disclosed herein and/or salts thereof to a subject is preferably oral. As a result, the subject can undergo administration of a composition comprising at least one PDE11 inhibitor as disclosed herein and/or salts at home.

As indicated above, orally active compositions comprising at least one PDE11 inhibitor as disclosed herein and/or salts thereof are preferred for at least a portion of the cycle of therapy, as oral administration is usually the safest, most convenient, and economical mode of drug delivery. Consequently, a composition as disclosed herein comprising a PDE11 inhibitor, such as any compound of formula (I)-(VI) as disclosed herein and/or salts thereof can be modified to increase their oral bioavailability by reducing or eliminating their polarity. This can often be accomplished by formulating a composition with a complimentary reagent that neutralizes its polarity, or by modifying the compound with a neutralizing chemical group. Oral bioavailability is also a problem, because drugs are exposed to the extremes of gastric pH and gastric enzymes. Accordingly, problems associated with oral bioavailability can be overcome by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

In some embodiments, an oral formulation of a composition comprising a PDE11 inhibitor as disclosed herein can comprise trappsol and/or captisol for stability, or alternatively cyclodextrin. In some embodiments, an oral formulation of a composition comprising a PDE11 inhibitor as disclosed herein comprises a preservative, for example, methylparaben, which can be used for example at a concentration of about 0.25% for the syrup formulation in the pH range of 6-7. Applicants recommend a preservative challenge test to be conducted at a later stage and a variety of different timepoints to determine the optimal concentration of methylparaben based on the results of the preservative challenge test.

In some embodiments, an oral formulation of a composition comprising a PDE11 inhibitor, such as any compound of formula (I)-(VI) as disclosed herein thereof can also comprise a sweetener, for example, an oral formulation can be formulated as a syrup using any sweetener commonly known to one of ordinary skill in the art, and in different combinations and percentage of the formulation. Exemplary sweeteners include, but are not limited to, Sucrose syrup, High Fructose Corn syrup, Sodium saccharin, Aspartame, Acesulfame and Sucralose. In some embodiments, an oral formulation of a PDE11 inhibitor as disclosed herein comprises at least one sweetener(s) or a combination of any sweeteners and a stabilizer, e.g., but not limited to Trappsol.

In some embodiments, an oral formulation of a composition comprising a PDE11 inhibitor, such as any compound of formula (I)-(VI) as disclosed herein and/or salts thereof comprises at least one, or any combination of High Fructose Corn syrup, Sodium saccharin, Aspartame, Acesulfame or Sucralose. Without wishing to be bound by theory, High Fructose corn syrup was found to have a better taste-masking effect than Sucrose syrup. Sodium saccharin was found to impart greater initial sweetness than Aspartame but provided a very bitter after-taste. Acesulfame by itself provided a good initial sweetness with bitter after-taste but in combination with Sucralose provided a lingering sweet after-taste.

In some embodiments, an oral formulation of a composition comprising a PDE11 inhibitor as disclosed herein and/or salts thereof can also comprise a flavor, for example, any flavor known to persons of ordinary skill in the art, for example, but without limitation, Cherry, Grape, Lemon, Pineapple, Orange, Menthol, Chocolate, Mint, Chocolate mint.

Enteric Coated Formulation

In some embodiments, a composition comprising a PDE11 inhibitor as disclosed herein can be formulated as tablets, for oral and/or enteral administration in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film—Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982, which are all incorporated herein in their entirety by reference.

Accordingly, in some embodiments oral formulations of a composition comprising a PDE11 inhibitor, such as any compound of formula (I)-(VI) as disclosed herein and/or salts thereof can be in the form of a tablet formulation, such as a tablet with an enteric polymer casing. An example of such a preparation can be found in WO2005/021002, which is incorporated herein in its entirety by reference. The active material in the core can be present in a micronised or solubilized form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilizers such as desiccating amorphous silica, coloring agents, flavors etc. In some embodiments, a tablet comprises lactose as diluent. When a binder is present, it is preferably hydroxypropylmethyl cellulose. In some embodiments, a tablet comprises magnesium stearate as lubricant. In some embodiments, a tablet comprises croscarmellose sodium as disintegrant, or can comprise a microcrystalline cellulose.

Examples of solid carriers include starch, sugar, bentonite, silica, and other commonly used carriers. Further non-limiting examples of carriers and diluents that can be used in the formulations of the present invention include saline, syrup, dextrose, and water.

In some embodiments, a diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

In some embodiments, a composition comprising a PDE11 inhibitor, such as any compound of formula (I)-(VI) comprises between 10 and 50% of the weight of the core, more preferably between 15 and 35% of the weight of the core (calculated as free base equivalent) as the PDE11 inhibitor. The core can contain any therapeutically suitable dosage level of the a PDE11 inhibitor, such as any compound of formula (I)-(VI) and/or a salt thereof, but preferably contains up to 150 mg as free base of the active ingredient. In some embodiments, the core contains 20, 30, 40, 50, 60, 80 or 100 mg as free base of the active ingredient. In some embodiments, a PDE11 inhibitor, such as any compound of formula (I)-(VI) and/or a salt thereof can be present as the free base, or as any pharmaceutically acceptable salt. If a PDE11 inhibitor is present as a salt, the weight is adjusted such that the tablet contains the desired amount of active ingredient, calculated as free base of the salt.

In some embodiments, the core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

In some embodiments, the core can be surrounded by a casing that comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional crosslinking agents such as epichlorohydrin, dichlorohydrin or 1, 2-, 3, 4-diepoxybutane. The casing can also include starch and/or dextrin.

In some embodiments, enteric coating materials are the commercially available EUDRAGIT™ enteric polymers such as EUDRAGIT™ L, EUDRAGIT™ S and EUDRAGIT™ NE, used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or CITROFLEX™ or CITROFLEX™ A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

In some embodiments, a casing can also include an anti-tack agent such as talc, silica or glyceryl monostearate. In some embodiments, an anti-tack agent is glyceryl monostearate. Typically, the casing can include around 5-25 wt % Plasticiser and up to around 50 wt % of anti tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material that can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an OPADRY coating, and particularly preferably it is Opadry White OY-S-28876.

In some embodiments, a PDE11 inhibitor, such as any compound of formula (I)-(VI) can be formulated as an enteric-coated formulation as described in WO2005/021002, which is incorporated herein in its entirety by reference, comprises varying amounts of one or more of a PDE11 inhibitors. Other enteric-coated preparations of this sort can be prepared by one skilled in the art, using these materials or their equivalents.

Other Formulations and Routes of Administration

In some embodiments, a PDE11 inhibitor, such as any compound of formula (I)-(VI) as disclosed herein can be used as a medicament, and the present invention encompasses methods for preparing such a medicament. In some embodiments, a medicament is prepared to allow sustained in vivo release of the medicament comprising a PDE11 inhibitor. Delivery systems can include time-release, delayed release or sustained release delivery systems, or as a pro-drug composition. Such systems can avoid repeated administrations of a pharmaceutical composition comprising a PDE11 inhibitor, such as any compound of formula (I)-(VI), and increase convenience to the subject and the physician.

Many types of release delivery systems are available and known to those of ordinary skill in the art. They include, but are not limited to, polymer-based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In one embodiment, a vehicle is a biocompatible microparticle or implant that is suitable for implantation into the mammalian recipient. Exemplary bioerodible implants that are useful in accordance with this method are described in PCT International application no. WO 95/24929, entitled "Polymeric Gene Delivery System", describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the compound(s) of the invention is encapsulated or dispersed within the biocompatible, preferably biodegradable polymeric matrix disclosed in WO 95/24929. The polymeric matrix preferably is in the form of a microparticle such as a microsphere (wherein the compound is dispersed throughout a solid polymeric matrix) or a microcapsule (wherein the compound is stored in the core of a polymeric shell).

Other forms of the polymeric matrix for containing the compounds of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery that is to be used. The polymeric matrix composition can be selected to have both favorable degradation rates and also to be formed of a material that is bioadhesive, to further increase the effectiveness of transfer when the device is administered to a vascular surface. The matrix composition also can be selected not to degrade, but rather, to release by diffusion over an extended period of time.

Both non-biodegradable and biodegradable polymeric matrices can be used to deliver agents and compounds of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, compositions comprising a PDE11 inhibitor, such as any compound of formula (I)-(VI) as disclosed herein can be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terephthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof. Examples of biodegradable polymers include synthetic polymers such as polymers of lactic acid and glycolic acid, polyanhydrides, poly(ortho) esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels may include, but are not limited to: polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

Use of a long-term sustained release implant comprising a PDE11 inhibitor, such as any compound of formula (I)-(VI) as disclosed herein can be particularly suitable for treatment of subjects with an established low cortisol, and/or adrenal insufficiency and/or a disease or disorder associated with adrenal insufficiency, or other cAMP PDE11-associated disease or disorder as well as subjects at risk of developing a such a disease or disorder. For example, mutations in PDE11 have been associated with Cushing's syndrome, asthma (e.g., allergy-asthma) and prostate cancer.

The "long-term" with respect to a long-term release formulation, as used herein, means that the implant is constructed and arranged to deliver therapeutic levels of a PDE11 inhibitor, such as any compound of formula (I)-(VI) as disclosed herein for at least about 7 days, and in some embodiments about 30-60 days, and in some embodiments, for 4-6 months, or for 6-12 months, or longer than 12 months, for example, several years. In some embodiments, an implant may be positioned at or near the site of the testis, but alternatively, can be positioned anywhere in the subject where the compounds are delivered to the systemic system or for physiological function to increase cortisol levels and/or increase production of cortisol from adrenal glands, e.g., adrenocortical cells. Long-term release implants can also be positioned near the adrenal glands to allow regional administration of a PDE11 inhibitor, such as any compound of formula (I)-(VI) as disclosed herein. Long-term sustained release implants are well known to those of ordinary skill in the art and include some of the release systems described above.

In some embodiments, the compositions as disclosed herein is administered to a subject using an infusion pump (to infuse, for example, the compositions as disclosed herein into the subject's circulatory system) is generally used intravenously, although subcutaneous, arterial, and epidural infusions are occasionally used. Injectable forms of administration are sometimes preferred for maximal effect. When long-term administration by injection is necessary, medi-ports, in-dwelling catheters, or automatic pumping mechanisms are also preferred, wherein direct and immediate access is provided to the arteries in and around the heart and other major organs and organ systems.

In some embodiments, a compositions comprising a PDE11 inhibitor, such as any compound of formula (I)-(VI) and/or salts thereof can be administered to a specific site may be by transdermal transfusion, such as with a transdermal patch, by direct contact to the cells or tissue, if accessible, or by administration to an internal site through an incision or some other artificial opening into the body.

Doses and Administration Regimens.

Suitable choices in amounts and timing of doses, formulation, and routes of administration of a composition comprising a PDE11 inhibitor as disclosed herein and/or salts thereof can be made with the goals of achieving a favorable response in the subject with low cortisol level and/or adrenal insufficiency, e.g., where a favorable response is an increase in the cortisol level of at least about 10% as compared to in the absence of such a compound, or an increase in the production of cortisol from adrenal glands e.g., adrenocortical cells present in the subject, and avoiding undue toxicity or other harm thereto (i.e., safety). Therefore, "effective" refers to such choices that involve routine manipulation of conditions to achieve a desired effect.

A bolus of the formulation of a composition comprising a PDE11 inhibitor, such as any compound of formula (I)-(VI) as disclosed herein and/or salts thereof can be administered to a subject over a short time period, for example, once a day is a convenient dosing schedule. Alternatively, an effective daily dose can be divided into multiple doses for purposes of administration, for example, two to twelve doses per day. Dosage levels of active ingredients in a pharmaceutical composition comprising a PDE11 inhibitor as disclosed herein and/or salts thereof can also be varied so as to achieve a transient or sustained concentration of the compound or derivative thereof in an individual, especially in and around the blood circulation and to result in the desired therapeutic response or protection. But it is also within the skill of the art to start doses at levels lower than required to achieve the desired therapeutic effect and to gradually increase the dosage until the desired effect is achieved.

In some embodiments, the amount of a composition comprising a PDE11 inhibitor as disclosed herein and/or salts thereof can be administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration, and the like. It will also be understood that the specific dose level to be achieved for any particular individual can depend on a variety of factors, including age, gender, health, medical history, weight, combination with one or more other drugs, and severity of disease.

Production of a composition comprising a PDE11 inhibitor as disclosed herein and/or salts thereof according to present regulations will be regulated for good laboratory practices (GLP) and good manufacturing practices (GMP) by governmental agencies (e.g., U.S. Food and Drug Administration). This requires accurate and complete record keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Dosages, formulations, dosage volumes, regimens, and methods for analyzing results of increased the production of cortisol and levels of cortisol in a subject can vary, e.g., on an individual subject-to-subject basis, as well as the time period of the day. Thus, minimum and maximum effective dosages of a composition comprising a PDE11 inhibitor as disclosed herein vary depending on the method of administration. Increase in cortisol levels in a subject can occur within a specific dosage range, which varies depending on, for example, the race, sex, gender, age, and overall health of the subject receiving the dosage, the route of administration, whether a composition comprising a PDE11 inhibitor as disclosed herein is administered in conjunction with other molecules, and the specific regimen of administration. For example, in general, nasal administration requires a smaller dosage than oral, enteral, rectal, or vaginal (if being administered to female) administration.

In some embodiments, a composition comprising a PDE11 inhibitor, such as any compound of formula (I)-(VI) is safe at effective dosages. Safe compositions refer to a composition that is not substantially toxic (e.g. cytotoxic or myelotoxic), or mutagenic at required dosages, do not cause adverse reactions or side effects, and are well-tolerated buy the subject. Although side effects may occur, a composition is generally considered safe if the benefits achieved from their use outweigh disadvantages that may be attributable to side effects. Unwanted side effects may include, but may not occur, frequent and/or sustained erections, nausea, vomiting, aggression, muscle development, baldness, hypersensitivity, allergic reactions, cardiovascular problems and other problems.

Compositions comprising a PDE11 inhibitor, such as any compound of formula (I)-(VI) as disclosed herein useful for treating adrenal insufficiency and/or low cortisol levels do not substantially affect the viability of a adrenal cells, e.g., adrenocortical cells or other cells in the adrenal gland. Normal cell viability of adrenal cells can be determined from analyzing the effects of the composition on one or more biological processes of the adrenal cell, e.g., adrenocortical cells (such as cortisol production) and release into the blood, or the normal biological process of the adrenal gland which are well known to persons of ordinary skill in the art, and include, for example, releasing hormones in response to stress (e.g., synthesis of corticosteroids such as cortisol and catecholamines such as epinephrine), and secretion of aldosterone, a hormone involved in regulating the osmolarity of blood plasma.

Useful combination therapies will be understood and appreciated by those of skill in the art. Potential advantages of such combination therapies include the ability to use less of each of the individual active ingredients to minimize toxic side effects, synergistic improvements in efficacy, improved ease of administration or use, and/or reduced overall expense of compound preparation or formulation.

Administration of a composition comprising a PDE11 inhibitor, such as any compound of formula (I)-(VI) as disclosed herein to a subject according to a method of the invention may be for prophylaxis, or alternatively, for therapeutic treatment of a subject diagnosed with low cortisol levels, and/or adrenal insufficiency, and/or a disease or disorder associated with adrenal insufficiency as disclosed herein.

In some embodiments, a composition comprising a PDE11 inhibitor as disclosed herein can be administered to an adult, an adolescent, a child, in some embodiments, although rarely, the subject can be a neonate, an infant or in utero.

In some embodiments, a composition comprising a PDE11 inhibitor as disclosed herein can be administered according to a specific dosing regimen, e.g., in a single or multiple doses, or continuous or sporadic, or as deemed necessary based on an administration regime as determined by measuring total cortisol levels and/or free cortisol levels in the subject as disclosed herein.

In some embodiments, a composition comprising a PDE11 inhibitor as disclosed herein can be administered to a subject via a continuous infusion throughout the cycle of therapy. Alternatively, a composition comprising at least one PDE11 inhibitor of any of formula (I)-(VI) as disclosed herein and/or salts thereof can be administered to a the subject over a single span of a few to several hours per day every day throughout the first period of the cycle of therapy.

Alternatively, in some embodiments a composition comprising a PDE11 inhibitor, such as any compound of formula (I)-(VI) can be administered to a subject in a single parenteral bolus, or orally, daily for several days throughout the treatment regimen or cycle, or weekly.

In some embodiments, the pharmaceutical compounds as disclosed herein comprising a PDE11 inhibitor can be administered alone, in combination with each other, and/or in combination with other drug therapies that are administered to subjects with PDE11-associated diseases or disorders, such as adrenal insufficiency or low cortisol levels.

In some embodiments a PDE11 inhibitor, such as any compound of formula (I)-(VI) can be administered in combination (e.g., concurrently or in conjunction) with an additional drug for treating adrenal insufficiency or a PDE11-associated disease or disorder, e.g., low cortisol levels, or cancer as disclosed herein. For example, a selective PDE11 inhibitor as described herein, can be administered alone or in combination with other suitable therapeutic agents useful in treating immune and inflammatory disorders such as immunosuppressants such as cyclosporins. In some embodiments, a PDE11 inhibitor can be administered with suitable therapeutic agents useful in treating cancer, e.g., chemotherapeutic agents which are well known to one of ordinary skill in the art.

In some embodiments, a composition comprising a PDE11 inhibitor, such as any compound of formula (I)-(VI) can be formulated with other agents, e.g., additional therapeutic agents. For example, where a PDE11 inhibitor as disclosed herein is being used to increase production of cortisol from adrenal cells (e.g., adrenocortical cells) and/or increase cortisol levels in a subject, a combination therapy can include administering a composition comprising a PDE11 inhibitor, such as any compound of formula (I)-(VI) as disclosed herein and/or salts thereof and an additional agent, e.g., catecholamines such as epinephrine. In some embodiments, an additional therapy is an anti-cancer treatment. Such an anti-cancer agent can be an agent that decreases growth of tumor after the anti-cancer effects of other therapies have decreased. The additional agent or therapy can also be another anti-viral or anti-cancer agent or therapy.

Additional compounds or additional agents and alternative drug therapies are well known to those of ordinary skill in the art and are administered by modes known to those of skill in the art. Thus, encompassed in the present invention are administration of additional agents in amounts which are not capable of preventing or reducing the physiological consequences of the adrenal insufficiency and/or an associated disease or disorder when such drug therapies are administered alone, but are capable of preventing or reducing the physiological consequences of adrenal insufficiency or an associated disease and/or disorder when administered in combination with a PDE11 inhibitor, such as any compound of formula (I)-(VI) as disclosed herein.

In some embodiments, a composition comprising a PDE11 inhibitor, such as any compound of formula (I)-(VI) can be used in prophylaxis treatment, for example, where the subject has been diagnosed with low cortisol levels, primary hypocortisolism, hypoadrenia, and/or adrenal insufficiency or a disease or disorder associated with adrenal insufficiency or likely to develop adrenal insufficiency, a subject can be administered a composition comprising at least one PDE11 inhibitor as disclosed herein and/or salts thereof prior to, or concurrent with or subsequent to, the chemotherapy or radiation therapy, in order to prevent development of low cortisol levels which typically occur as a side-effect of the chemotherapy or radiation therapy for or adrenocortical tumor treatment, or as a result of damage to the adrenal gland.

In some embodiments, a composition comprising a PDE11 inhibitor, such as any compound of formula (I)-(VI) as disclosed herein and/or salts thereof can be administered to a subject to augment the treatment of cancer, for example, where a subject is undergoing, or has undergone, or will undergo conventional cancer treatment, for example, chemotherapy, radiation therapy, antibody therapy, and/or other forms of cancer therapy. In some embodiments, the cancer is an adrenocortical tumor, or prostate cancer or any other cancer known to persons of ordinary skill in the art.

Conventional chemotherapeutic agents can be used in combination with the methods and compositions comprising a PDE11 inhibitor, such as any compound of formula (I)-(VI) as disclosed herein. Conventional chemotherapeutic agents are well known to persons of skill in the art, and include without limitation, cyclophosphamides such as alkylating agents, the purine and pyrimidine analogs such as mercaptopurine, the vinca and vinca-like alkaloids, the etoposides or etoposide-like drugs, the antibiotics such as deoxyrubocin and bleomycin, the corticosteroids, the mutagens such as the nitrosoureas, antimetabolites including methotrexate, the platinum based cytotoxic drugs, the hormonal antagonists such as anti-insulin and anti-androgen, the anti-estrogens such as tamoxifen, and other agents such as doxorubicin, L-asparaginase, DTIC, mAMSA, procarbazine, hexamethylmelamine, and mitoxantrone.

In some embodiments, a composition comprising a PDE11 inhibitor, such as any compound of formula (I)-(VI) as disclosed herein and/or salts thereof can be administered to a subject in combination with other therapeutic procedures or surgeries for cancer treatment such as curative tumor ressection, intralesional ethanol injection, chemoembolization, radiofrequency ablation, cryosurgery, radiation therapy, percutaneous intralesional ethanol injection, transarterial chemoembolization, radiotherapy, systemic chemotherapy and surgery.

In some embodiments, a composition comprising a PDE11 inhibitor as disclosed herein can be administered to a subject in combination with, e.g., simultaneously with, or subsequently after treatment with other chemotherapeutic agents, such as Doxorubicin, 5-FU, Paclitaxel, Irinotecan, Patupilone, Everolimus, multikinase inhibitors (Sorafenib and Sunitinib), and EGFR inhibitors (Cetuximab, Erlotinib, Gefitinib, Brivanib, Lapatinib). A PDE11 inhibitor, such as any compound of formula (I)-(VI) can also be administered after surgery or after the other aforementioned treatments of cancer, e.g., where solid tumors have been removed to prevent cancer recurrence or metastasis.

These chemotherapeutic agents could be given simultaneously, or alternately as defined by a protocol in combination with composition comprising a PDE11 inhibitor, such as any compound of formula (I)-(VI) as disclosed herein to a subject designed to maximize effectiveness, but minimize toxicity to the patient's body.

In some embodiments, a composition comprising as disclosed herein can be prepared in solution as a dispersion, mixture, liquid, spray, capsule, or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil, or a relatively inert solid or liquid. Liquids, pills, capsules or tablets administered orally may also include flavoring agents to increase palatability. Additionally, in some embodiments, a composition comprising a PDE11 inhibitor as disclosed herein can further comprise agents to increase shelf-life, such as preservatives, anti-oxidants, and other components necessary and suitable for manufacture and distribution of the composition. A composition comprising a PDE11 inhibitor, such as any compound of formula (I)-(VI) as disclosed herein can further comprise a pharmaceutically acceptable carrier or excipient. Carriers are chemical or multi-chemical compounds that do not significantly alter or affect the active ingredients of the compositions. Examples include water, alcohols such as glycerol and polyethylene glycol, glycerin, oils, salts such as sodium, potassium, magnesium, and ammonium, fatty acids, saccharides, or polysaccharides. Carriers may be single substances or chemical or physical combinations of these substances.

In some embodiments, a composition comprising a PDE11 inhibitor as disclosed herein can be used in combination with other agents to maximize the effect of the compositions administered in an additive or synergistic manner. Accordingly, a composition comprising a PDE11 inhibitor as disclosed herein can also comprise proteinaceous agents such as growth factors and/or cytokines. Such proteinaceous agents may also be aminated, glycosylated, acylated, neutralized, phosphorylated, or otherwise derivatized to form compositions that are more suitable for the method of administration to the patient or for increased stability during shipping or storage.

A composition comprising a PDE11 inhibitor as disclosed herein can be physiologically stable at therapeutically effective concentrations. Physiological stable PDE11 inhibitors, such as any compound of formula (I)-(VI) as disclosed herein or salts thereof not break down or otherwise become ineffective upon administration to a subject or prior to having a desired effect. A PDE11 inhibitor, such as any compound of formula (I)-(VI) as disclosed herein can be structurally resistant to catabolism, and, thus, physiologically stable, or coupled by electrostatic or covalent bonds to specific reagents to increase physiological stability. Such reagents include amino acids such as arginine, glycine, alanine, asparagine, glutamine, histidine, or lysine, nucleic acids including nucleosides or nucleotides, or substituents such as carbohydrates, saccharides and polysaccharides, lipids, fatty acids, proteins, or protein fragments. Useful coupling partners include, for example, glycol, such as polyethylene glycol, glucose, glycerol, glycerin, and other related substances.

Physiological stability of a PDE11 inhibitor, such as any compound of formula (I)-(VI) as disclosed herein can be measured from a number of parameters such as the half-life of the PDE11 inhibitor, or the half-life of active metabolic products derived from a PDE11 inhibitor. In some embodiments, a PDE11 inhibitor, such as any compound of formula (I)-(VI) can have an in vivo half-live of greater than about 1 day, or 2 days, or 3 days, or 5 days, or about 7 days, or longer than about 7 days. A PDE11 inhibitor, such as any compound of formula (I)-(VI) can be considered stable using this criteria, however, physiological stability can also be measured by observing the duration of biological effects on the patient. Preferably, a stable composition comprising a PDE11 inhibitor, such as any compound of formula (I)-(VI) has an in vivo half-life of greater than about 24 hours, a serum half-life of greater than about 24 hours, or a biological effect which continues for greater than 24 hours after treatment has been terminated or the serum level of the compound has decreased by more than half.

Preferably, a PDE11 inhibitor, such as any compound of formula (I)-(VI) as disclosed herein is not significantly biotransformed, degraded, or excreted by catabolic processes associated with metabolism. Although there may be some biotransformation, degradation, or excretion, these functions are not significant, if the composition is able to exert its desired effect.

In some embodiments, a composition comprising a PDE11 inhibitor, such as any compound of formula (I)-(VI) as disclosed herein can additionally comprise chemicals that are substantially non-toxic. Substantially non-toxic means that the composition, although possibly possessing some degree of toxicity, is not harmful to the long-term health of the subject. Although the active component of the composition may not be toxic at the required levels, there may also be problems associated with administering the necessary volume or amount of the final form of the composition to the patient. For example, if composition comprising a PDE11 inhibitor contains a salt, although the active ingredient may be at a concentration that is safe and effective, there can be a harmful build-up of sodium, potassium, or another ion. With a reduced requirement for the composition or at least the active component of that composition, the likelihood of such problems can be reduced or even eliminated. Consequently, although subjects may suffer minor or short term detrimental side-effects, the advantages of taking the composition outweigh the negative consequences.

The amount of a composition comprising a PDE11 inhibitor, such as any compound of formula (I)-(VI) can be combined with a carrier material to produce a single dosage form will generally be that amount of the compound that produces a therapeutic effect. Generally out of one hundred percent, this amount will range from about 0.01% to 99% of the compound, preferably from about 5% to about 70%, most preferably from 10% to about 30%.

The data obtained from the cell culture assays and animal studies can be used in formulating a range of dosage for use in humans. The dosage of such compounds lies preferably within a range of circulating concentrations that include the $ED_{50}$ (the dose therapeutically effective in 50% of the population) with little or no toxicity. The dosage may vary within this range depending upon the dosage form employed and the route of administration utilized.

The therapeutically effective dose can be estimated initially from cell culture assays, for example the yeast growth assay as disclosed herein in the Examples, for example by measuring OD or yeast growth after 48 hrs of incubation with a PDE11 inhibitor, such as any compound of formula (I)-(VI) in the presence of 5FOA media. Alternatively, a dose may be formulated in animal models of low cortisol levels, and/or adrenal insufficiency e.g., an acd (adenocortical dysplasia) mouse model of adrenal insufficiency to achieve a circulating plasma concentration range that includes the $IC_{50}$ (i.e., the concentration of the therapeutic which achieves a half-maximal inhibition of symptoms) as determined in cell culture. Levels of the compound and/or cortisol levels in plasma and/or may be measured, for example, by high performance liquid chromatography or other methods commonly known to persons in the art and disclosed herein. The effects of any particular dosage of a PDE11 inhibitor can be monitored by a suitable bioassay.

The pharmaceutical compound dosage of a PDE11 inhibitor, such as any compound of formula (I)-(VI) as disclosed herein may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days. It will be recognized by those of skill in the art that some of the PDE11 inhibitors may have detrimental effects at high amounts. Thus, an effective amount for use in the methods of the invention may be optimized such that the amount administered results in minimal negative side effects and maximum PDE11 inhibition, and/or increase in cortisol production and/or reduce at least one symptom of adrenal insufficiency.

The absolute amount of a PDE11 inhibitor will depend upon a variety of factors, including the material selected for administration, whether the administration is in single or multiple doses, and individual subject parameters including age, physical condition, size, weight, and the stage of the disease or disorder. These factors are well known to those of ordinary skill in the art and can be addressed with no more than routine experimentation.

Accordingly, the dosage of a PDE11 inhibitor, such as any compound of formula (I)-(VI) can be determined by a physician and adjusted, as necessary, to suit observed effects of the treatment (e.g., an increase in cortisol levels). Generally, the compositions are administered so that a PDE11 inhibitor of any of formula (I)-(VI) or a prodrug thereof is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, a PDE11 inhibitor as disclosed herein can be administered at a dosage so that the compound has an in vivo, e.g., serum or blood, concentration of less than 500 nM, less than 400 nM, less than 300 nM, less than 250 nM, less than 200 nM, less than 150 nM, less than 100 nM, less than 50 nM, less than 25 nM, less than 20 nM, less than 10 nM, less than 5 nM, less than 1 nM, less than 0.5 nM, less than 0.1 nM, less than 0.05 nM, less than 0.01 nM, less than 0.005 nM, or less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs, or 24 hrs, or 48 hours or more from the time of administration.

Regimens of Administration of a Composition Comprising a PDE11 Inhibitor

In some embodiments, treatment of a subject with a composition comprising a PDE11 inhibitor, such as any compound of formula (I)-(VI) can be according to the methods as disclosed herein can be for a therapeutic treatment, e.g., a method of treatment of a low cortisol levels and/or adrenal insufficiency and/or a disease or disorder associated with adrenal insufficiency in a subject. In some embodiments, therapeutic treatment involves administration of a composition comprising a PDE11 inhibitor as disclosed herein according to the methods as disclosed herein to a patient suffering from one or more symptoms of or having been diagnosed as being afflicted with a low cortisol levels or adrenal insufficiency or a disease or disorder associated with adrenal insufficiency as disclosed herein. Relief and even partial relief from one or more of a symptom of adrenal insufficiency may correspond to decreased abdominal pains, decreased diarrhea, decreased vomiting, increased muscle strength, increased blood pressure, increased weight gain, decreased stress and increased interest in life or, simply, an increased quality of life. Further, treatments that alleviate a pathological symptom can allow for other treatments to be administered.

In alternative embodiments, the treatment of a subject can be according to the methods with a composition comprising a PDE11 inhibitor, such as any compound of formula (I)-(VI) can be a prophylactic treatment, for example, to prevent adrenal insufficiency, e.g., where a subject has hypoadrenia (adrenal fatigue) or has damage or injury to the adrenal gland or adenocortical cells. In some embodiments, a subject has cancer, and has or will undergo cancer treatment, such as for example chemotherapy, radiotherapy, resection or removal of the cancer and the like. In some embodiments, prophylactic treatments involve administration of a PDE11 inhibitor, such as any compound of formula (I)-(VI) to a subject having a been recommended to have, or having undergone a treatment for an adreocortisol tumor, where it is desirable to prevent the decrease in cortisol levels in the subject as a side-effect of the cancer treatment or cancer removal. Administration of a PDE11 inhibitor can begin at the beginning or after, or during (e.g., concurrent with) administration of a cancer therapy (e.g., chemotherapy, radiation therapy) etc., and can continue, if necessary, after cancer treatment, and if necessary for the remaining life of the subject. In some embodiments, prophylactic treatment is useful where a subject is likely to be exposed to radiation, for example, subjects who are in or located near an area of a radiation disaster accident, or subjects who are working in a recovery effort in an area that has had a radiation disaster or working in or near a radiation exposure. As demonstrated herein, both prophylactic and therapeutic uses are readily acceptable, because these compounds are generally safe and non-toxic.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, as determined by the subject's sensitivity or responsiveness to the PDE11 inhibitor. A desired dose can be administered every day or every third, fourth, fifth, or sixth day. The desired dose can be administered at one time or divided into sub doses, e.g., 2-4 sub doses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, administration of a composition comprising a PDE11 inhibitor, such as any compound of formula (I)-(VI) can be intermittent; for example, administration can be once every two days, every three days, every five days, once a week, once or twice a month, and the like. The amount or form of a composition comprising a PDE11 inhibitor can be varied at different times of administration.

Pulsed administration of one or more pharmaceutical compositions comprising a PDE11 inhibitor, such as any compound of formula (I)-(VI) can be used for the treatment of a adrenal insufficiency or low cortisol levels, and/or a disease or disorder associated with adrenal insufficiency in a subject, e.g., but not limited to Addison's disease, Nelson's syndrome, primary hypocortisolism, congenital adrenal hyperplasia, adenocortical tumors etc. In some embodiments, pulsed administration of one or more pharmaceutical compositions comprising a PDE11 inhibitor can be used to stimulate or increase production of cortisol in a subject. Similarly, pulsed administration of one or more pharmaceutical compositions comprising a PDE11 inhibitor, such as any compound of formula (I)-(VI) can be used for prophylactic treatment, e.g., for example, a subject who will, or has or is currently undergoing chemotherapy and chemoradiation therapy, in particular, where the subject has cancer. In some embodiments, pulsed administration can be more effective than continuous treatment as pulsed doses results in an overall lower amount of compound used than would be expected from continuous administration of the same composition. Each pulse dose can be reduced and the total amount of drug administered over the course of treatment to the patient can be minimized.

With pulse therapy, in vivo levels of a PDE11 inhibitor, such as any compound of formula (I)-(VI) can drop below that level required for effective continuous treatment. Pulsed administration can reduce the amount of a PDE11 inhibitor administered to the patient per dose, and/or per total treatment regimen with an increased effectiveness. Pulsed administration can provide a saving in time, effort and expense and a lower effective dose can lessen the number and severity of complications that can be experienced by a subject. As such, pulsing can be more effective than continuous administration of the same composition.

In some embodiments, individual pulses can be delivered to a subject continuously over a period of several hours, such as about 2, 4, 6, 8, 10, 12, 14 or 16 hours, or several days, such as 2, 3, 4, 5, 6, or 7 days, or from about 1 hour to about 24 hours or from about 3 hours to about 9 hours. Alternatively, periodic doses can be administered in a single bolus or a small number of injections of PDE11 inhibitor and/or salts thereof over a short period of time, for example, less than 1 or 2 hours. For example, a PDE11 inhibitor, such as any compound of formula (I)-(VI) can be administered over a period of 4 days with infusions for about 8 hours per day or overnight, followed by a period of 7 days of no treatment.

In some embodiments, an interval between pulses of administration or the interval of no delivery can be greater than 24 hours or can be greater than 48 hours, and can be for even longer such as for 3, 4, 5, 6, 7, 8, 9 or 10 days, two, three or four weeks or even longer. The interval between pulses can be determined by one of ordinary skill in the art, for example, as demonstrated herein in the Examples, by measuring cortisol levels (e.g., total cortisol and/or free cortisol) in the subject in the plasma, and/or urine after administration of the pulse dose, and administering a pulse when the cortisol level reaches a certain pre-defined low threshold limit. Such pre-defined low threshold limits can be determined by one of ordinary skill in the art, and can be, for example, about between 140-700 nmol/L (or 5-25 μg/dL) of plasma free cortisol at about 9:00 am in the morning, or about between about 80-350 nmol/L (or 2.9-13 μg/dL) of free cortisol in the plasma at about midnight. Alternatively, the pre-defined levels can be between about 28-30 and 280-490 nmol/24 hrs (or 10-11 to 100-176 μg/24 hrs) of free cortisol in the urine (as detected by urinalysis). Alternatively, in some embodiments, the interval between pulses can be calculated by administering another dose of a composition comprising at least one PDE11 inhibitor of any of formula (I)-(VI) and/or salts thereof, and when the active compound of the composition is no longer detectable in the subject prior to delivery of the next pulse. Alternatively, intervals can also be calculated from the in vivo half-life of the compound present in the composition. For example, doses can be determined by the bioavailability of a PDE11 inhibitor, where it is available for at least about 12 hours after administration, or at least about 48 hours after administration. Accordingly, intervals can be calculated as greater than the in vivo half-life, or 2, 3, 4, 5 and even 10 times greater than the functional or composition half-life. Intervals can be 25, 50, 100, 150, 200, 250 300 and even 500 times the half-life of the bioavailability of PDE11 inhibitor.

In some embodiments, the number of pulses in a single therapeutic regimen can be as little as two, but can be from about 5 to 10, 10 to 20, 15 to 30 or more.

In some embodiments, a subject can receive one or more compositions comprising at least one PDE11 inhibitor as disclosed herein for life according to the methods of this invention, for example, where the subject has a permanent or incurable adrenal insufficiency, e.g., where the subject has had damage and/or removal of the adrenal gland, has an inherited genetic congenital adrenal hyperplasia, or is in need of continuous treatment with a hydrocortisone treatment. Compositions can be administered by most any means, and can be delivered to the subject as an oral formulation, or injection (e.g. intravenous, subcutaneous, intraarterial), infusion or instillation. Various methods and apparatus for pulsing compositions by infusion or other forms of delivery to the patient are disclosed in U.S. Pat. Nos. 4,747,825; 4,723,958; 4,948,592; 4,965,251 and 5,403,590, which are incorporated herein in their entirety by reference.

In one embodiment, a composition comprising a PDE11 inhibitor as disclosed herein can be administered to a subject for about 2, or about 3, or about 4, or about five days, or more than five days, and then a subsequently administered after an appropriate interval for an additional period of time, for example, for about 2, or about 3, or about 4, or about five days, or more than five days. Cycles of treatment may occur in immediate succession or with an interval of no treatment between cycles.

In some embodiments, a composition comprising a PDE11 inhibitor, such as any compound of formula (I)-(VI) can be administered to a subject before development of adrenal insufficiency, or before a chemotherapeutic treatment, or radiation treatment is administered to the subject. As discussed previously, in alternative embodiments, a composition comprising a PDE11 as disclosed herein can be co-administered to a subject concurrently with another agent or treatment regimen, e.g., concurrently with a chemotherapeutic treatment, or radiation treatment, or co-administered with a pharmaceutical composition comprising an comprising one or more additional agents. In some embodiments, a composition comprising a PDE11 inhibitor can be provided by pulsed administration. For example, a composition comprising a PDE11 inhibitor, such as any compound of formula (I)-(VI) can be administered to a subject, followed by a chemotherapeutic treatment, or radiation treatment after an interval of time has passed, and this order of administration the same or similar time interval can be repeated, for example, at least 1, 2, 3, 4, 5, 6, 7, 8, 9, or 10 or more times.

In some embodiments, a composition comprising a PDE11 inhibitor, such as any compound of formula (I)-(VI) can be administrated to a subject in combination with one or more pharmaceutically active agents. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

Low Cortisol Levels and Adrenal Insufficiency and Subjects Amenable to Treatment.

In one embodiment, the invention relates to compositions useful in elevating cortisol levels and/or increasing cortisol production in a subject, e.g., a subject with low cortisol levels and/or adrenal insufficiency. Subjects amenable to treatment typically have adrenal insufficiency or a disease or disorder associated with adrenal insufficiency, as well as subjects with hypoadrenia (adrenal fatigue).

In some embodiments, a subject amenable to treatment according to the methods and compositions as disclosed herein has a free plasma cortisol level of less than 140 nmol/L (or 5 μg/dL) at about 9:00 am in the morning, or a free plasma cortisol level of less than about 80 nmol/L (or 2.9 μg/dL) at about midnight. Alternatively, a subject amenable to treatment with the methods and compositions as disclosed has a level of cortisol in the urine of less than about 28 nmol/24 hrs (or less than about 10-11 μg/24 hrs) (as detected by urinalysis).

In some embodiments, a PDE11 inhibitor as disclosed herein can be used in methods for the treatment of disorders and diseases of the thyroid that result in adrenal insufficiency and/or low levels of adrenal steroids. In some embodiments, a subject amenable to treatment with a PDE11 inhibitor, such as any compound of formula (I)-(VI) as disclosed herein have low cortisol levels, primary hypocortisolism and/or adrenal insufficiency or a disease or disorder associated with adrenal insufficiency or likely to develop adrenal insufficiency.

Without wishing to be bound by theory, cortisol (hydrocortisone) is a steroid hormone, or glucocorticoid, produced by the adrenal gland. It is released in response to stress and a low level of blood glucocorticoids. Its primary functions are to increase blood sugar through gluconeogenesis; suppress the immune system; and aid in fat, protein and carbohydrate metabolism. It also decreases bone formation.

Various synthetic forms of cortisol are used to treat a variety of diseases. Accordingly, a subject amenable to treatment to treatment with a PDE11 inhibitor, such as any compound of formula (I)-(VI) as disclosed herein can be a subject normally treated with a synthetic form of cortisol.

Cortisol is produced by the adrenal gland in the zona fasciculata, the second of three layers comprising the outer adrenal cortex. This release is controlled by the hypothalamus, a part of the brain. The secretion of corticotropin-releasing hormone (CRH) by the hypothalamus triggers anterior pituitary secretion of adrenocorticotropic hormone (ACTH). ACTH is carried by the blood to the adrenal cortex, where it triggers glucocorticoid secretion. Most serum cortisol (all but about 4%) is bound to proteins, including corticosteroid binding globulin (CBG) and serum albumin. Free cortisol passes easily through cellular membranes, where they bind intracellular cortisol receptors.

The primary control of cortisol is the pituitary gland peptide, adrenocorticotropic hormone (ACTH). ACTH probably controls cortisol by controlling the movement of calcium into the cortisol-secreting target cells. ACTH is in turn controlled by the hypothalamic peptide corticotropin releasing hormone (CRH), which is under nervous control. CRH acts synergistically with arginine vasopressin, angiotensin II, and epinephrine. When activated macrophages start to secrete interleukin-1 (IL-1), which synergistically with CRH increases ACTH, T-cells also secrete glucosteroid response modifying factor (GRMF or GAF) as well as IL-1; both increase the amount of cortisol required to inhibit almost all the immune cells. Immune cells then assume their own regulation, but at a higher cortisol setpoint.

Cortisol has a negative feedback effect on interleukin-1. The suppressor immune cells are not affected by GRMF, so the immune cells' effective setpoint may be even higher than the setpoint for physiological processes. GRMF (known as GAF in this reference) primarily affects the liver (rather than the kidneys) for some physiological processes.

Cortisol has many functions, including, but not limited to increasing blood sugar through gluconeogenesis, suppressing the immune system, aiding in fat, protein, and carbohydrate metabolism, and suppresses the immune system. Another function is to decrease bone formation.

Cortisol is used to treat diseases such as Addison's disease, inflammatory and rheumatoid diseases, and allergies. Low-potency hydrocortisone can be used to treat skin problems such as rashes, eczema and others. Accordingly, in some embodiments, a subject amenable to treatment with a PDE11 inhibitor, such as any compound of formula (I)-(VI) as disclosed herein can be a subject with one or more of Addison's disease, inflammatory and rheumatoid diseases, and allergies.

Cortisol also prevents the release of substances in the body that cause inflammation. It stimulates gluconeogenesis (the breakdown of protein and fat to provide metabolites that can be converted to glucose in the liver) and it activates anti-stress and anti-inflammatory pathways. Accordingly, in some embodiments, a subject amenable to treatment with a PDE11 inhibitor, such as any compound of formula (I)-(VI) as disclosed herein can be a subject with one or more of high anxiety, inflammation and obesity.

Changed patterns of serum cortisol levels have been observed in connection with abnormal ACTH levels, clinical depression, psychological stress, and physiological stressors such as hypoglycemia, illness, fever, trauma, surgery, fear, pain, physical exertion, or temperature extremes. Cortisol levels may also differ for individuals with autism or Asperger's syndrome. Accordingly, in some embodiments, a subject amenable to treatment with a PDE11 inhibitor, such as any compound of formula (I)-(VI) as disclosed herein can be a subject where it is desirable to increase cortisol production in a subject with one or more of clinical depression, psychological stress, and/or been exposed to physiological stressors such as hypoglycemia, illness, fever, trauma, surgery, fear, pain, physical exertion, or temperature extremes.

In some embodiments, a subject amenable to treatment with a PDE11 inhibitor, such as any compound of formula (I)-(VI) as disclosed herein has adrenal insufficiency also known in the art as hypocortisolism, where there are insufficient levels of cortisol in the blood.

Adrenal Insufficiency:

Adrenal insufficiency is a condition in which the adrenal glands do not produce adequate amounts of steroid hormones, primarily cortisol, which regulates sodium, potassium and water retention, but may also include impaired aldosterone production (a mineralcorticoid) which regulates sodium, potassium and water retention. Craving for salt or salty foods due to the urinary losses of sodium is common.

There are two types of adrenal insufficiency, primary and secondary. The age at diagnosis of primary adrenal insufficiency peaks in the fourth decade of life, with women more frequently affected than men. Secondary adrenal insufficiency has an estimated prevalence of 150-280 per million and also affects women more frequently than men. Age at diagnosis peaks in the sixth decade of life.

Addison's disease and congenital adrenal hyperplasia manifest as adrenal insufficiency. The reported incidence of Addison disease is 5 or 6 cases per million population per year, with a prevalence of 60-110 cases per million population. Adrenal insufficiency is considered a rare disorder, affecting less than 200,000 people in the US, and is given orphan drug status in the US.

Currently, treatment for adrenal insufficiency is glucocorticoid replacement given in two or three daily doses, with a half to two-thirds of the daily dose administered in the mornings to mimic the physiological cortisol secretion pattern. Glucocorticoid replacement is provided through administration of hydrocortisone (cortisol) or cortisone acetate.

Mineralocorticoid replacement, only required in primary adrenal insufficiency, may also be required and is provided through the oral administration of fludrocortisone.

Addison's disease and congenital adrenal hyperplasia, and rescission after an adrenocortical tumor, etc., can manifest as adrenal insufficiency. If not treated, adrenal insufficiency may result in severe abdominal pains, diarrhea, vomiting, profound muscle weakness and fatigue, depression, extremely low blood pressure (hypotension), weight loss, kidney failure, changes in mood and personality, and shock (adrenal crisis). An adrenal crisis often occurs if the body is subjected to stress, such as an accident, injury, surgery, or severe infection; death may quickly follow.

Accordingly, in some embodiments, a subject amenable to treatment with a PDE11 inhibitor, such as any compound of formula (I)-(VI) as disclosed herein has adrenal insufficiency (primary and/or secondary), e.g., idiopathic adrenal insufficiency, or Addison's disease or autoimmune adrenalitis, congenital adrenal hyperplasia, and removal of part or whole of the adrenal gland after an adrenocortical tumor. In some embodiments, a subject has an adenocortical tumor associated with Cushing's syndrome, where part or whole of the subject's adrenal gland is removed after an adrenocortical tumor.

There are two major types of adrenal insufficiency. Primary adrenal insufficiency is due to impairment of the adrenal glands. One subtype is called idiopathic or unknown cause of adrenal insufficiency. 80% of subjects with adrenal insufficiency have an autoimmune disease called Addison's disease or autoimmune adrenalitis. Other cases are due to congenital adrenal hyperplasia or an adenoma (tumor) of the adrenal gland (e.g., referred to as adenocortical tumors herein).

Secondary adrenal insufficiency is caused by impairment of the pituitary gland or hypothalamus. These can be due to a form of cancer: a pituitary microadenoma, or a hypothalamic tumor; Sheehan's syndrome, which is associated with impairment of only the pituitary gland; or a past head injury.

Secondary adrenal insufficiency can also occur when the hypothalamus or the pituitary gland, both located at the base of the skull, does not make adequate amounts of the hormones that assist in regulating adrenal function, and is caused by lack of production of ACTH in the pituitary or lack of CRH in the hypothalamus.

Tertiary adrenal insufficiency is due to hypothalamic disease and decrease in corticotropin releasing factor (CRF).

A subject with adrenal insufficiency can be identified by an ordinary physician, and can be identified as a subject having one or more symptoms including, but not limited to, hypoglycemia, dehydration, weight loss, and disorientation. He or she may experience weakness, tiredness, dizziness, low blood pressure that falls further when standing (orthostatic hypotension), muscle aches, nausea, vomiting, and diarrhea. These problems may develop gradually and insidiously. Addison's can present with tanning of the skin that may be patchy or even all over the body. Characteristic sites of tanning are skin creases (e.g. of the hands) and the inside of the cheek (buccal mucosa). Goitre and vitiligo may also be present in a subject with adrenal insufficiency. Insulin tolerance test is another test used to identify sub-types of adrenal insufficiency.

Causes of acute adrenal insufficiency include, but are not limited to, Waterhouse-Friderichsen syndrome, sudden withdrawal of long-term corticosteroid therapy and stress in patients with underlying chronic adrenal insufficiency (e.g., critical illness-related corticosteroid insufficiency).

Without wishing to be bound by theory, corticosteroids such as cortisone, prednisone, and methylprednisolone are used to treat a large number of inflammatory conditions. However their prolonged use can lead to adrenal suppression in which the adrenal gland produces an insufficient amount of cortisol or other adrenal steroids upon cessation of the treatment. In one study, one-third of participants displayed adrenal suppression three weeks after completing a two-week treatment with prednisone (Neidert, Schuetz et al. 2010). Complications due to adrenal suppression are seen in children who have undergone steroid treatment for acute lymphoblastic leukemia (Einaudi, Bertorello et al. 2008) and even in newborn infants as a result of their mothers' therapeutic treatment (Kurtoglu, Sarici et al. 2011). The responses of patients to corticosteroid treatment as well as to tapers of the treatment in an effort to minimize secondary adrenal insufficiency and the possibility of a later adrenal crisis are highly variable (Alves, Robazzi et al. 2008). The corticosteroids interfere with the hypothalamic-pituitary-adrenal axis to reduce production of the pituitary adrenocorticotropic hormone (ACTH) that triggers a cAMP-mediated increase in cortisol release by the adrenal gland (Mims 1977; Cote, Guillon et al. 2001). Thus, a drug that elevates adrenal cAMP levels to stimulate cortisol release in the absence of ACTH signaling could prevent or reduce the suppression of adrenal gland function associated with prolonged exposure to corticosteroids, and could be an important addition to such therapeutic regimes.

Accordingly, in some embodiments, the present invention also relates to the use of compounds of formula (I)-(VI), such as but not limited to, compounds BC11-15, BC11-19, BC11-28 and BC11-38, and derivatives and analogues thereof in methods to elevate cortisol levels in a subject who has adrenal suppression, for example, where a subject is being treated with a corticosteroid, or on long-term corticosteroid treatment. In some embodiment, a subject who is on long-term corticosteroid treatment is administered a composition comprising at least one of any of compounds of BC11-15, BC11-19, BC11-28 and BC11-38. In some embodiments, a subject is administered a compound of formula (I) as disclosed herein, e.g., selected from any of the group of BC11-38, or analogues thereof such as BC-11-38-1, BC11-38-2, BC11-38-3 or BC11-38-4 where the subject is also being administered a corticosteroid. In some embodiments, a compound of formula (I), such as BC11-38 or analogues thereof are selected based on the most effective inhibition of PDE11, for example, a $IC_{50}$ of at or below 5.0 μM. In some embodiments, a subject is also being administered a corticosteroid is administered a compound of formula (I) is selected from BC11-38, or analogues thereof such as BC-11-38-1, BC11-38-2, which have a $IC_{50}$ of inhibition of PDE11 at or below about 5.0 μM, or about at least 2.5 μM. The administration of a PDE11 inhibitor in the methods as disclosed herein can be concurrently with, prior to or after administration of a corticosteroid to the subject. In some embodiments, the corticosteroid is cortisone, prednisone or methylprednisolone, prednisolone, beclamethasone, betamethasone, dexamethasone, fludrocortisone, hydrocortisone and triamcinolone or analogues or variants thereof. In some embodiments, the PDE11 inhibitor as disclosed herein is being administered in combination with a corticosteroid, e.g., in the same composition.

In some embodiments, the compounds of formula (I)-(VI), e.g., any of compound of BC11-15, BC11-19, BC11-28 and BC11-38 or analogues thereof can be co-administered with a steroid, such as a corticosteroids, glucocorticoid or cortisones. These steroid are synthetic derivatives of the natural steroid, cortisol, which is produced by the adrenal glands. The steroid can be a systemic steroid (e.g., a steroid which are taken by mouth or given by intramuscular injection), a topical steroid (e.g., a (cortico)steroid applied directly to the skin) or an inhaled steroid (which is where the steroid is breathed in).

Systemic steroids which can be co-administered with a compound of formula (I)-(VI), e.g., any of compound of BC11-15, BC11-19, BC11-28 and BC11-38 or analogues thereof include prednisone, prednisolone, methylprednisolone, beclamethasone, betamethasone, dexamethasone, fludrocortisone, hydrocortisone and triamcinolone. Systemic steroids work in the same way as natural cortisol, and are prescribed for a large number of serious diseases. Skin conditions treated with steroids include blistering diseases such as pemphigus and pemphigoid, and severe forms of dermatitis.

Accordingly, in some embodiments, the compounds as disclosed of BC11-15, BC11-19, BC11-28 and BC11-38, and derivatives and analogues thereof can be used in methods to maintain adrenal function for subjects undergoing long-term corticosteroid treatment. Long-term corticosteroid treatment can be administration of a corticosteroid to a subject for any time period longer than 1 week, or longer than 2 weeks, or longer than 3 weeks or more than three weeks.

Major contributors of chronic adrenal insufficiency in a subject are autoimmune adrenalitis, tuberculosis, AIDS and metastatic disease. Minor causes of chronic adrenal insufficiency are systemic amyloidosis, fungal infections, hemochromatosis and sarcoidosis. Autoimmune adrenalitis may be part of Type 2 autoimmune polyglandular syndrome, which can include type 1 diabetes), hyperthyroidism, autoimmune thyroid disease (also known as autoimmune thyroiditis, Hashimoto's thyroiditis and Hashimoto's disease). Hypogonadism and pernicious anemia may also present with this syndrome.

Adrenoleukodystrophy can also cause adrenal insufficiency. Adrenal Insufficiency can also be caused when a patient has a Craniopharyngioma which is a benign tumor that can damage the Pituitary gland causing the adrenal glands not to function (e.g., leading to secondary adrenal insufficiency syndrome).

In some embodiments, a subject amenable to treatment with a PDE11 inhibitor, such as any compound of formula (I)-(VI) as disclosed herein has hypoadrenia (adrenal fatigue), the precursor to adrenal insufficiency. Adrenal fatigue or hypoadrenia is a term used in alternative medicine to describe the belief that the adrenal glands are exhausted and unable to produce adequate quantities of hormones, primarily cortisol. The term "adrenal fatigue" may be applied to a collection of medically unexplained symptoms, but there is no scientific evidence supporting the concept of "adrenal fatigue" and it is not recognized as an actual diagnosis by the medical community. This is distinct from recognized forms of adrenal dysfunction such as adrenal insufficiency or Addison's Disease.

Hydrocortisone, the pharmaceutical term for cortisol, can be used in oral administration, intravenous injection or topical application. It is used as an immunosuppressive drug, given by injection in the treatment of severe allergic reactions such as anaphylaxis and angioedema, in place of prednisolone in patients who need steroid treatment but cannot take oral medication, and perioperatively in patients on long-term steroid treatment to prevent Addisonian crisis. It may be used topically for allergic rashes, eczema, psoriasis and certain other inflammatory skin conditions. It may also be injected into inflamed joints resulting from diseases such as gout. Accordingly, in some embodiments, a subject amenable to treatment with a PDE11 inhibitor, such as any compound of formula (I)-(VI) as disclosed herein are in need of hydrocortisone treatment, e.g., are in need of an immunosuppressive drug, or in need of treatment of a severe allergic reaction such as anaphylaxis and angioedema, or can be used in a methods to perioperatively treat subjects on long-term steroid treatment to prevent Addisonian crisis.

In alternative embodiments, a composition and methods of treatment with a PDE11 inhibitor, such as any compound of formula (I)-(VI) can be used for treating an autoimmune disease or allergic disease selected from any in the group comprising multiple sclerosis, type 1 diabetes, rheumatoid arthritis, asthma, chronic obstructive pulmonary diseases, inflammatory bowel disease, Alzheimer's disease and other neurodegenerative diseases with inflammatory components, atherosclerosis, vasculitis, and cancer, such as metastatic cancers. Other disorders or conditions to be treated include inflammatory diseases and conditions such as joint inflammation, rheumatoid arthritis, rheumatoid spondylitis, osteoarthritis, chronic glomerulonephritis, dermatitis, and inflammatory bowel disease, such as, for example, ulcerative colitis and/or Crohn's disease; respiratory diseases and conditions such as asthma, acute respiratory distress syndrome, chronic pulmonary inflammatory disease, bronchitis, chronic obstructive airway disease, and silicosis; infectious diseases and conditions such as sepsis, septic shock, endotoxic shock, gram negative, sepsis, toxic shock syndrome, fever and myalgias due to bacterial, viral or fungal infection, and influenza; Alzheimer's disease and other neurodegenerative diseases with an inflammatory component immune diseases and conditions such as autoimmune diabetes, systemic lupus erythematosis, graft vs. host reaction, allograft rejections, multiple sclerosis, psoriasis, and allergic rhinitis.

In some embodiments, a subject amenable to treatment with a PDE11 inhibitor, such as any compound of formula (I)-(VI) as disclosed herein are have an allergy, e.g., but not limited for the treatment of allergic rashes, eczema, psoriasis and certain other inflammatory skin conditions.

In some embodiments, a subject amenable to treatment with a PDE11 inhibitor, such as any compound of formula (I)-(VI) as disclosed has an inflammation associated disorder is an allergic condition or a chronic skin condition, for example, an allergic condition selected from the group consisting of: bronchial asthma, allergic rhinitis, drug-induced dermatitis, contact and atopic dermatitis. In some embodiments, the chronic skin condition is selected from the group consisting of: dermatitis herpeiformis, pemphigus, severe psoriasis, and seborrheic dermatitis. In some embodiments, a PDE11 inhibitor as disclosed herein can be used to treat an inflammatory condition or allergic condition which occurs in the uvea, iris, conjunctiva, or optic nerve.

In some embodiments, a PDE11 inhibitor as disclosed herein is useful in a method to reduce a symptoms of a respiratory disorder such as allergen-induced or inflammation-induced bronchial disorders such as bronchitis, obstructive bronchitis, spastic bronchitis, allergic bronchitis, allergic asthma, bronchial asthma, and chronic obstructive pulmonary disease (COPD) as well as inflammatory conditions of the gastrointestinal tract or bowel.

In some embodiments, a subject amenable to treatment with a PDE11 inhibitor, such as any compound of formula (I)-(VI) as disclosed has cancer, e.g., a blood cell cancer or a lymph gland cancers, for example, leukemia or lymphoma, or any cancer selected from prostate cancer, adenocortical cancers. In some embodiments, a subject amenable to treatment with a PDE11 inhibitor, such as any compound of formula (I)-(VI) can be a cancer selected from liver cancer (e.g. hepatocellular carcinoma (HCC), hepatoblastoma, cholangiocarcinoma (cancer of the bile duct), angiosarcoma), brain cancer, breast cancer, colon cancer, head and neck squamous cell carcinoma, lung cancer, pancreatic cancer, ovarian cancer, cervical cancer, melanoma and thyroid cancer; HIV; inflammation-related diseases such as hepatitis B virus (HBV), hepatitis C (HCV), cirrhosis and Alzheimer's disease; liver diseases such as HBV, HCV, cirrhosis, hepatic adenoma, hepatic angiosarcoma and hepatic angiosarcomas; emphysema; and hereditary hemochromatosis. In some embodiments, the subject has cervical cancer, colon cancers, melanomas and the like. Other cancers which can be treated include any cancer including but not limited to, oligodendroglioma, meningioma, GBM, breast cancer, colon cancer, Non-Hodgkin's small cell carcinoma (HNSCC), lung cancer (adrenocarcinomas), lung cancer (small cell carcinoma), pancreatic cancer, ovarian cancer, thyroid cancer and undifferentiated cancer.

In some embodiments, a PDE11 inhibitor as disclosed herein can be used to treat any cancer cell type. Cancers include, but are not limited to, bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In some embodiments, a PDE11 inhibitor as disclosed herein is useful in a method for treating, or reducing the spread of, or delaying or reducing the progression of or otherwise preventing, migration of metastatic cancer cells. Thus, a PDE11 inhibitor as disclosed herein are useful in modulating, e.g., reducing the migration of metastatic cancer cells. Compositions useful in methods of reducing the migration of metastatic cancer cells are delivered systematically by administering these compositions to a subject in need thereof. In some embodiments, a PDE11 inhibitor as disclosed herein for treatment to reduce, lymphocyte chemotaxis, lymphocyte adhesion to endothelial cells, and/or lymphocyte transendothelial migration in subject can be formulated, for example, for oral administration. Compositions comprising a PDE11 inhibitor as disclosed herein useful in methods of treating or alleviating a symptom of a metastatic cancer are administered, for example, as an adjunct therapy in addition to other known chemotherapy agents.

In some embodiments, a PDE11 inhibitor as disclosed herein can be used in a method of inhibiting migration of a metastatic cancer cell by contacting the metastatic cancer cell with a composition that preferentially inhibits PDE11.

The invention also provides methods of treating or delaying the progression of a metastatic cancer by administering to a subject in need thereof a composition comprising a PDE11 inhibitor as disclosed herein in an amount effective to reduce migration of metastatic cancer cells. For example, the metastatic cancer cell is derived from epithelial tissue. In some embodiments, such a method comprises a step of diagnosing and/or identifying a subject comprising a primary tumor selected from the group consisting of colorectal, stomach, pancreatic, biliary tree, small intestine, kidney, breast, prostate, ovarian, malignant melanoma, lung cancer, and lymphoma. These cells of these primary tumor types are characterized by metastatic migration mediated by chemokines such as CXCL12.

The subset of cancers known as "metastatic cancers" refer to those types of cancers in which the primary tumor is prone to spread from its original site to another part of the subject, a process known as metastasizing. In metastatic cancers, the primary tumor is often an epithelial-derived tumor. Epithelial derived tumor types that are prone to metastasizing include primary tumors originating in the colon and rectum, stomach, pancreas, biliary tree, small intestine, kidney, breast, prostate, ovaries, malignant melanoma, lung cancer, and lymphoma. The compositions and methods are useful in treating and/or preventing these metastatic cancers by inhibiting or otherwise reducing the migration of the metastatic cancer cells from the original site of the primary tumor to a second site within a subject.

Methods of identifying and/or diagnosing an individual who is suffering from or is at risk of developing a metastatic cancer are known in the art. For example, detection of a serum marker associated with metastatic cancer in an individual indicates that the individual is, has, or is at risk of developing metastases. CT scan or ultrasound is also used to confirm the presence of a tumor in any of the tissues and organs listed above. Diagnosis of any one of the above-listed primary tumors indicates that an individual is at risk of developing a metastasis. Multiple metastatic lesions are often the case, but single metastases may be seen. Optionally, biopsy is carried out to confirm metastatic cancer.

In some embodiments, a composition comprising a PDE11 inhibitor, such as a compound of any of formula (I)-(VI) as disclosed herein are useful in methods for treating, alleviating a symptom of, delaying the progression of or otherwise preventing a cancer that are induced by chronic inflammation. For example, a PDE11 inhibitor as disclosed herein is useful in a method to treat a carcinoma in a subject. A composition comprising a PDE11 inhibitor as disclosed herein is useful in the treatment of a cancer derived from epithelial tissues. For example, a composition comprising a PDE11 inhibitor as disclosed herein is useful in a method in the treatment of blood cancers (e.g., leukemia), lymphomas, and other cancers, such as adenocortical cancers, prostate cancer, colon cancer and/or liver cancer. Compositions comprising a PDE11 inhibitor as disclosed herein useful in methods of treating or alleviating a symptom of cancers induced by chronic inflammation are administered, for example, as an adjunct therapy in addition to other known chemotherapy agents.

In some embodiments, a subject amenable to treatment with a PDE11 inhibitor, such as any compound of formula (I)-(VI) as disclosed has idiopathic thrombocytopenia purpura, or auto immune hemolytic anemia, or thyroiditis or sarcoidosis.

In some embodiments, a subject amenable to treatment with a PDE11 inhibitor, such as any compound of formula (I)-(VI) as disclosed in need of cortisone hormone replacement, as disclosed herein.

Other Uses of the Methods and PDE11 Inhibitor Compounds

In some embodiments, a PDE11 inhibitor as disclosed herein can be used in methods for the treatment with overexpression or over activity of the PDE11 enzyme. In particular, an inhibitor of PDE11 can be used for the treatment of autoimmune diseases, or reduce or otherwise prevent multiple sclerosis and other autoimmune diseases associated with chemokine-induced migration of leukocytes. For example, a PDE11 inhibitor as disclosed herein can be used in an amount that is effective to treat, reduce, alleviate, delay the progression of or otherwise prevent an autoimmune disease or allergic disease selected from the group comprising multiple sclerosis, type 1 diabetes, rheumatoid arthritis, asthma, chronic obstructive pulmonary diseases, inflammatory bowel disease, Alzheimer's disease and other neurodegenerative diseases with inflammatory components, atherosclerosis, vasculitis, and cancer, including metastatic cancer.

In some embodiments, a composition comprising PDE11 inhibitor as disclosed herein and/or salts thereof can be used in a method for increasing cortisol production in a subject, for example or in methods for preventing the development of disease or disorder associated with adrenal insufficiency as disclosed herein.

In some embodiments, a PDE11 inhibitor as disclosed herein and/or salts thereof can be used in a method for treating adrenal dysfunction or arrest, where low cortisol levels are a complication or side effect of where the subject has been exposed to any one of the following: radiation (e.g., accidental radiation exposure), radiation therapy, chemotherapy, and radiation as a pretreatment to ablate an adrenal cancer, or a disease or disorder associated with the hypothalamus and/or pituitary gland etc.

In addition to the diagnostic tests described above, clinical features of adrenal insufficiency and associated diseases and/or disorders can be monitored for assessment of low cortisol and/or PDE11 activity following onset of adrenal insufficiency or an associated disease or disorder. These features include, but are not limited to: assessment of the presence of adrenal cell damage, assessment of insulin tolerance, stress levels, and behavioral abnormalities. Such assessment can be done with methods known to one of ordinary skill in the art, such as behavioral testing, blood testing, and imaging studies, such as radiologic studies, CT scans, PET scans, etc.

In some embodiments, a composition and methods as disclosed herein using a PDE11 inhibitor can be used in method to increase or improve well-being in a subject with adrenal insufficiency. In some embodiments, the methods as disclosed herein can be used to treat a subject with a symptom of stress, depression, or lack of well-being.

In alternative embodiments, the compositions and methods as disclosed using a PDE11 inhibitor as disclosed herein can be used in a method for performance enhancement, for example, in to increase performance in stressful conditions (both physiological and psychological stressful situation), and increase stamina and/or muscle strength or muscle size in subjects.

In such embodiments and other aspects as disclosed herein, the composition of the present invention may be manufactured into liquids, pastes, bars, cakes, powders, granulates, effervescent tablets, tablets, capsules, lozenges, chewing gum, fast melting tablets or wafers, sublingual tablets, a spray or the like, using conventional methods practiced in the food, sweets and pharmaceutical industry. Alternatively, the composition may also be manufactured in the form of or as a part of a food product, such as a liquid, a paste a bar, a cake a powder or a granulate. It may for example be in the form of a fermented food product, a functional food product, or a sport drink or the like as mentioned above. For example an energy bar according to the present invention may include, in addition to a PDE11 inhibitor as disclosed herein, can also a variety of other components such as, for example, nuts, crisps, fruit pieces, chocolate, seeds, and the like. Preferred nuts are almonds, peanuts, hazelnuts, cashews, walnuts, pecans, brazil nuts, and the like. Crisp components include rice crisps, corn crisps, oats, wheat flakes, and the like. The chocolate can be any type of chocolate or chocolate like edible component in various forms, such as, for example, chocolate chips, chunks, flakes and the like. Non-limiting examples of seeds include sesame, sun flower, poppy, caraway, fennel and the like. Additionally, traditional food ingredients such as flavors and the like may be included. For example, additional ingredients may include natural and artificial flavors, sweeteners, salt, flavor enhancers, color additives, emulsifiers, stabilizers, fats, preservatives, and the like.

In some embodiments, a PDE11 inhibitor as disclosed herein can be included into animal feeds for mammals. A PDE11 inhibitor can be included in said animal feeds the same way it is included in the aforesaid foods and beverages. The animal feeds are not limited to uses for any particular animals. For instance, the animal feeds may be formulated to feed farm animals like cattle and pigs, and companion animals like dogs, cats, and hamsters. The animal feeds may include flour and meat as ingredients. Said flour may be comprised of wheat powder, rice powder, rye powder, oat powder, barley powder, grain powder, corn powder, and soy powder; said flour may also be comprised of two or more of the aforesaid powder. The use of said flour may provide the necessary carbohydrates for the companion animals. Among the aforesaid powder, the wheat powder is preferably used. The wheat powder may be used alone or used with high-grade flour, middle-grade flour, and low-grade flour; the wheat powder may also be used with any other types of flour. The elasticity of the heat-processed animal feeds may be adjusted by combining the wheat powder with wheat grain and soy proteins. After the heat treatment, the lattice-like structures in wheat bran will become enlarged, which helps improve its taste.

In alternative embodiments, a composition comprising a PDE11/PDE dual inhibitor function, e.g., such a compound of formula (V) or (VI) which inhibits both PDE11 and PDE10 can be used in a method for treatment of subjects who have an increased PDE11 activity, and/or in diseases and disorders where it is desirable to inhibit both PDE11 and PDE10 simultaneously.

Examples of diagnostic tests to determine PDE11 activity in a subject are set forth below. A first determination of PDE11 activity, level of cAMP, in a cell and/or tissue, and/or cortisol levels in the serum can be determined by using one of the methods described herein (or other methods known in the art), and a second, subsequent determination of the level of PDE activity or level of cAMP. A comparison of the PDE11 activity and/or cAMP level and/or the level of serum cortisol can be determined in a subject at different time points (e.g., prior to treatment and during or after administration or treatment with a PDE11 inhibitor) may be used to assess the effectiveness of administration of a pharmaceutical compound of the invention as a prophylactic or an active treatment of the PDE11-associated disease or disorder, such as low cortisol levels and/or adrenal insufficiency or an associated disease or disorder. Family history or prior occurrence of a PDE11-associated disease or disorder, e.g., a family history of low cortisol or adrenal insufficiency, even if the subject is not current experiencing symptoms of adrenal insufficiency or an associated disease or disorder, such subject may be selected for prophylactic intervention by administering a PDE11 inhibitor, such as any compound of formula (I)-(VI) as described herein to reduce or prevent increased PDE11 activity and/or abnormal levels of cAMP and/or low cortisol levels.

In some embodiments, one or ordinary skill in the art can readily diagnose abnormal PDE11 activity and/or abnormal levels of cAMP or low cortisol levels in a subject using standard methods such as, but not limited to: imaging methods, electrophysiological methods, blood tests, and histological methods. Additional methods of diagnosis and assessment of low cortisol levels, and/or adrenal insufficiency or a PDE11-associated disease or disorders are known to those of skill in the art.

Kits

The invention also provides kits or pharmaceutical packages that include a PDE11 inhibitor, such as any compound of formula (I)-(VI) for use in the prevention and treatment of the diseases and conditions described herein. In some embodiments, a PDE11 inhibitor can be in the form of, for example, tablets, capsules, or lyophilized powders. In some embodiments, the kits or packages can optionally include instructions for using the PDE11 inhibitor in the prevention and/or treatment of low cortisol levels, and/or adrenal insufficiency or an adrenal-insufficiency associated diseases or disorder. In some embodiments, a PDE11 inhibitor can be provided in the kits or packages in a bottle or another appropriate form (e.g., a blister pack). Optionally, the kits or pharmaceutical packages can also include other pharmaceutically active agents (see, e.g., the agents listed above, such as anti-obesity agents), and/or materials used in administration of the drug(s), such as diluents, needles, syringes, applicators, and the like.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

Some Embodiments of the Present Invention can be Defined as any of the Following Numbered Paragraphs.

1. A compound for inhibiting PDE11, wherein the compound is of formula (I):

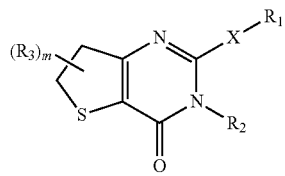

I wherein

X is O, NR$_4$, S or absent;

R$_1$, and R$_2$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^B$; —CO$_2$R$^B$; -; —CN; —SCN; —SR$^B$; —SOR$^B$; —SO$_2$R$^B$; —NO$_2$; —N(R$^B$)$_2$; —NHC(O)R$^B$; or C(R$^B$)$_3$; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

each R$_3$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)R$^B$; —CO$_2$R$^B$; -; —CN; —SCN; —SR$^B$; —SOR$^B$; —SO$_2$R$^B$; —NO$_2$; —N(R$^B$)$_2$; —NHC(O)R$^B$; or C(R$^B$)$_3$; wherein each occurrence of R$^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

R$_4$ is hydrogen or C$_{1-4}$ alkyl;

m is an integer 0 to 2, inclusive.

2. The compound of paragraph 1, wherein

R$_1$ is optionally substituted C$_{1-6}$ alkyl, optionally substituted aryl, or optionally substituted heteroaryl;

R$_2$ is optionally substituted aryl, or optionally substituted heteroaryl;

3. The compound of paragraph 1, wherein X is S.

4. The compound of paragraph 1, wherein m is 0.

5. The compound of paragraph 1, wherein the compound is selected from the group consisting of:

-continued

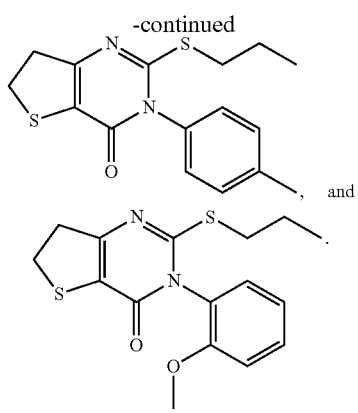

, and

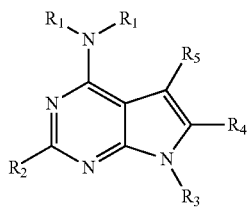

6. A compound for inhibiting PDE11, wherein the compound is of formula (II):

$$\text{II}$$

wherein
each $R_1$, and $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; or substituted or unsubstituted, branched or unbranched alkylaryl;

$R_2$, $R_4$ and $R_5$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo.

7. The compound of paragraph 6, wherein
each $R_1$ is independently hydrogen; halogen; cyclic or acyclic, substituted or unsubstituted, branched or unbranched aliphatic; substituted or unsubstituted, branched or unbranched aryl; substituted or unsubstituted, branched or unbranched heteroaryl; or substituted or unsubstituted, branched or unbranched alkylaryl.

8. The compound of paragraph 6, wherein
$R_3$ is substituted or unsubstituted, branched or unbranched aryl; substituted or unsubstituted, branched or unbranched heteroaryl; or substituted or unsubstituted, branched or unbranched alkylaryl;

9. The compound of paragraph 6, wherein
$R_5$ is substituted or unsubstituted, branched or unbranched aryl; substituted or unsubstituted, branched or unbranched heteroaryl; or substituted or unsubstituted, branched or unbranched alkylaryl.

10. The compound of paragraph 6, wherein
$R_2$ is hydrogen.

11. The compound of paragraph 6, wherein the compound is selected from the group consisting of:

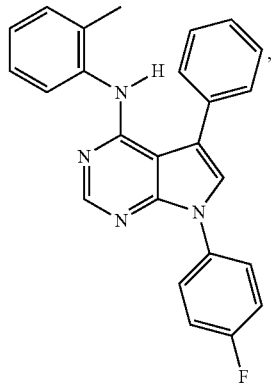 [SMILES: Fc1ccc(-n2cc(-c3ccccc3)c3c(Nc4ccccc4)ncnc32)cc1]

,

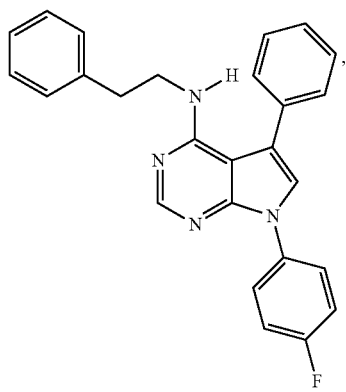

,

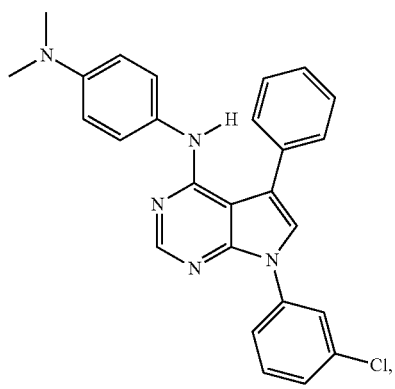

,

-continued

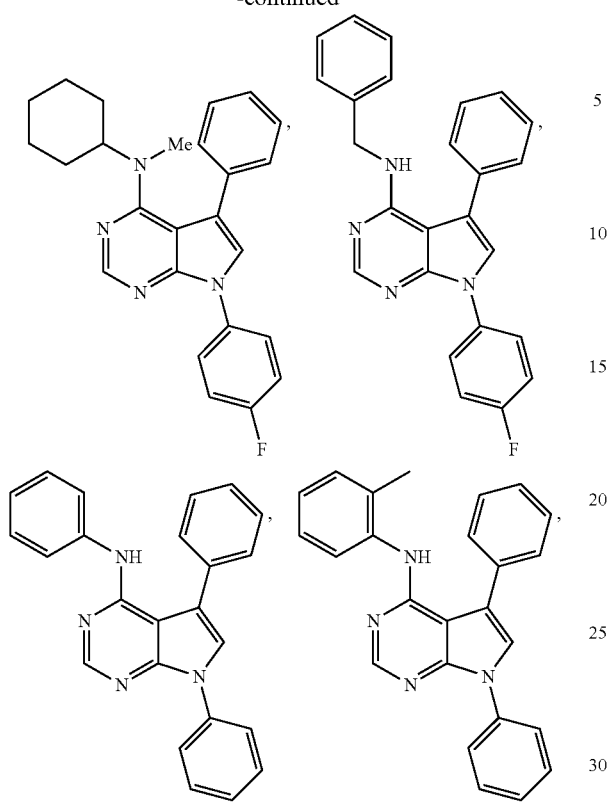

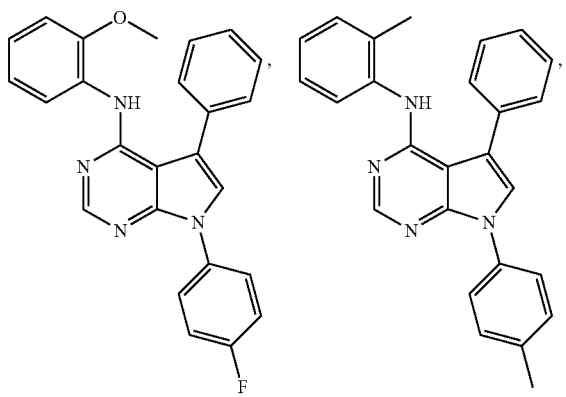

-continued

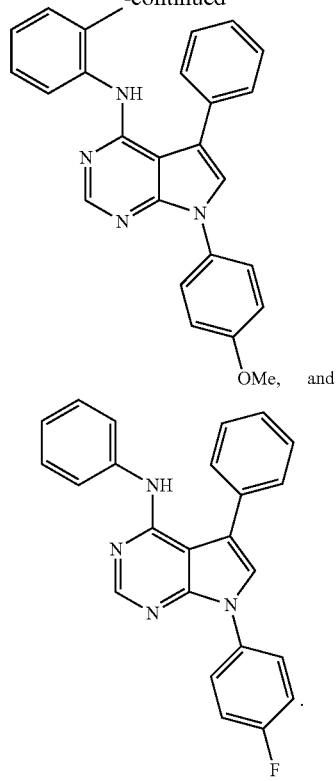

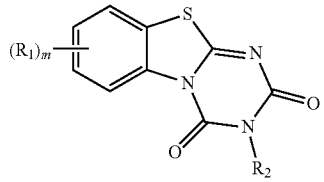

12. A compound for inhibiting PDE11, wherein the compound is of formula (III):

$$\text{III}$$

wherein
each $R_1$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —S$R^B$; —SO$R^B$; —SO$_2R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

$R_2$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; or substituted or unsubstituted, branched or unbranched alkylaryl;

m is an integer 0 to 4, inclusive.

13. A compound of paragraph 12, wherein each $R_1$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; —C(=O)$R^B$; —CO$_2R^B$; -; —CN; —SCN; —SR$^B$; —SOR$^B$; —SO$_2R^B$, —NO$_2$; —N($R^B$)$_2$, —NHC(O)$R^B$; or C($R^B$)$_3$; wherein each occurrence of $R^B$ is independently hydrogen; halogen; aliphatic; heteroaliphatic; acyl; hydroxyl; aloxy; amino; alkylamino; dialkylamino; or alkylhalo.

14. A compound of paragraph 12, wherein $R_2$ is substituted or unsubstituted, branched or unbranched aryl; substituted or unsubstituted, branched or unbranched heteroaryl; or substituted or unsubstituted, branched or unbranched alkylaryl;

15. A compound of paragraph 12, wherein m is 0 or 1.

16. A compound of paragraph 12, wherein the compound is selected from the group consisting of:

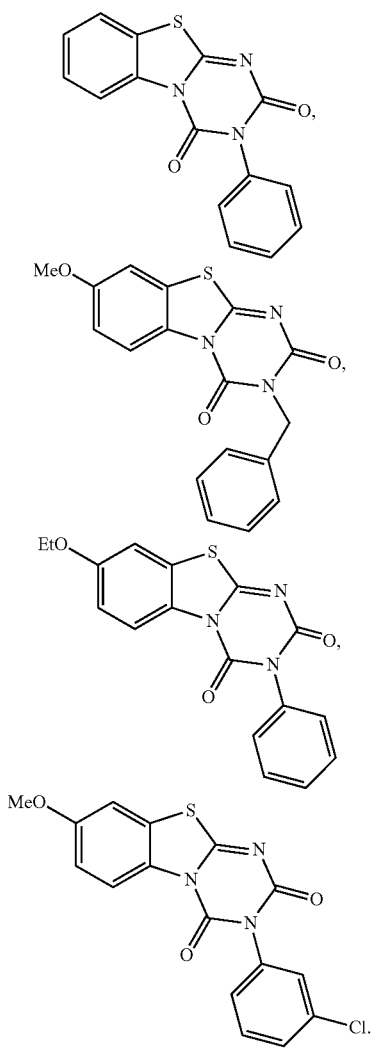

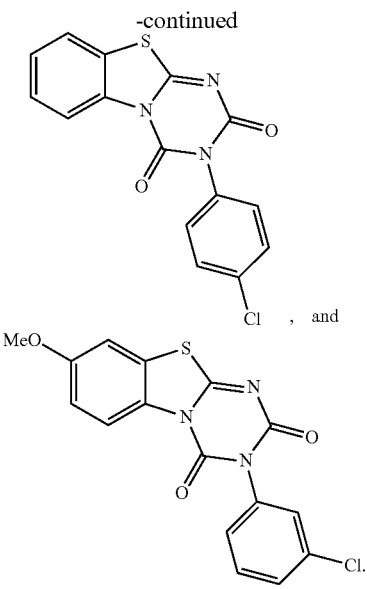

17. A compound for inhibiting PDE11, wherein the compound is of formula (IV):

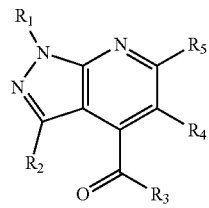

IV wherein $R_1$ and $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; or substituted or unsubstituted, branched or unbranched alkylaryl;

$R_2$, $R_4$, and $R_5$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2R^B$; -; —CN; —SCN; —SR$^B$; —SOR$^B$; —SO$_2R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo.

18. The compound of paragraph 17, wherein $R_1$ is hydrogen; substituted or unsubstituted, branched or unbranched aryl; substituted or unsubstituted, branched or unbranched heteroaryl; or substituted or unsubstituted, branched or unbranched alkylaryl.

19. The compound of paragraph 17, wherein
   $R_1$ is substituted or unsubstituted, branched or unbranched alkylnitrile.
20. The compound of paragraph 17, wherein
   $R_2$ is hydrogen; cyclic or acyclic, substituted or unsubstituted, branched or unbranched aliphatic; cyclic or acyclic, substituted or unsubstituted, branched or unbranched heteroaliphatic.
21. The compound of paragraph 17, wherein
   $R_3$ is cyclic or acyclic, substituted or unsubstituted, branched or unbranched aliphatic; cyclic or acyclic, substituted or unsubstituted, branched or unbranched heteroaliphatic.
22. The compound of paragraph 17, wherein
   $R_3$ alkylamino or dialkylamino.
23. The compound of paragraph 17, wherein
   $R_4$ is hydrogen.
24. The compound of paragraph 17, wherein
   $R_5$ substituted or unsubstituted, branched or unbranched aryl; substituted or unsubstituted, branched or unbranched heteroaryl; or substituted or unsubstituted, branched or unbranched alkylaryl.
25. The compound of paragraph 17, wherein the compound is selected from the group consisting of:

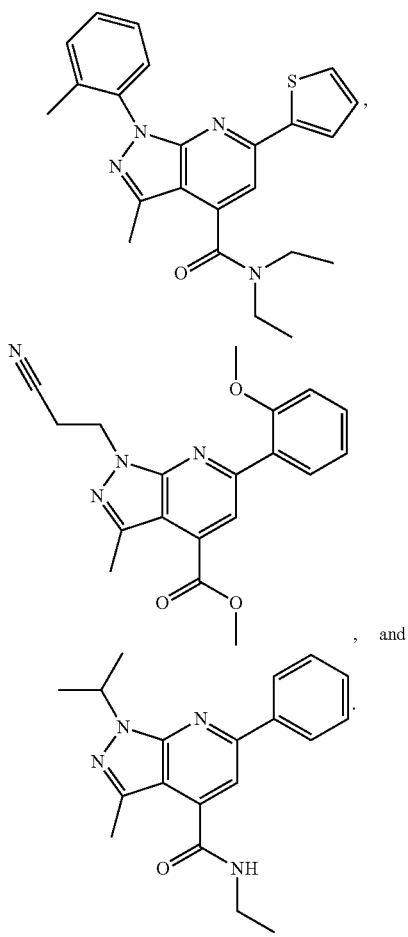

, and

26. A compound for inhibiting PDE11, wherein the compound is of formula (V):

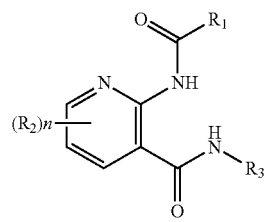

wherein $R_1$, and $R_3$ are independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-C(=O)R^B$; $-CO_2R^B$; $-N(R^B)_2$; $-NHC(O)R^B$; or $C(R^B)_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

each $R_2$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; $-C(=O)R^B$; $-CO_2R^B$; -; $-CN$; $-SCN$; $-SR^B$; $-SOR^B$; $-SO_2R^B$; $-NO_2$; $-N(R^B)_2$; $-NHC(O)R^B$; or $C(R^B)_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;

n is an integer 0 to 4, inclusive.

27. The compound of paragraph 26, wherein $R_1$ is optionally substituted aryl, or optionally substituted heteroaryl.
28. The compound of paragraph 26, wherein $R_3$ is optionally substituted aryl, or optionally substituted heteroaryl.
29. The compound of paragraph 26, wherein $R_1$ is optionally substituted aryl, or optionally substituted heteroaryl, and $R_3$ is optionally substituted aryl, or optionally substituted heteroaryl;
30. The compound of paragraph 26, wherein
   $R_3$ is

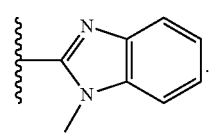

31. The compound of paragraph 26, wherein $R^1$ is optionally substituted phenyl.

32. The compound of paragraph 26, wherein n is 0.

33. The compound of paragraph 26, wherein formula (V) has the following structure:

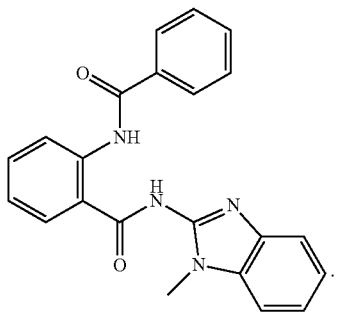 [SMILES: Cn1c(NC(=O)c2ccccc2NC(=O)c2ccccc2)nc2ccccc21]

34. A compound for inhibiting PDE11, wherein the compound is of formula (VI):

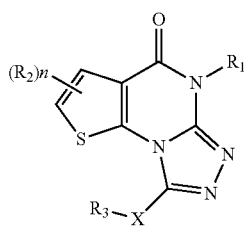

wherein
  X is O, $NR_4$, S or absent;
  $R_1$, $R_3$ and $R_4$ are independently, hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;
  each $R_2$ is independently halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —C(=O)$R^B$; —CO$_2$$R^B$; -; —CN; —SCN; —S$R^B$; —SO$R^B$; —SO$_2$$R^B$; —NO$_2$; —N($R^B$)$_2$; —NHC(O)$R^B$; or C($R^B$)$_3$; wherein each occurrence of $R^B$ is independently hydrogen; halogen; a protecting group; aliphatic; heteroaliphatic; acyl; aryl moiety; heteroaryl; hydroxyl; aloxy; aryloxy; alkylthioxy; arylthioxy; amino; alkylamino; dialkylamino; heteroaryloxy; heteroarylthioxy; or alkylhalo;
  n is an integer 0-2, inclusive.

35. The compound of paragraph 34, wherein X is S.

36. The compound of paragraph 34, wherein $R_1$ is optionally substituted aryl, or optionally substituted heteroaryl.

37. The compound of paragraph 34, wherein $R_3$ is substituted or unsubstituted, branched or unbranched alkene.

38. The compound of paragraph 34, wherein $R_1$ is optionally substituted aryl, or optionally substituted heteroaryl; and $R_3$ is substituted or unsubstituted, branched or unbranched alkenyl;

39. The compound of paragraph 34, wherein $R_3$ is $C_2$-$C_4$ alkenyl.

40. The compound of paragraph 34, wherein $R_1$ is optionally substituted phenyl.

41. The compound of paragraph 34, wherein $R_2$ is $R_3$ is substituted or unsubstituted, branched or unbranched alkanyl;

42. The compound of paragraph 34, wherein $R_2$ is $C_1$-$C_4$ alkanyl.

43. The compound of paragraph 34, wherein n is 2.

44. The compound of paragraph 34, wherein formula VI is

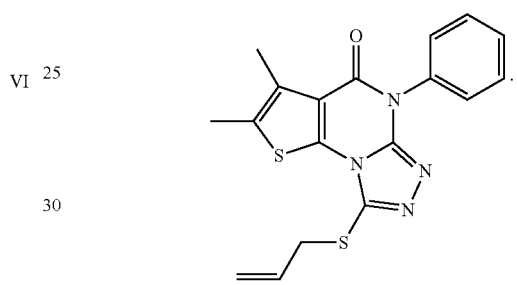

45. A method for treating a subject with low cortisol levels, or adrenal insufficiency, or an adrenal insufficiency associated disorder, the method comprising administering a therapeutically effective amount of a composition comprising at least one compound of any of formula (I), (II), (III) (IV), (V) or (VI) to the subject.

46. The method of paragraph 45, wherein the subject is identified as having adrenal insufficiency prior to administering the composition comprising a compound of any of formula (I), (II), (III) (IV), (V) or (VI) to the subject.

47. The method of paragraphs 45 or 46, wherein the subject is a human subject.

48. The method of any of paragraphs 46 to 47, wherein the subject has any one of the following: a plasma cortisol level of less than about 140 nmol/L at between 8:00-10:00 am in the morning, a plasma cortisol level of less than about 80 nmol/L at about midnight, a urine cortisol level of less than about 28 nmol/24 hrs.

49. The method of any of paragraphs 46 to 48, wherein the subject is a low cortisol levels, or adrenal insufficiency.

50. The method of any of paragraphs 46 to 49, wherein the subject is a disease or disorder associated with adrenal insufficiency.

51. The method of paragraph 50, wherein a disease or disorder associated with adrenal insufficiency is Addison's disease, autoimmune adrenalitis, congenital adrenal hyperplasia, adrenoma of the adrenal gland, impairment of the pituitary gland, impairment of the hypothalamus, hypoadrenia, allergic reaction, autoimmune disease.

52. The method of paragraph 46 to 51, wherein the composition comprises a pharmaceutically acceptable carrier.

53. The method of any of paragraphs 46 to 53, wherein the subject is a human subject.

54. A method for treating a subject with inflammatory condition or an inflammation associated disorder, the method comprising administering a therapeutically effective amount of a composition comprising at least one compound of any of formula (I), (II), (III) (IV), (V) or (VI) to the subject.

55. The method of paragraph 54, wherein the inflammatory condition is selected from the group consisting of: rheumatoid arthritis, systemic lupus, acute gouty arthritis, psoriatic arthritis, ulcerative colits and Crohn's disease.

56. The method of paragraph 54, wherein the inflammation associated disorder is an allergic condition or a chronic skin condition.

57. The method of paragraph 56, wherein the allergic condition is selected from the group consisting of: bronchial asthma, allergic rhinitis, drug-induced dermatitis, contact and atopic dermatitis.

58. The method of paragraph 56, wherein the chronic skin condition is selected from the group consisting of: dermatitis herpeiformis, pemphigus, severe psoriasis, and seborrheic dermatitis.

59. The method of paragraph 54 to 57, wherein the inflammatory condition or allergic condition is an inflammatory condition or allergic condition of any one of the uvea, iris, conjunctiva, or optic nerve.

60. The method of any of paragraphs 54 to 59, wherein the subject is a human subject.

61. A method for treating a subject with in need of hydrocortisone treatment, the method comprising administering a therapeutically effective amount of a composition comprising at least one compound of any of formula (I), (II), (III) (IV), (V) or (VI) to the subject.

62. The method of paragraph 61, wherein the subject has cancer.

63. The method of paragraph 62, wherein the cancer is a blood cell cancer or a lymph gland cancers.

64. The method of paragraph 63, wherein the blood cancer is leukemia.

65. The method of paragraph 63, wherein the lymph gland cancer is lymphoma.

66. The method of paragraph 61, wherein the cancer is selected from any one of the following cancer: blood cell cancers, lymph gland cancers, prostate cancer, adenocortical cancers.

67. The method of paragraph 61, wherein the subject has idiopathic thrombocytopenia purpura.

68. The method of paragraph 61, wherein the subject has auto immune hemolytic anemia.

69. The method of paragraph 61, wherein the subject has thyroiditis or sarcoidosis.

70. The method of paragraph 61, wherein the subject is in need of cortisone hormone replacement therapy.

71. The method of any of paragraphs 61 to 70, wherein the subject is a human subject.

72. A method for treating a subject with cancer, the method comprising administering a therapeutically effective amount of a composition comprising at least one compound of any of formula (I), (II), (III) (IV), (V) or (VI) to the subject.

73. The method of paragraph 72, wherein the cancer is a blood cell cancer or a lymph gland cancers.

74. The method of paragraph 73, wherein the blood cancer is leukemia.

75. The method of paragraph 73, wherein the lymph gland cancer is lymphoma.

76. The method of paragraph 72, wherein the cancer is selected from any one of the following cancer: blood cell cancer, lymph gland cancer, prostate cancer, adenocortical cancers.

77. The method of paragraph 72, wherein the cancer is resistant to chemotherapy.

78. The method of paragraph 72, wherein the subject is administered an additional therapeutic agent for the treatment of cancer.

79. The method of paragraph 78, wherein the additional therapeutic agent is radiotherapy or chemotherapy.

80. The method of any of paragraphs 72 to 79, wherein the subject is a human subject.

81. A method for increasing cortisol production in the adrenal glands, the method comprising contacting adenocortical cells of the adrenal gland with a composition comprising at least one compound of any of formula (I) to (VI).

82. The method of paragraph 81, wherein the adrenocortical cells are present within a subject.

83. The method of paragraph 81, wherein the adrenocortical cells are contacted ex vivo and implanted into a subject.

84. The method of any of paragraphs 81 to 83, wherein the subject is a human subject.

85. The method of any of paragraphs 81 to 84, wherein the subject is low cortisol levels, or adrenal insufficiency or a disease or disorder associated with adrenal insufficiency.

86. The method of paragraph 85, wherein a disease or disorder associated with adrenal insufficiency is selected from the group comprising inflammation, Addition's disease, Nelson's disease, autoimmune adrenalitis, congenital hyperplasia, adrenoma of the adrenal gland, impairment of the pituitary gland, impairment of the hypothalamus, hypoadrenia, autoimmune disease, or cancer.

87. A kit comprising a composition one or more compounds compound of formula (I), (II), (III) (IV), (V) or (VI), and instructions for administration to a subject.

88. A pharmaceutical composition comprising at least one compound of formula (I) and a pharmaceutically acceptable carrier.

89. A pharmaceutical composition comprising at least one compound of formula (II) and a pharmaceutically acceptable carrier.

90. A pharmaceutical composition comprising at least one compound of formula (III) and a pharmaceutically acceptable carrier.

91. A pharmaceutical composition comprising at least one compound of formula (IV) and a pharmaceutically acceptable carrier.

92. A pharmaceutical composition comprising at least one compound of formula (V) and a pharmaceutically acceptable carrier.

93. A pharmaceutical composition comprising at least one compound of formula (VI) and a pharmaceutically acceptable carrier.

94. The pharmaceutical composition of paragraphs 88-93 in a method to increase cortisol levels in a subject.

95. Use of the compound of formula (I), (II), (III) (IV), (V) or (VI) for preparation of a medicament for increasing cortisol levels in a subject.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The invention can be understood more fully by reference to the following detailed description and illustrative examples, that are intended to exemplify non-limiting embodiments of the invention.

EXAMPLES

The following examples are provided for illustrative purposes only and are not intended to limit the scope of the invention. The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

Materials and Methods

Yeast Strains, Media, and Growth Conditions.

Constructions of *S. pombe* strains that express mammalian PDEs were previously described (26). Yeast cells were grown and maintained using YEA-rich and EMM-defined media as described by Demirbas, et al. (26).

5FOA Growth Assays, HTS and Statistical Analysis.

5FOA growth assays were performed using strains that express human PDE1B 1, PDE3A1, PDE4A1, PDE7A1, PDE9A5, PDE10A1, and PDE11A4, murine PDE2A2 and PDE8A1, and bovine PDE5A1, as described (26).

High-Throughput Screening (HTS) was performed at the ICCB-Longwood Screening Facility of Harvard Medical School. Yeast cells that express human PDE11A4 were grown in EMM medium with 0.25 mMcAMP for 24 hours to $10^7$ cells/ml. The screening 5FOA medium is SC-based and contains 0.4 g/L 5FOA. 25 it 5FOA medium was transferred into duplicate 384-well flat, clear-bottom microtiter dishes and 100 nl of compounds (from stock solutions of generally 10-15 mM) were pinned into the wells. Cells were collected by centrifugation, resuspended in 5FOA medium with 120 µM cGMP, and 25 µl was transferred into each well at an initial cell density of $0.75 \times 10^5$ cells/ml. Control plates consisted of positive control cultures containing 25 µM and 40 µM BC76 and negative control cultures containing 0.2% DMSO. Each screening plate included internal positive and negative control wells. Plates were incubated at 30° C. for 48 h in a closed container with moist paper towels to prevent evaporation. ODs of the cultures were measured at 600 nm, using a Wallac EnVision Plate Reader. In cherry-picking experiments, 100 nl compounds were added to each well using pocket tips instead of steel pin arrays.

Z'-factors of assays were determined as described (23). An assay with a Z'-factor >0.5 is considered sufficiently robust for HTS. Within a screen, individual wells are assigned a Z score, representing the number of standard deviations above or below the mean of the negative control wells. Duplicate Z scores for each compound are plotted onto a grid and projected perpendicularly to the diagonal. A Composite Z score is the distance from this point on the diagonal to the origin.

In Vitro Enzyme Assays.

In vitro enzyme assays were conducted via the $Ba(OH)_2$ precipitation method of Wang et al. (32) using recombinant human PDE11A4, PDE10A1, PDE5A1, PDE6C, PDE8A (BPS Bioscience Inc.), PDE7A (BIOMOL International), and PDE4A10 enzymes (gift from HengmingKe), in the presence of 100 nM cGMP, 30 nM cAMP, 500 nM cGMP, 1.7 µM cGMP, 10 nM cAMP, 15 nM cAMP, and 625 nM cAMP, respectively. Inhibitor concentrations that reduce enzyme activity by 50% ($IC_{50}$) are presented. The values are means of at least three independent experiments.

Mammalian Cell Culture, cAMP Assays and Immunoblot Analysis.

Human NCI-H295R cells were maintained as described (33). HeLa cells were maintained in DMEM with 10% FBS. 90% confluent cells in 12-well dishes were incubated in serum-starved media for 1 h, then in 0.5 ml serum-starved media with 20 □M compounds or 0.2% DMSO for 2 h in the absence or presence of 10 µM forskolin (Sigma Aldrich). Media was collected and cAMP levels were measured as described (33), using a cAMP ELISA kit (Enzo). cAMP levels were normalized to protein content measured using a BCA Protein Assay Kit (Pierce). Immunoblot analysis of protein lysates was performed as described (34), using phospho-CREB(9198), Akt(4685), or CREB(9197) primary antibodies (Cell Signaling Technology) and goat anti-rabbit IgG-HRP secondary antibody (sc-2030, Santa Cruz).

Cortisol Assays.

H295R cells were treated with compounds as described in the cAMP assays, for 24 h. Media was collected and cortisol content was quantified using a Cortisol EIA Kit (Oxford Biomedical Research). Cortisol levels were normalized to protein concentrations in cell extracts, as described above.

Quantitative RT-PCR:

Total cellular RNA was isolated using RNeasy mini kits (QIAGEN). cDNA was synthesized from 2 µg of total RNA using SuperScript II reverse transcriptase with random hexamers. PDE11A expression was determined by a SyBr green Real Time PCR assay (ABI) using PDE11A-specific primers (TGGAGTGGATTGATAGCATCTG (SEQ ID NO: 1) and TTTGGTGTAGCTCTTCCCAC (SEQ ID NO: 2). Expression levels were normalized using RPLP0 expression (IDT).

Example 1

The second messengers cyclic AMP (cAMP) and cyclic GMP (cGMP) regulate a myriad of processes such as cell proliferation, differentiation, apoptosis, inflammation, hormone secretion, muscle contraction, and cognitive functions (1, 2). Intracellular cAMP and cGMP levels are determined by the balance between their synthesis by adenylate or guanylate cyclases and their degradation by phosphodiesterases (PDEs). In mammals, 21 genes encode >100 PDE isoforms that are grouped into 11 families based on their substrate-specificity, overall sequence conservation, and regulatory properties. The unique tissue-expression and subcellular-localization patterns of PDE enzymes, together with their diversity and differences in enzymatic properties, allow individual isoforms to control specific physiological functions and link them to different pathological conditions. Therefore, selective PDE inhibitors have the potential to provide therapeutic benefit to a wide range of diseases (1, 2)

PDE11 is the most recently discovered phosphodiesterase family (3). In humans, the PDE11A gene encodes four isoforms that are dual-specificity enzymes, hydrolyzing both cAMP and cGMP (3-5). PDE11A is expressed in skeletal muscle, prostate, testis, brain, kidney, liver, pancreas, pituitary and adrenal glands (6-9), but the biological roles of PDE11 in these tissues are poorly understood due to the lack of selective inhibitors. PDE11A knock-out mice display subtle alterations in sperm function (10) and psychiatric disease-related phenotypes (11). The absence of more dramatic phenotypes may be due to compensation by other PDEs during development that masks normal roles for PDE11.

Genetic defects of PDE11A have been linked to major depression, bipolar disorder, asthma, adrenal, testicular and prostatic cancers in genome-wide association studies (12-17). In addition, inactivating mutations of PDE11A are found in patients with several forms of adrenal hyperplasia and Cushing syndrome, which results from excess cortisol release from adrenocortical tumors (17-21). Adrenal tumor homogenates from these patients have elevated cyclic nucleotide levels and increased CREB phosphorylation, suggesting that PDE11 plays a major role in controlling cAMP and cGMP levels in these tissues (18). In addition, the PDE5 inhibitor Tadalafil, currently used to treat erectile dysfunction, has significant activity against PDE11 (22). Thus, PDE11-specific inhibitors would be useful for studying the biological roles of PDE11 and in clarifying any PDE11-related side effects of this commonly prescribed drug.

The inventors previously reported the development of a fission yeast cell-based screening platform to identify small-molecule inhibitors of mammalian PDEs. (23-26). The screen employs genetically engineered yeast strains whose growth behavior reflects the activity of heterologously-expressed PDEs. The cells express aura4 reporter that is regulated by PDE activity and is counterselectable for growth in medium containing 5-fluoroorotic acid (5FOA). Cells lacking both adenylate cyclase and PDE activity respond to low levels of exogenous cAMP or cGMP to activate PKA and thus repress ura4 expression, conferring 5FOA-resistance (5FOAR). Cells that express PDEs that hydrolyze the exogenously added cGMP (or cAMP) remain 5FOA-sensitive (5FOAS; FIG. 1A-top panel) while the addition of a PDE inhibitor confers 5FOAR growth (FIG. 1A-bottom panel).

Using strains that express 10 of the 11 PDE families, this yeast-based assay allowed the inventors to identify and profile PDE inhibitors. The inventors have previously used this platform to identify PDE4 and PDE7 inhibitors that are biologically active in mammalian cells. (24).

Herein, the inventors demonstrate the use of this screening platform to develop and perform a high-throughput-screen (HTS) for PDE11 inhibitors. The inventors discovered four highly selective and potent compounds, as judged by in vitro enzyme assays and yeast-based growth assays. These are the first PDE11-selective inhibitors to be reported. The inventors further used these compounds to demonstrate a biological role of PDE11 in cortisol production in H295R adrenocortical carcinoma cells. One of these compounds, BC11-38, increases cAMP levels, CREB phosphorylation, and cortisol production in these cells. By comparing the effects of BC11-38 and structural analogs on H295R cells versus HeLa cells, which have little or no PDE11A expression, the inventors demonstrate that the biological effects of these compounds are due to PDE11 inhibition.

Optimization and Performance of a Yeast-Based HTS for PDE11 Inhibitors.

Figure 1B:
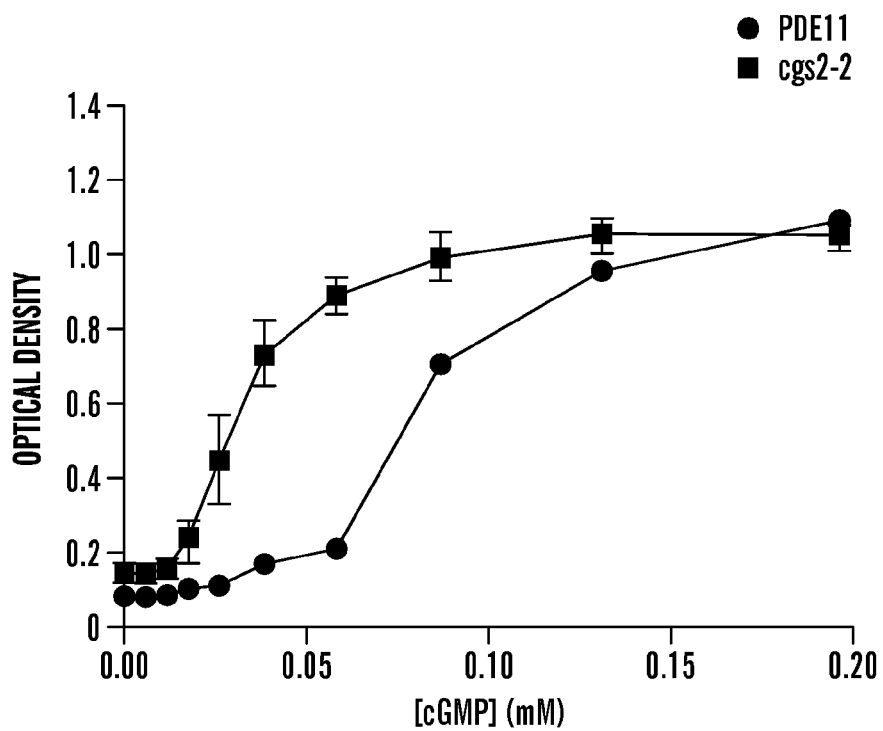
Figure 6:
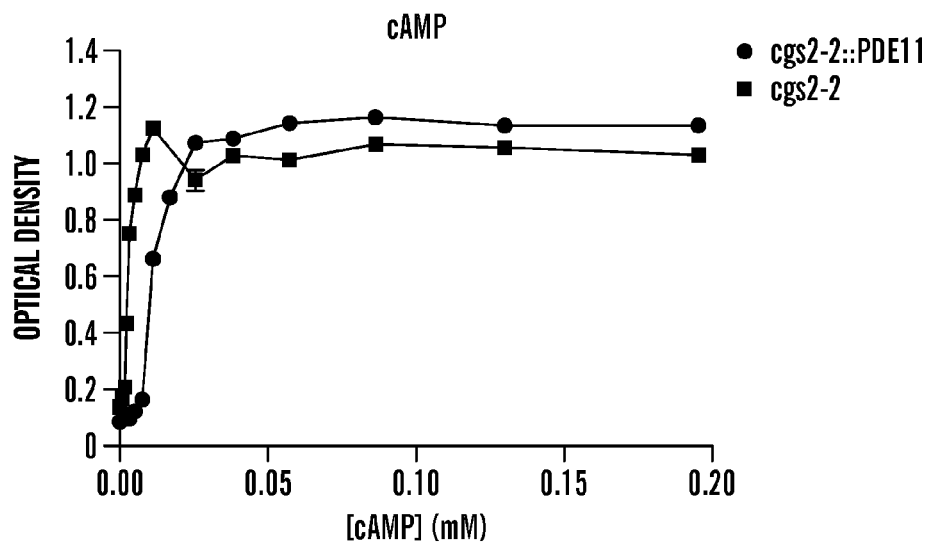
FIG. 6 shows cAMP hydrolysis by the PDE11-expressing strain. 5FOA growth assays with strains lacking PDE activity (squares) or expressing human PDE11A4 (circles) were performed in 0-2 mMcAMP. The rightward shift in the cAMP concentration required for $5FOA^R$ growth is a reflection of PDE activity that hydrolyzes some of the exogenously added cAMP.
Figure 8A:
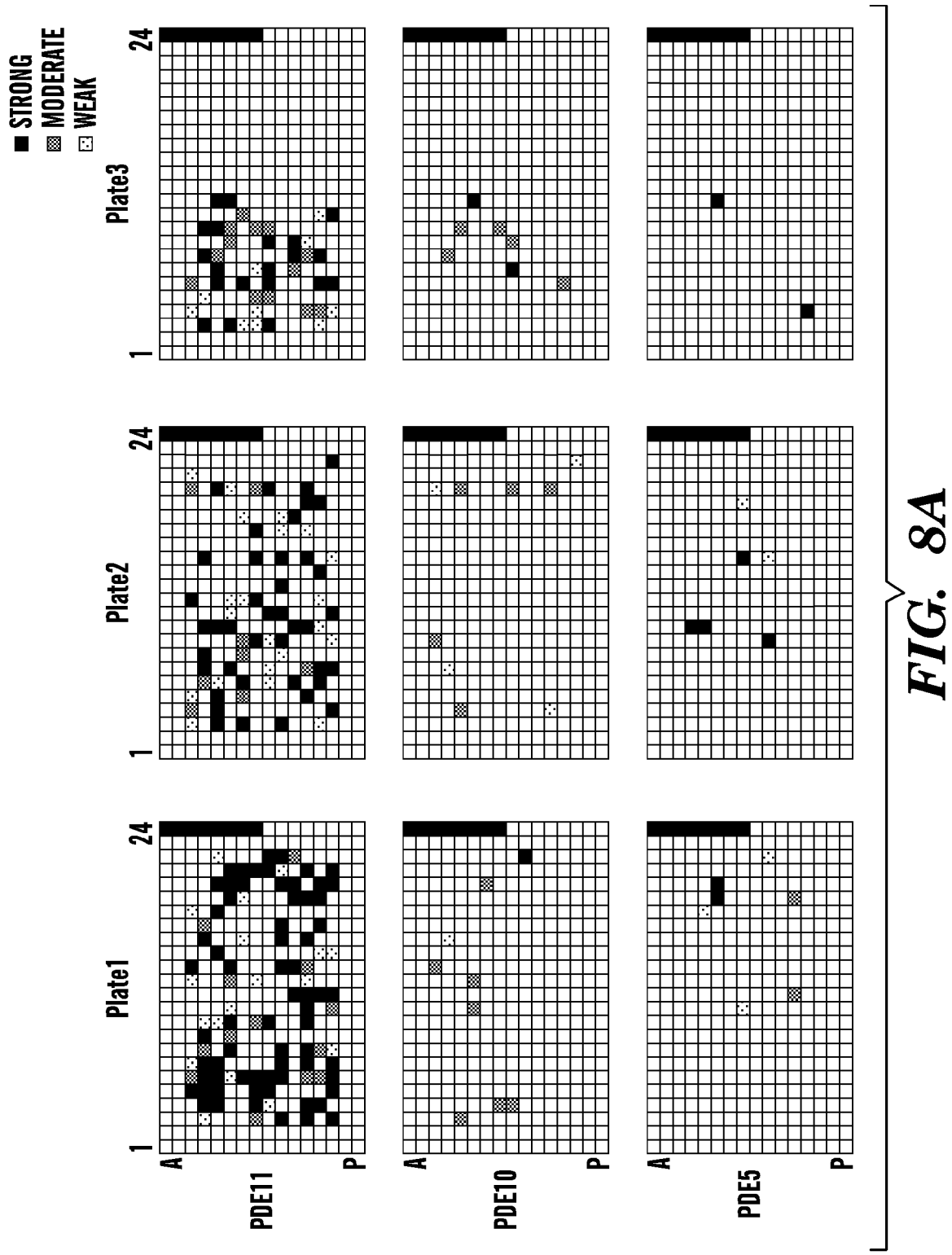

The inventors used a fission yeast-based assay to develop and conduct a HTS for PDE11 inhibitors. The screening strain was generated by replacing the open reading frame of the only S. pombe PDE gene, cgs2$^+$, with a human PDE11A4 cDNA, via homologous recombination (26). Compared with cells that lack PDE activity, cells expressing PDE11A4 require more cyclic nucleotide in the growth medium to achieve 5FOA resistance (FIGS. 1B and 6), indicating that the expressed enzyme is functionally active in yeast.

Figure 1C:
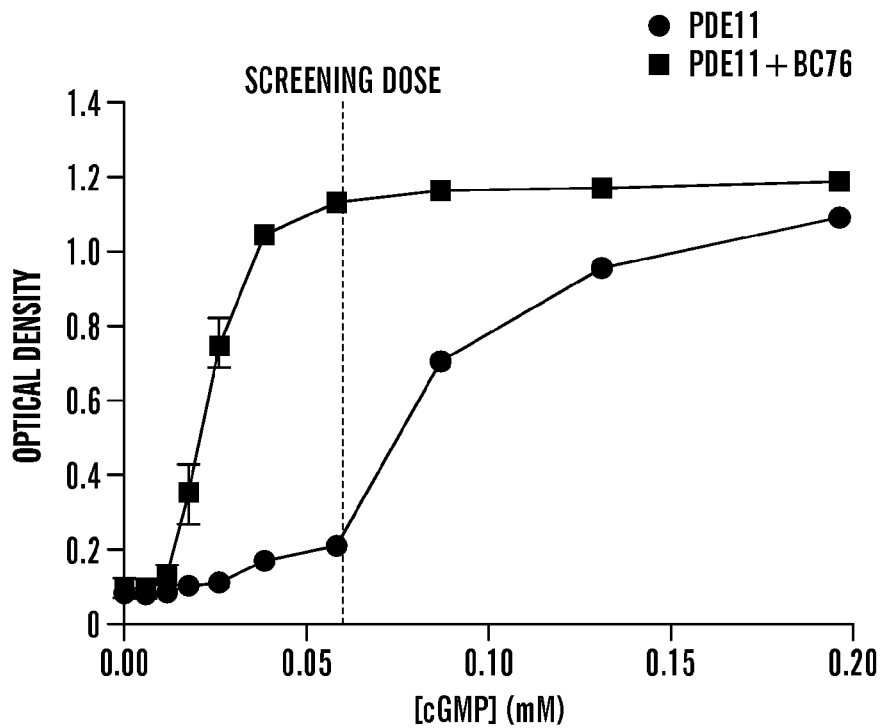

The inventors next optimized the growth and assay conditions for the detection of PDE11 inhibitors, using a previously-identified nonselective PDE inhibitor, BC76 (26) as a positive control. The optimal pre-assay growth conditions, initial cell density, and cGMP concentration in the screening medium that confer saturated growth only in the presence of BC76 were determined. 60 µM cGMP allows cells to grow to saturation (optical density (OD)~1.1) after 48 h at 30° C. in the presence of 25 µM BC76, but fails to promote growth of PDE11-expressing cells in the absence of BC76 (OD~0.2; FIG. 1C).

Figure 2A:
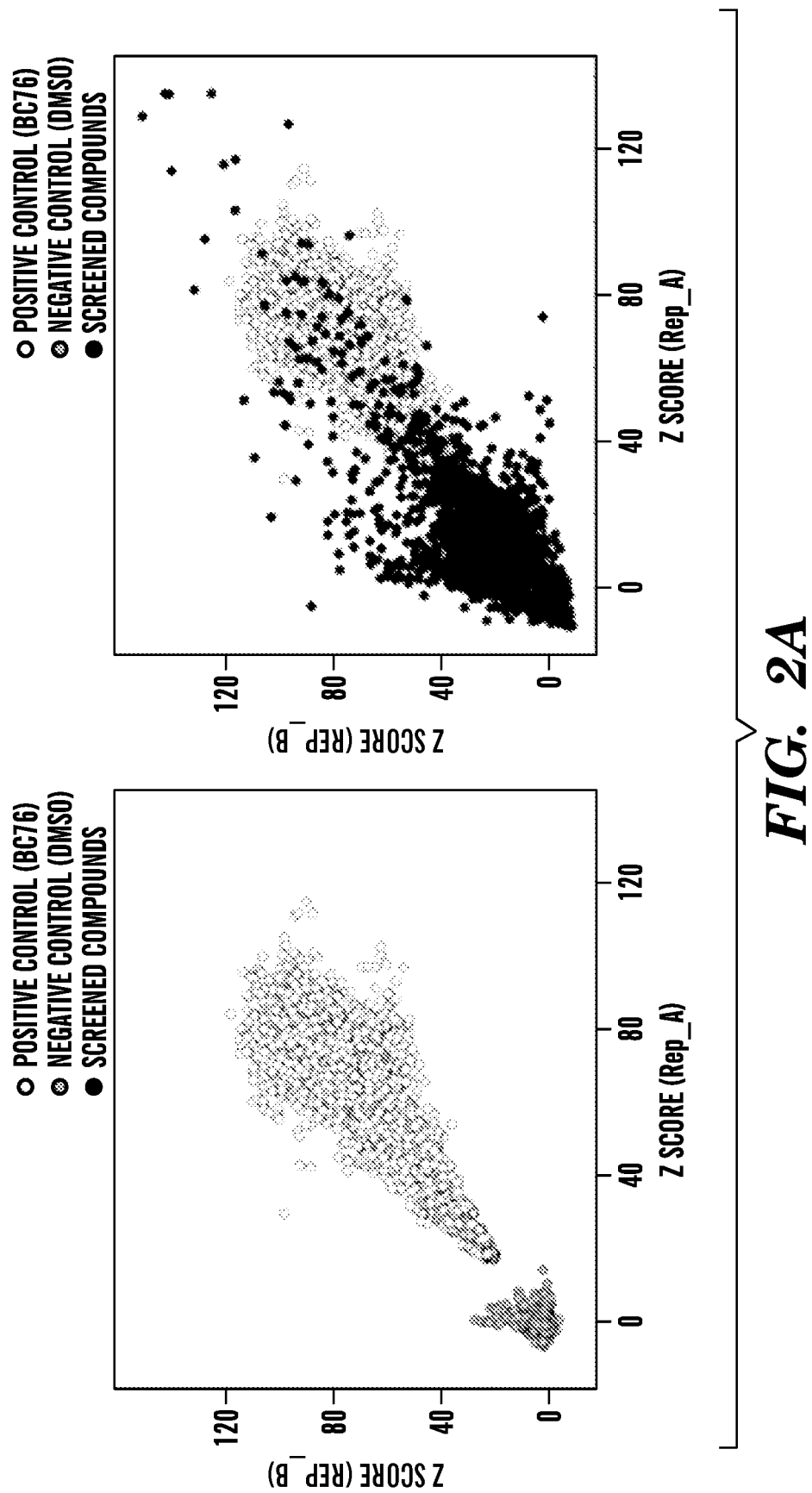
FIGS. 2A-2B show high throughput screen (HTS) data summary.
Figure 2B:
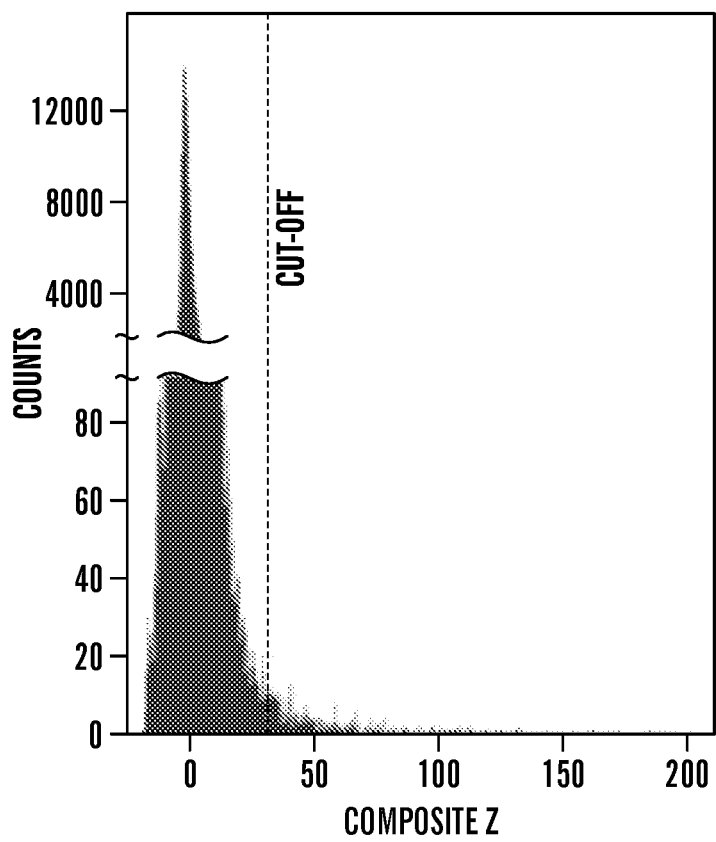

In the HTS, PDE11-expressing cells were grown in 5FOA medium for 48 h in the presence of ~20 µM test compounds, and growth in each well was assessed by measuring OD. Robustness of the screening conditions was determined by a Z'-factor analysis. The optimized screening conditions produced Z'-factors of 0.7-0.9, indicative of a robust screen. 198,382 compounds were screened in duplicate in the primary screen. The Z scores of the duplicate wells are shown in FIG. 2A. Candidate "hit" compounds were defined based on their Composite Z scores, which reflect both the level of growth stimulation and the reproducibility of the replicate assays (FIG. 2B). The Composite Z scores for BC76 positive control wells ranged from 26 to 148. Test compounds that promoted significant 5FOA$^R$ growth were grouped by their Composite Z scores as either strong (>35), moderate (26-35), or weak (20-26) hits (FIG. 7A-7B).

Example 2

Selection of PDE11-Specific Inhibitors

Figure 3A:
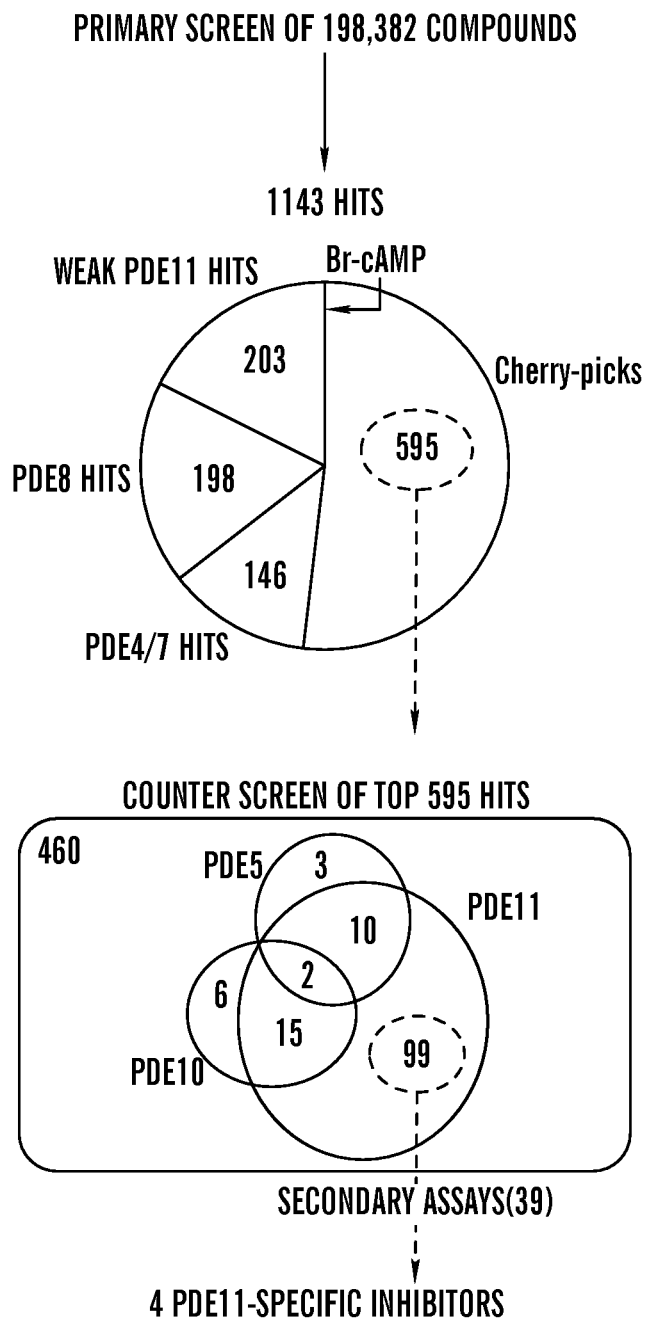

The process by which the inventors analyzed 198,382 compounds to identify four PDE11-specific inhibitors is presented in FIG. 3A. Data from our previous screens for inhibitors of PDE8 (Demirbas, unpublished), PDE4, and PDE7 (24) was used to exclude nonselective PDE inhibitors and compounds that stimulate cell growth via PDE-independent mechanisms (FIG. 3A). For confirmation of hits and to further eliminate non-specific inhibitors, the top 595 hits (0.3% of the total number of compounds screened) were rescreened using strains expressing PDE11, PDE5 and PDE10 (PDE5 and PDE10 are the two PDEs most structurally similar to PDE11). While data from previous screens allowed the inventors to avoid many nonselective and off-target hits, a small group of these primary hits were found to inhibit PDE5 and PDE10 in the subsequent screens (FIG. S3). From the compounds that promoted growth of the PDE11-expressing strain but not the PDE5- or PDE10-expressing strains, 39 lead candidates were selected for secondary assays, based on their potency, selectivity, and structural properties that make them suitable candidates for medicinal chemistry to improve their pharmacokinetic properties.

Figure 3B:
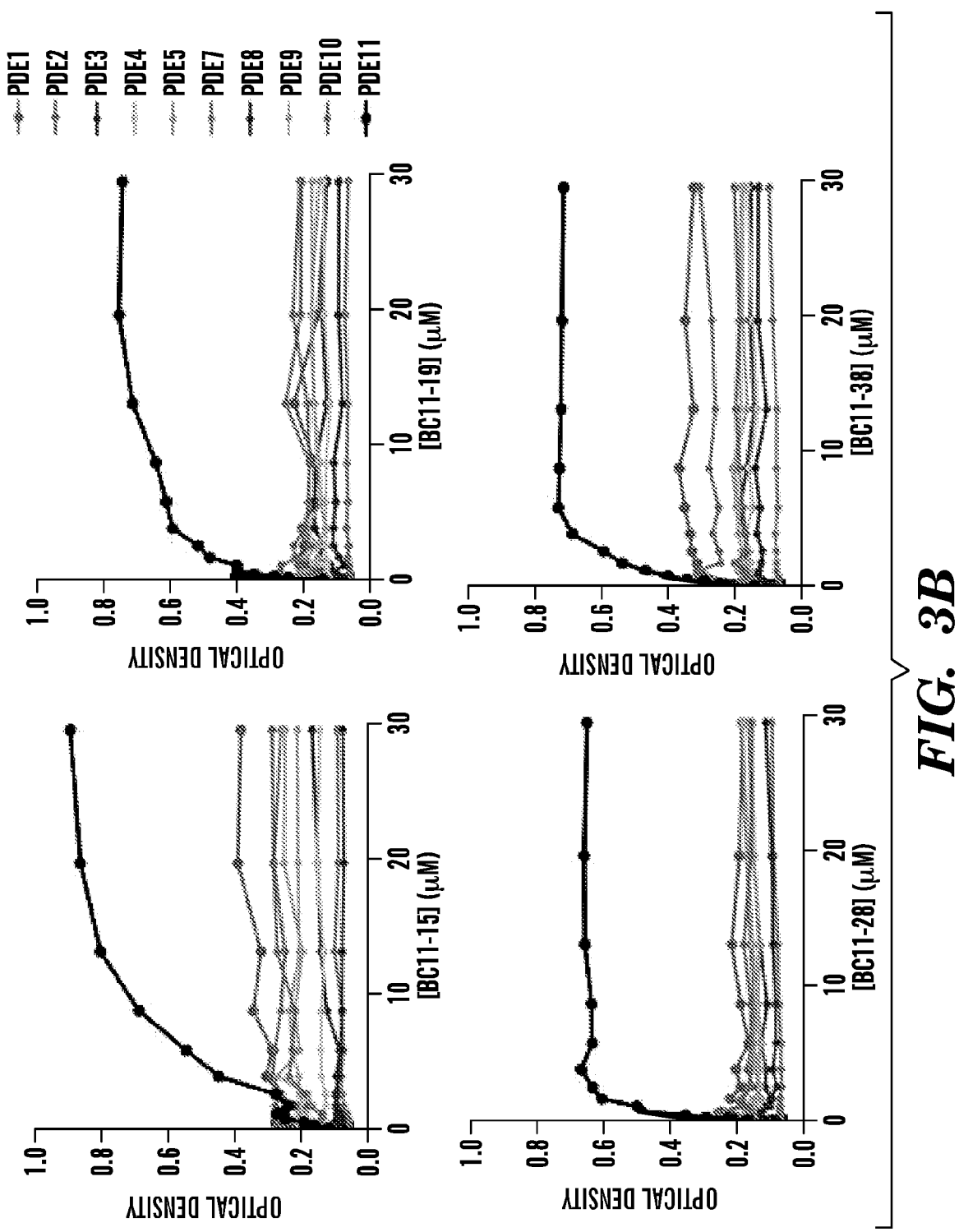

The 39 lead compounds were characterized by 5FOA growth assays using yeast strains that express PDEs representing 10 of the 11 mammalian PDE families (with the exception of PDE6) and in a PDE11 in vitro enzyme assay. Compounds that promoted growth of only the PDE11-expressing strain in the yeast growth assays and had $IC_{50}$ values <2 μM against PDE11 were further tested in in vitro against PDEs 4, 5, 6, 7, 8, and 10. In this manner, the inventors identified four highly selective and potent PDE11 inhibitors. These compounds stimulate growth of the PDE11-expressing strain at <10 μM in 5FOA growth assays, while having little to no effect on any of the strains expressing other PDEs (FIG. 3B). They display $IC_{50}$ values ≤330 nM for PDE11 and >100-fold selectivity for PDE11 relative to other PDEs in in vitro enzyme assays (FIG. 3C). To our knowledge, these compounds are the first identified PDE11-selective inhibitors.

Example 3

Figure 4A:
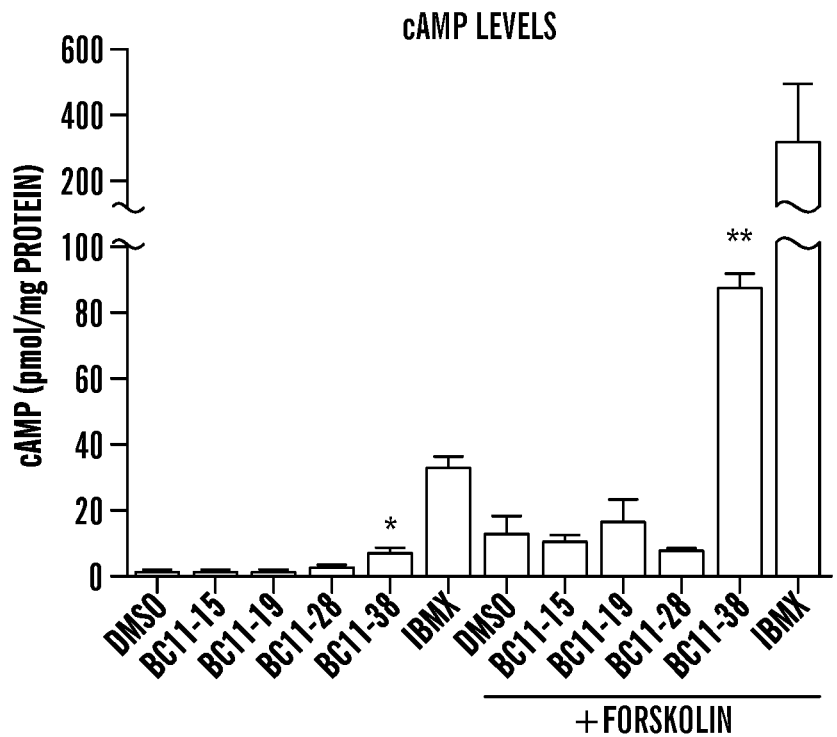
FIGS. 4A-4B show PDE11-selective inhibitors elevate cAMP levels and cortisol production in H295R adrenocortical cells.
Figure 4B:
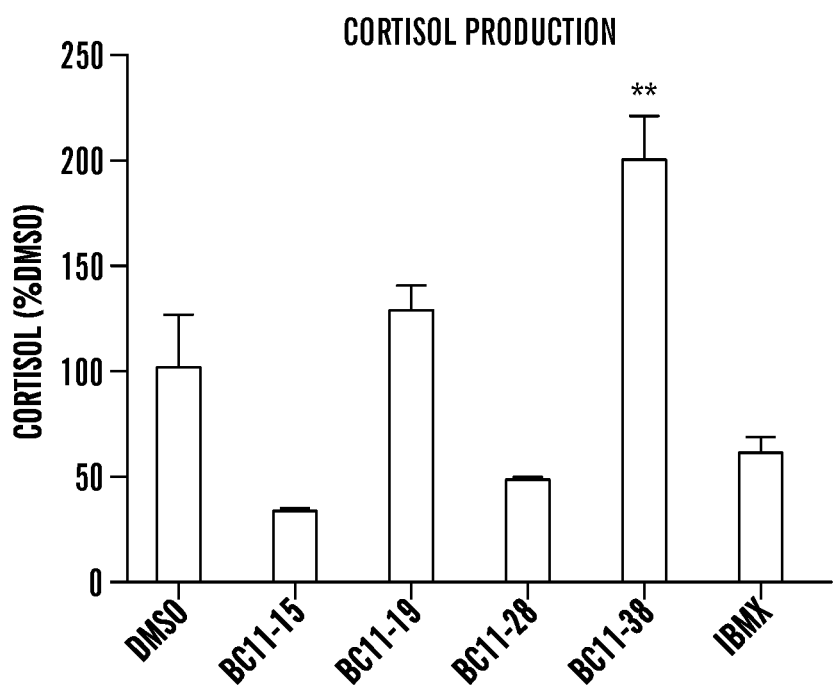

PDE11-Selective Inhibitors Elevate cAMP Levels and Cortisol Production in Adrenocortical Cells PDE11 is expressed in adrenal glands, and PDE11-inactivating mutations, as well as elevated cAMP levels, have been identified in patients with adrenocortical tumors and Cushing syndrome, a condition resulting from excess cortisol release from adrenal tumors (18-21). This demonstrates the possibility that the phenotypes associated with PDE11 inactivation in Cushing syndrome (i.e., elevated cAMP and cortisol levels) could be mimicked by treatment of adrenocortical cells with the PDE11-specific inhibitors which were identified herein. To assess this, the inventors examined the effect of these compounds on H295R human adenocarcinoma cells (27). The inventors discovered that BC11-38 significantly increased cAMP levels and cortisol production in H295R cells, both in the absence and presence of the adenylatecyclase activator forskolin (FIG. 4). As a control, the nonselective PDE inhibitor IBMX (500 μM) was used to eliminate all PDE activity, with the exception of PDE8 and PDE9, in order to assess the relative importance of PDE11 on cAMP hydrolysis in these cells. The data demonstrate that PDE11 is responsible for a significant proportion of the cAMP-degrading activity and has a major role in regulating cortisol production in H295R cells. The lack of an effect on cAMP and cortisol levels by the other PDE11-selective inhibitors suggests either that these compounds fail to enter the cells due to poor solubility in tissue culture media or that the action of BC11-38 is due to an off-target effect.

Example 4

Biological Effects of BC11-38 and Related Compounds are Due to PDE11 Inhibition

Figure 5B:
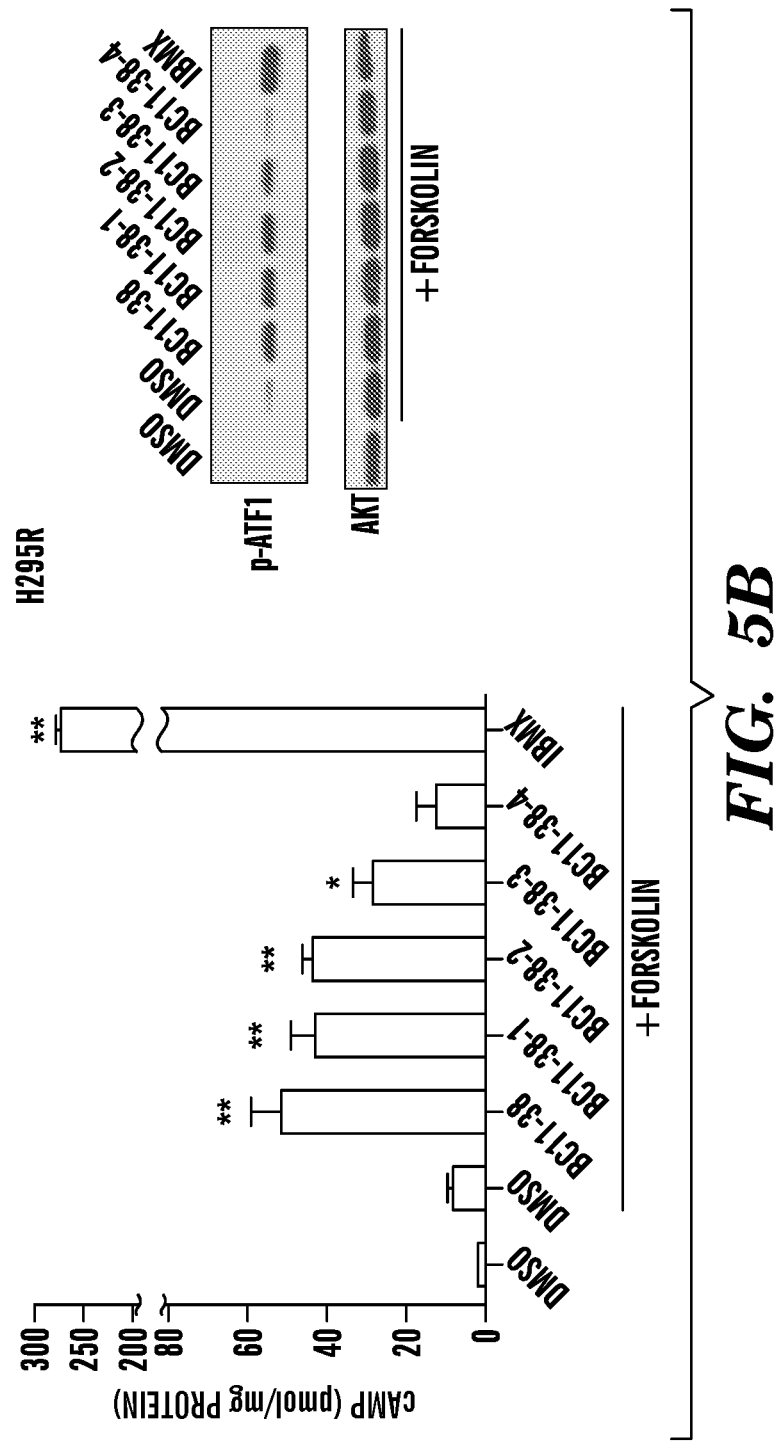
Figure 5C:
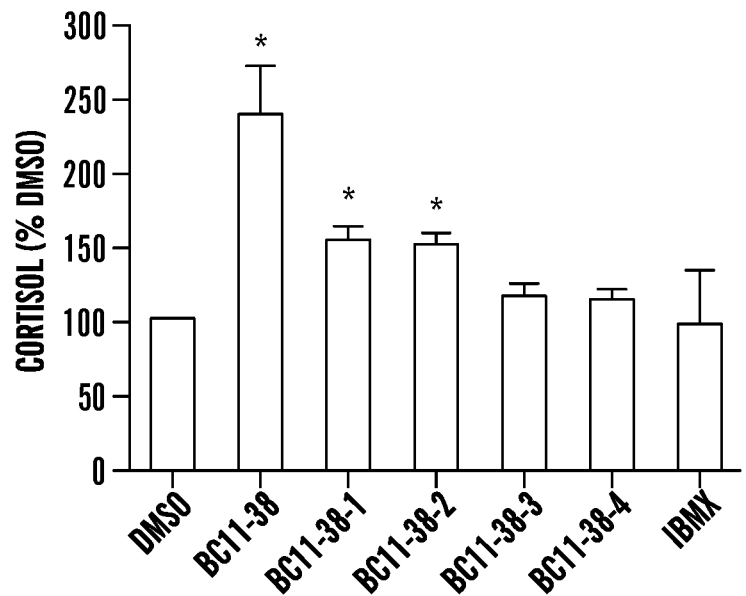
Figure 5D:
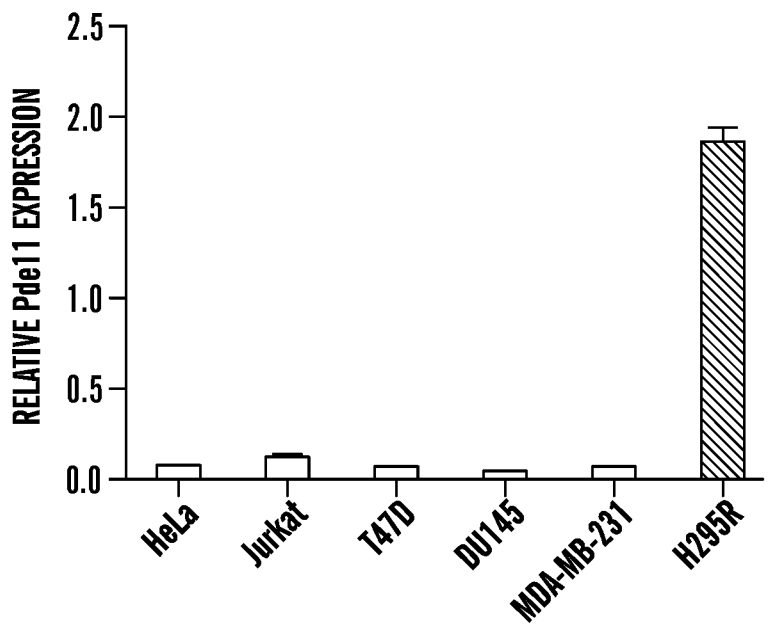
Figure 5E:
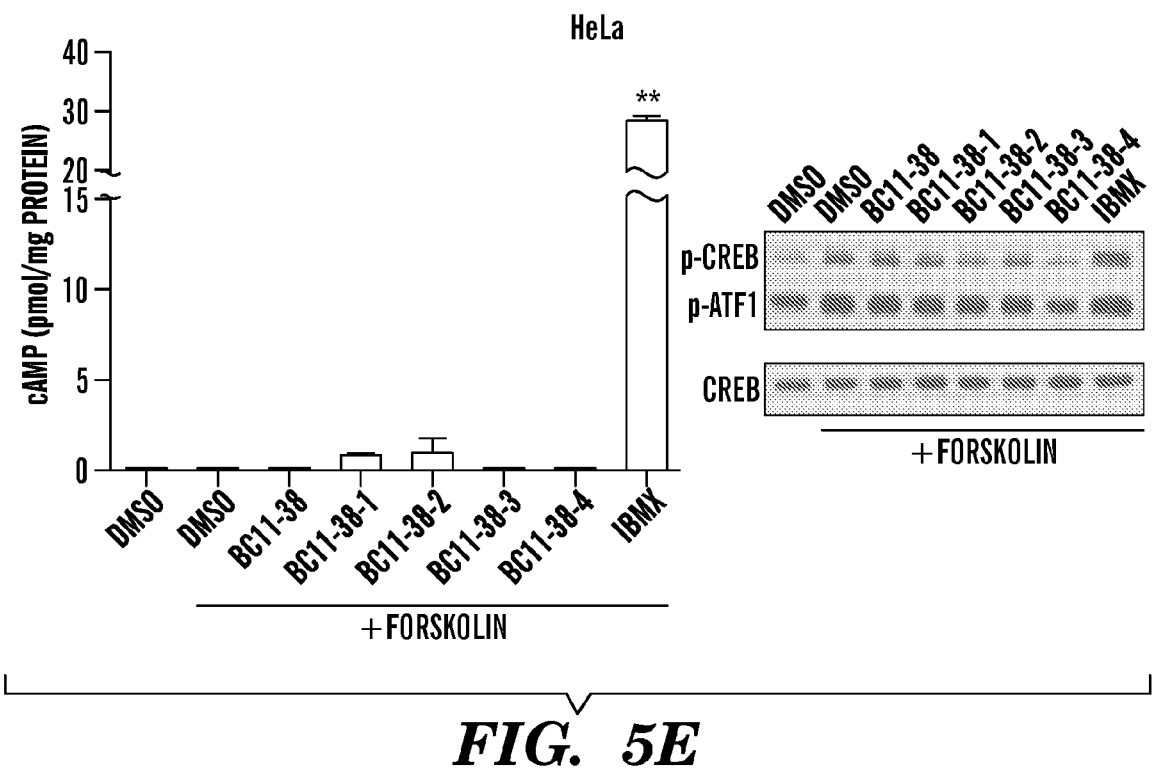

To address the possibility that BC11-38 elevates cAMP levels and cortisol release by H295R cells in a PDE11-independent manner, the inventors analyzed four structural derivatives of BC11-38 that differ by a single methyl or methoxy group. The potency of these compounds against PDE11 (FIG. 5A) correlates with their ability (at 20 μM) to elevate cAMP levels, ATF-1 phosphorylation (FIG. 5B; ATF-1 is phosphorylated by PKA in response to elevated cAMP levels in H295R cells, which lack CREB (28, 29)), and cortisol production (FIG. 5C) in H295R cells. In addition, the inventors examined the PDE11 expression level in a group of cell lines, finding that HeLa cells express very low levels of PDE11 (FIG. 5D). As expected if their activity is due to PDE11 inhibition and not an off-target effect, neither BC11-38 nor the four derivatives have a significant effect on HeLa cells with respect to cAMP or CREB phosphorylation levels (FIG. 5E). These results demonstrate that the biological effects of BC11-38 and related compounds in adrenocortical cells are due to PDE11 inhibition.

Example 5

PDE11 Inhibitor Compounds of Formula (I)-(VI) Induce Human Lymphocytic Leukemia Cell Death In collaboration with other researchers, the effect of different PDE inhibitors on chronic lymphocytic leukemia cells was investigated. The lymphocytic leukemia cells were obtained from individual patients and cannot be maintained in cell culture.

The inventors demonstrate that chronic lymphocytic leukemia cells from one human leukemia patient showed high background levels of apoptosis (programmed cell death), and was not affected by PDE4 (rolipram (referred herein as "roli") or BC8-15) or PDE8 (BC8-1 or BC8-8) inhibition, but demonstrated a an increase in apoptosis upon treatment with either BC11-4 or BC11-8 compounds (Table 1).

TABLE 1

BC11-4 and BC11-8 induced apoptosis of chronic lymphocytic leukemia cells from a first leukemia patient.

|  | % apoptosis | | |
| --- | --- | --- | --- |
|  | DMSO | Rolipram (20 mM) | Analysis |
| DMSO | 49.6 | 46.7 |  |
| BC8-1 (20 mM) | 49.8 | 47.9 | BC11-4 and BC11-8 induce apoptosis in chronic lymphocytic leukemia cells from a patient whose cells do not respond to either PDE4 or PDE8 inhibition. |
| BC8-8 (20 mM) | 49 | 47.6 |  |
| BC8-15 (20 mM) | 47.8 | 50.7 |  |
| BC11-4 (20 mM) | 70.1 | 66.9 | (Rolipram and BC8-15 inhibit PDE4) |
| BC11-8 (20 mM) | 60.1 | 63.3 | (BC8-1 and BC8-8 inhibit PDE8) |

Chronic lymphocytic leukemia cells from a second leukemia patient did not respond to BC11-4 (Table 2), and chronic lymphocytic leukemia cells from a third patient showed increased apoptosis in response to BC11-8, which was additive with the increased apoptosis in response to treatment with rolipram, a PDE4 inhibitor (Table 3).

TABLE 3

Chronic lymphocytic leukemia cells from a second leukemia patient were not inhibited by BC11-4.

|  | % apoptosis | | | |
| --- | --- | --- | --- | --- |
| JM168 | Roli 0 μM | Roli 0.2 μM | Roli 2.0 μM | Roli 20 μM |
| BC11-4 (0 μM) | 6.44 | 12.7 | 24.9 | 33.8 |
| BC11-4 (0.1 μM) | 6.65 | 10.4 | 21.2 | 28.8 |
| BC11-4 (1.0 μM) | 4.71 | 10.8 | 20.8 | 29.6 |
| BC11-4 (10.0 μM) | 5.78 | 4.93 | 6.72 | 15.8 |

TABLE 4

BC11-8 induced apoptosis in chronic lymphocytic leukemia cells from a third leukemia patient, which was additive apoptosis in response to treatment with rolipram (a PDE4 inhibitor).

| JM167 | % apoptosis | | | |
|---|---|---|---|---|
| | Roli 0 μM | Roli 0.2 μM | Roli 2.0 μM | Roli 20 μM |
| BC11-8 (0 μM) | 7.56 | 13.2 | 23.5 | 29.9 |
| BC11-8 (0.1 μM) | 6.31 | 11.7 | 22.7 | 28.2 |
| BC11-8 (1.0 μM) | 7.63 | 13.1 | 19.5 | 26.7 |
| BC11-8 (10.0 μM) | 21.8 | 28.5 | 40.1 | 41.5 |

Treatment of normal T cells with either BC11-4 or BC11-8 (with or without rolipram) did not affect cell viability (Table 5), however, two distinct B cell leukemia cell lines (JVM-2 and REC-1) are not affected by treatment with rolipram (PDE4 inhibitor), but show increased apoptosis when treated with BC11-4 or BC11-8 (Table 6).

TABLE 5

% apoptosis of normal T cells with BC11-4 or BC11-8

| Normal T cells | % apoptosis | |
|---|---|---|
| | DMSO | Rolipram (20 μM) |
| DMSO | 11.2 | 9.4 |
| BC11-4 (20 μM) | 14.3 | 13.9 |
| BC11-8 (20 μM) | 10.3 | 14.7 |
| XRT (10Gy) | 39.3 | 35.9 |

TABLE 6

% apoptosis of two B cell leukemia cell lines (JVM-2 and REC-1) by BC11-4 and BC11-8.

| Drug | Apoptosis (%) | |
|---|---|---|
| | JVM-2 Cells (B cell leukemia) | REC-1 Cells (B cell leukemia) |
| DMSO | 20 | 57.3 |
| Rolipram (20 μM) | 18.5 | 56.7 |
| Roli + Fsk | 16.7 | 49.7 |
| BC11-4 (40 μM) | 32.3 | 100 |
| BC11-8 (40 μM) | 28.8 | 66.2 |

Example 6

Increasingly, yeast-based high throughput screens (HTS) are being used to discover compounds for the study and treatment of human disorders (30, 31). Here, the inventors demonstrate the use of a fission yeast-based screen to identify potent and selective human PDE11 inhibitors. One inhibitor discovered in the screens, BC11-38, along with two derivatives, elevates cAMP levels and cortisol production in adrenocortical cells in a PDE11-specific manner, mimicking the phenotypes observed in Cushing syndrome. The inventors herein have demonstrated that these compounds could serve immediately as useful research tools to study the biological roles of PDE11 in mammalian cells.

This screening platform has several features that aid in the identification of biologically-active PDE inhibitors. First, the target PDEs are full-length proteins expressed in eukaryotic cells, requiring inhibition to occur in the protein-dense yeast cytosol, which resembles the human cytoplasmic environment. Second, compounds are detected by their ability to stimulate cell growth, so that the identified compounds must be cell-permeable, chemically-stable during the 48 h growth period, and non-toxic to S. pombe. This last feature is a proxy for high-specificity, as compounds that promiscuously bind proteins would likely retard or inhibit growth. Other favorable features of this screen include the ability to detect both active-site and allosteric inhibitors and the use of a simple readout to rapidly screen large compound libraries. This 384-well format assay allowed us to screen 200,000 compounds, which is larger than any previously published yeast-based HTS, to our knowledge. Our ability to identify potent PDE inhibitors that are biologically active in mammalian cells in this and other HTS's confirms that S. pombe is well-suited for chemical screening. Using strains that express 10 of the 11 PDE families, we were able to profile inhibitor specificity and eliminate the majority of nonselective compounds prior to performing in vitro enzyme assays. Similarly, future PDE inhibitor screens will benefit from the database developed from this and previous screens to filter out non-selective PDE inhibitors and compounds that act in a PDE-independent manner.

While the overall frequency of strong and moderate hits in this screen was 0.36%, this frequency varied significantly among the compound libraries (FIG. S2A). Of the large libraries screened the highest frequencies of hits were observed in the ActimolTimTec 1 (0.8%; 68 hits from 8,518 compounds), Chembridge 3 (0.7%; 74 hits from 10,560 compounds), and ChemDiv 6 (0.64%; 283 from 44,000 compounds) libraries. In contrast, the lowest frequency of hits was observed in the ChemDiv 1 library (0.04%; 6 hits from 16,544 compounds), which may reflect the fact that this was one of the oldest libraries screened and repeated freezing and thawing during previous screens may have adversely affected these compounds. Interestingly, the four compounds presented in FIG. 3 came from four different libraries produced by four different companies (BC11-15, Enamine T0515-1965; BC11-19, Maybridge BTB 12009; BC11-28, ChemDiv K405-0344; BC11-38, Life Chemicals F0579-0060).

One unexpected result was that many of the compounds identified in the initial screen were not validated as PDE11 hits in cherry-picking experiments. This is likely due to the different delivery method as the cherry-pick screens use pocket tips rather than the steel pin arrays used in the primary screens. It appears that the pocket tip method of introducing compounds to microtiter dishes fails to allow some compounds to dissolve in the growth medium. Thus, selection of only validated hits for secondary assays may have excluded compounds with poor solubility in growth medium.

PDE11A inactivating mutations were suggested as predisposing factors in the development of adrenocortical hyperplasia (18). In these tumors, elevated cAMP levels and increased CREB phosphorylation result in excess cortisol release, leading to Cushing syndrome. Herein the inventors confirm the role of PDE11 in cortisol production by adrenocortical cells, using selective inhibitors. The inventors demonstrate the disease phenotypes linked to inactivating mutations in PDE11A gene using pharmacological inhibitors of the enzyme in adrenocortical cells, thus phenocopying a genetic disorder using small molecules. This directly demonstrates a link between the loss of PDE11 function with phenotypes related to adrenal hyperplasia and Cushing syndrome.

Among the four initial PDE11-specific inhibitors, one compound, BC11-38, along with two derivatives, significantly elevates cAMP and cortisol levels in H295R cells. The lack of this effect by the other compounds does not argue against the PDE11-specific effect of BC11-38, since it is most likely related to problems with entry of the compounds into mammalian cells, either due to poor solubility or being bound up by components of the growth media. Indeed, compound crystals were observed in the cell culture media in wells containing the three ineffective compounds, indicating solubility problems. Due to their biological activity, BC11-38 and its two active derivatives represent a logical starting point for medicinal chemistry approaches to enhance their potency, specificity, and pharmacokinetic properties, to develop compounds suitable for whole animal studies of PDE11 function. Such compounds could produce an acute loss of PDE11 activity as a way of identifying biological roles for PDE11, which might be overlooked in knock-out mouse studies due to compensation of activity by other PDEs or developmental alterations caused by an early loss of PDE11 activity. These compounds could also serve as therapeutic candidates to treat adrenal insufficiencies that lead to cortisol deficiency, such as Addison's disease. Herein the inventors have used the assay as a "proof of principle" that the yeast-based platform described herein can be used in chemical screens to identify potent and selective PDE inhibitors that may be effective in cell culture studies even prior to medicinal chemistry efforts. Such specific compounds will be powerful tools to enhance our understanding of PDEs and to develop therapeutics for several diseases related to cyclic nucleotide signaling defects.

REFERENCES

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

Accordingly, the references are each incorporated herein in their entirety by reference.

REFERENCES

1. Bender A T & Beavo J A (2006) Cyclic nucleotide phosphodiesterases: molecular regulation to clinical use. Pharmacol Rev 58(3):488-520.
2. Conti M & Beavo J (2007) Biochemistry and physiology of cyclic nucleotide phosphodiesterases: essential components in cyclic nucleotide signaling. Annu Rev Biochem 76:481-511.
3. Fawcett L, et al. (2000) Molecular cloning and characterization of a distinct human phosphodiesterase gene family: PDE11A. Proc Natl Acad Sci USA 97(7):3702-3707.
4. Hetman J M, et al. (2000) Cloning and characterization of two splice variants of human phosphodiesterase 11A. Proc Natl Acad Sci USA 97(23):12891-12895.
5. Yuasa K, et al. (2000) Isolation and characterization of two novel phosphodiesterase PDE11A variants showing unique structure and tissue-specific expression. J Biol Chem 275(40):31469-31479.
6. D'Andrea M R, et al. (2005) Expression of PDE11A in normal and malignant human tissues. J Histochem Cytochem 53(7):895-903.
7. Loughney K, Taylor J, & Florio V A (2005) 3',5'-cyclic nucleotide phosphodiesterase 11A: localization in human tissues. Int J Impot Res 17(4):320-325.
8. Lakics V, Karran E H, & Boess F G (2010) Quantitative comparison of phosphodiesterase mRNA distribution in human brain and peripheral tissues. Neuropharmacology 59(6):367-374.
9. Seftel A D (2005) Phosphodiesterase 11 (PDE11) regulation of spermatozoa physiology. J Urol 174(3):1043-1044.
10. Wayman C, et al. (2005) Phosphodiesterase 11 (PDE11) regulation of spermatozoa physiology. Int J Impot Res 17(3):216-223.
11. Kelly M P, et al. (2010) Phosphodiesterase 11A in brain is enriched in ventral hippocampus and deletion causes psychiatric disease-related phenotypes. Proc Natl Acad Sci USA 107(18):8457-8462.
12. Fatemi S H, Folsom T D, Reutiman T J, & Vazquez G (2010) Phosphodiesterase signaling system is disrupted in the cerebella of subjects with schizophrenia, bipolar disorder, and major depression. Schizophr Res 119(1-3):266-267.
13. Wong M L, et al. (2006) Phosphodiesterase genes are associated with susceptibility to major depression and antidepressant treatment response. Proc Natl Acad Sci USA 103(41):15124-15129.
14. Horvath A, et al. (2009) Functional phosphodiesterase 11A mutations may modify the risk of familial and bilateral testicular germ cell tumors. Cancer Res 69(13):5301-5306.
15. Faucz F R, et al. (2011) Phosphodiesterase 11A (PDE11A) genetic variants may increase susceptibility to prostatic cancer. J Clin Endocrinol Metab 96(1):E135-140.
16. DeWan A T, et al. (2010) PDE11A associations with asthma: results of a genome-wide association scan. J Allergy Clin Immunol 126(4):871-873 e879.
17. Libe R, et al. (2011) Frequent phosphodiesterase 11A gene (PDE11A) defects in patients with Carney complex (CNC) caused by PRKAR1A mutations: PDE11A may contribute to adrenal and testicular tumors in CNC as a modifier of the phenotype. J Clin Endocrinol Metab 96(1): E208-214.
18. Horvath A, et al. (2006) A genome-wide scan identifies mutations in the gene encoding phosphodiesterase 11A4 (PDE11A) in individuals with adrenocortical hyperplasia. Nat Genet 38(7):794-800.
19. Carney J A, Gaillard R C, Bertherat J, & Stratakis C A (2010) Familial micronodular adrenocortical disease, Cushing syndrome, and mutations of the gene encoding phosphodiesterase 11A4 (PDE11A). Am J Surg Pathol 34(4):547-555.
20. Boikos S A, et al. (2008) Phosphodiesterase 11A expression in the adrenal cortex, primary pigmented nodular adrenocortical disease, and other corticotropin-independent lesions. Horm Metab Res 40(5):347-353.
21. Horvath A, et al. (2006) Adrenal hyperplasia and adenomas are associated with inhibition of phosphodiesterase 11A in carriers of PDE11A sequence variants that are frequent in the population. Cancer Res 66(24):11571-11575.

22. Bischoff E (2004) Potency, selectivity, and consequences of nonselectivity of PDE inhibition. Int J Impot Res 16 Suppl 1:S11-14.
23. Ivey F D, Wang L, Demirbas D, Allain C, & Hoffman C S (2008) Development of a fission yeast-based high-throughput screen to identify chemical regulators of cAMP phosphodiesterases. J Biomol Screen 13(1):62-71.
24. Alaamery M A, et al. (2010) New classes of PDE7 inhibitors identified by a fission yeast-based HTS. J Biomol Screen 15(4):359-367.
25. Demirbas D, Ceyhan O, Wyman A R, & Hoffman C S (2011) A Fission Yeast-Based Platform for Phosphodiesterase Inhibitor HTSs and Analyses of Phosphodiesterase Activity. Handb Exp Pharmacol (204):135-149.
26. Demirbas D, et al. (2011) Use of a *Schizosaccharomyces pombe* PKA-repressible reporter to study cGMP metabolising phosphodiesterases. Cell Signal 23(3):594-601.
27. Rainey W E, Bird I M, & Mason J I (1994) The NCI-H295 cell line: a pluripotent model for human adrenocortical studies. Mol Cell Endocrinol 100(1-2):45-50.
28. Groussin L, Massias J F, Bertagna X, & Bertherat J (2000) Loss of expression of the ubiquitous transcription factor cAMP response element-binding protein (CREB) and compensatory overexpression of the activator CREMtau in the human adrenocortical cancer cell line H295R. J Clin Endocrinol Metab 85(1):345-354.
29. Rosenberg D, et al. (2002) Role of the PKA-regulated transcription factor CREB in development and tumorigenesis of endocrine tissues. Ann N Y Acad Sci 968:65-74.
30. Marjanovic J, et al. (2010) Recombinant yeast screen for new inhibitors of human acetyl-CoA carboxylase 2 identifies potential drugs to treat obesity. Proc Natl Acad Sci USA 107(20):9093-9098.
31. Couplan E, et al. (2011) A yeast-based assay identifies drugs active against human mitochondrial disorders. Proc Natl Acad Sci USA 108(29):11989-11994.
32. Wang H, Liu Y, Chen Y, Robinson H, & Ke H (2005) Multiple elements jointly determine inhibitor selectivity of cyclic nucleotide phosphodiesterases 4 and 7. J Biol Chem 280(35):30949-30955.
33. Rainey W E, et al. (1993) Regulation of human adrenal carcinoma cell (NCI-H295) production of C19 steroids. J Clin Endocrinol Metab 77(3):731-737.
34. Sarbassov D D, et al. (2006) Prolonged rapamycin treatment inhibits mTORC2 assembly and Akt/PKB. Mol Cell 22(2):159-168.
35. Wang L, Griffiths K, Jr., Zhang Y H, Ivey F D, & Hoffman C S (2005) *Schizosaccharomyces pombe* adenylate cyclase suppressor mutations suggest a role for cAMP phosphodiesterase regulation in feedback control of glucosecAMP signaling. Genetics 171(4):1523-1533.
Alves, C., T. C. Robazzi, et al. (2008). "Withdrawal from glucocorticosteroid therapy: clinical practice recommendations." Jornal de pediatria 84(3): 192-202.
Cote, M., G. Guillon, et al. (2001). "Expression and regulation of adenylyl cyclase isoforms in the human adrenal gland." The Journal of clinical endocrinology and metabolism 86(9): 4495-4503.
Einaudi, S., N. Bertorello, et al. (2008). "Adrenal axis function after high-dose steroid therapy for childhood acute lymphoblastic leukemia." Pediatric blood & cancer 50(3): 537-541.
Kurtoglu, S., D. Sarici, et al. (2011). "Fetal adrenal suppression due to maternal corticosteroid use: case report." Journal of clinical research in pediatric endocrinology 3(3): 160-162.
Mims, R. B. (1977). "Suppression of the hypothalamic-pituitary-adrenal axis after subcutaneous cortisone acetate administration in rats." Journal of the National Medical Association 69(12): 873-878.
Neidert, S., P. Schuetz, et al. (2010). "Dexamethasone suppression test predicts later development of an impaired adrenal function after a 14-day course of prednisone in healthy volunteers." European journal of endocrinology European Federation of Endocrine Societies 162(5): 943-949.

---

The invention claimed is:
1. A compound for inhibiting phosphodiesterase 11 (PDE11) selected from the group consisting of:
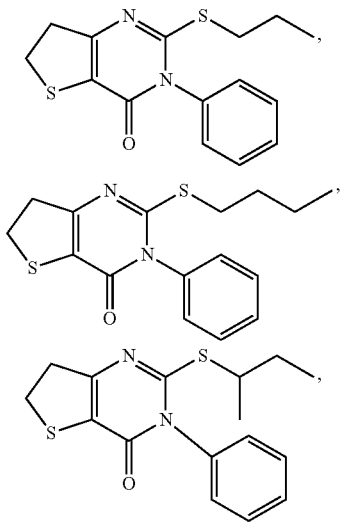
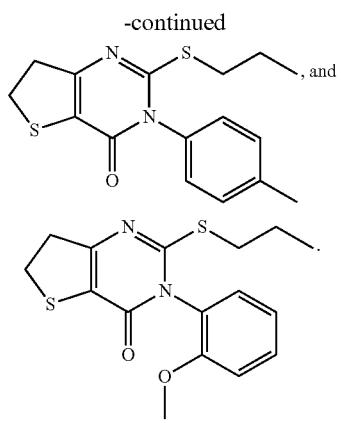
2. A kit comprising one or more compounds of claim 1, and instructions for administration to a subject.
3. A pharmaceutical composition comprising at least one compound of claim 1 and a pharmaceutically acceptable carrier.
* * * * *